United States Patent [19]

Clegg et al.

[11] Patent Number: 5,547,972
[45] Date of Patent: Aug. 20, 1996

[54] THERAPEUTIC AGENTS USEFUL FOR TREATING INFLAMMATORY DISEASES

[75] Inventors: Lawrence S. Clegg; Ian M. Hunneyball; Colin G. P. Jones; Paul Rafferty; Leslie Steele, all of Nottinghamshire, United Kingdom

[73] Assignee: The Boots Company PLC, Notts, England

[21] Appl. No.: 244,246

[22] PCT Filed: Dec. 12, 1992

[86] PCT No.: PCT/EP92/02899

§ 371 Date: Jun. 3, 1994

§ 102(e) Date: Jun. 3, 1994

[87] PCT Pub. No.: WO93/13075

PCT Pub. Date: Jul. 8, 1993

[30] Foreign Application Priority Data

Dec. 23, 1991 [GB] United Kingdom ............ 9127304

[51] Int. Cl.$^6$ ............ A61K 31/415; C07D 233/61
[52] U.S. Cl. ............ 514/399; 548/335.5
[58] Field of Search ............ 514/399; 548/335.5

[56] References Cited

U.S. PATENT DOCUMENTS

| | | |
|---|---|---|
| 3,821,241 | 6/1974 | Schmidt et al. . |
| 4,226,878 | 10/1980 | Iizuka et al. . |
| 4,338,453 | 7/1982 | Gall . |
| 4,378,361 | 3/1983 | Schromm et al. . |
| 4,404,387 | 9/1983 | Gall . |
| 4,581,370 | 4/1986 | Diamond et al. . |
| 4,599,427 | 7/1986 | Oeckl et al. . |

FOREIGN PATENT DOCUMENTS

| | | |
|---|---|---|
| 0003560 | 8/1979 | European Pat. Off. . |
| 0062918 | 10/1982 | European Pat. Off. . |
| 0081324 | 6/1983 | European Pat. Off. . |
| 0105575 | 4/1984 | European Pat. Off. . |
| 0117462 | 9/1984 | European Pat. Off. . |
| 0132366 | 1/1985 | European Pat. Off. . |
| 0230035 | 12/1986 | European Pat. Off. . |
| 0274867 | 7/1988 | European Pat. Off. . |
| 0407217 | 1/1991 | European Pat. Off. . |
| 0485890 | 5/1992 | European Pat. Off. . |
| 63-141969 | 6/1988 | Japan . |
| 1244530 | 9/1971 | United Kingdom . |
| 1341375 | 12/1973 | United Kingdom . |
| 1354909 | 5/1974 | United Kingdom . |
| 2003154 | 3/1979 | United Kingdom . |
| 2088888 | 6/1982 | United Kingdom . |
| 2159148 | 11/1985 | United Kingdom . |
| 91/09857 | 7/1991 | WIPO . |
| 93/14070 | 7/1993 | WIPO . |

OTHER PUBLICATIONS

Ferroni et al, Il Farmaco, 44(5), 495–502, (1989).
Sadanandam et al, Ind. J. Pharmac. 5(4), 428–441, (1973).
Sadanandam et al, Pfl. Krankh. 3/75, 149–161, (1975).
Traylor et al, J. Am. Chem. Soc., 101:18, 5376–5383, (1979).
Luts et al, J. Pharm. Sciences 61, 1504–1506, (1972).
Godefroi et al, J. Med. Chem. 12, 784–791, (1969).
Sidhu et al, Arch. Pharmaz. 306, 310–319, (1973).

*Primary Examiner*—Jacqueline Haley
*Attorney, Agent, or Firm*—Nikaido, Marmelstein, Murray & Oram LLP

[57] ABSTRACT

This invention relates to compounds of formula I and pharmaceutically acceptable salts thereof

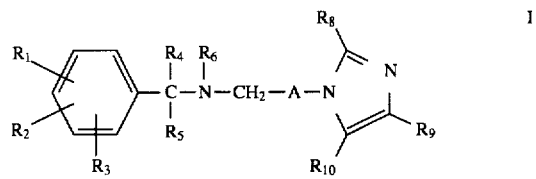

in which $R_1$, $R_2$ and $R_3$ independently represent hydrogen, halo, alkyl, alkoxy, phenoxy, phenyl, alkoxycarbonyl, —$NR_{13}R_{14}$, halogenated alkoxy, halogenated alkyl, benzyloxy, hydroxy, hydroxyalkyl, ($C_{2-6}$ alkoxycarbonyl)vinyl, —$S(O)_nR_7$, carbamoylalkyl, alkoxycarbonylalkyl, —$CONR_{11}R_{12}$, or $R_1$ and $R_2$ together with the phenyl ring represent a naphthyl group; $R_4$ and $R_5$ independently represent hydrogen, alkyl, phenyl or together with the carbon atom represent $C_{3-6}$ cycloalkyl; $R_6$ represents hydrogen, alkyl or ω-hydroxy alkyl; A represents $C_{2-9}$ alkylene; $R_8$ represents hydrogen, alkyl, halo, alkoxy, hydroxyalkyl, benzyl or phenyl; $R_9$ and $R_{10}$ independently represent hydrogen, alkyl, halo, alkoxy, phenyl, hydroxyalkyl, alkoxycarbonyl, nitro, —$NR_{30}R_{31}$, alkanoyloxyalkyl, or aminomethyl; which are antiinflammatory and antiallergic agents. Compositions containing these compounds and processes to make them are also disclosed.

14 Claims, No Drawings

THERAPEUTIC AGENTS USEFUL FOR TREATING INFLAMMATORY DISEASES

This is a National Stage Application of PCT/EP92/02899 filed on Dec. 12, 1992 which published as WO93/13075 on Jul. 8, 1993.

This invention relates to novel 1-(arylalkylaminoalkyl)imidazole compounds having therapeutic activity useful in treating conditions associated with inflammation or allergy, to therapeutic compositions containing these novel compounds and to processes for preparing these novel compounds.

It is believed that, in response to an inflammatory stimulus, phospholipase enzymes are activated leading to the release of arachidonic acid from phospholipids. Existing non-steroidal antiinflammatory agents (NSAIA) are believed to act primarily by blocking the conversion of this released arachidonic acid into prostaglandins via the cyclo-oxygenase pathway of the arachidonic acid cascade. Many existing NSAIA are unsuitable for use by asthmatics. We have found a series of compounds which act to block the release of arachidonic acid from phospholipids. These compounds are indicated as useful antiinflammatory compounds with a potentially broader spectrum of activity than existing NSAIA, and potentially fewer gastro-intestinal side-effects. In addition the compounds may be useful in the treatment of asthma.

Compound A is disclosed in Il Farmaco, 44 (5), 495–502, 1989 as having an inhibitory effect on platelet aggregation in vitro.

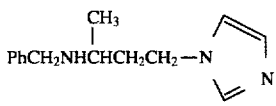

Compound B is disclosed as a chemical intermediate in EP 0230035. No pharmacological activity is disclosed for this compound.

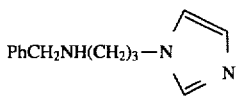

GB 2088888 discloses desensitizing compositions for photographic developers comprising imidazoles of formula C

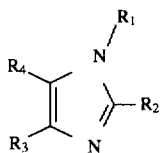

wherein $R_1$ represents a hydrogen atom, a $C_{1-20}$ alkyl group or a $C_{6-20}$ aryl group; $R_2$ represents a hydrogen atom, a $C_{1-20}$ alkyl group, a $C_{6-20}$ aryl group, an amino group, or a $C_{1-20}$ alkylthio group; and $R_3$ and $R_4$, which may be the same or different, each represents a hydrogen atom, a $C_{1-4}$ alkyl group, or a $C_{6-20}$ aryl group; and $R_1$, $R_2$, $R_3$ and $R_4$ may be substituted. 1-(6-Benzylaminohexyl)- 2-methylimidazole is disclosed. No pharmacological activity is disclosed for this compound.

More distantly related compounds of formula D

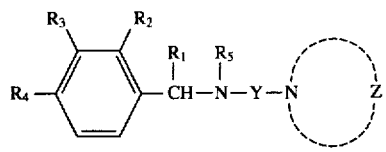

in which the ring incorporating N and Z represents dialkylamino, morpholino or piperidino are disclosed in the Indian Journal of Pharmacology 1973, 5, 428 and Pfl. Krankh. 1975, 3, 149. These compounds are disclosed as potential central nervous system depressants. N-[2-(4-Morpholino)propyl]-α-ethyl-3,4-dichlorobenzylamine is alleged to have antiinflanmmtory activity but has a wide range of undesirable side-effects in mice.

The present invention provides novel compounds of formula I

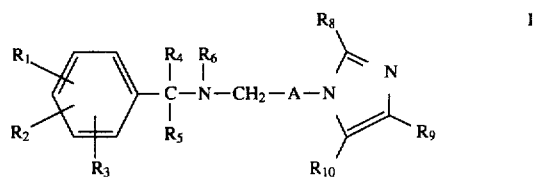

and pharmaceutically acceptable salts thereof in which $R_1$, $R_2$ and $R_3$ independently represent hydrogen, halo, a $C_{1-6}$ alkyl group, a $C_{1-6}$ alkoxy group, phenoxy (optionally substituted by a $C_{1-4}$ alkyl group, a $C_{1-4}$ alkoxy group or halo), phenyl (optionally substituted by a $C_{1-4}$ alkyl group, a $C_{1-4}$ alkoxy group or halo), a $C_{2-6}$ alkoxycarbonyl group, an amino group of formula —$NR_{13}R_{14}$ (in which $R_{13}$ and $R_{14}$ are independently hydrogen or a $C_{1-4}$ alkyl Group or $R_{13}$ and $R_{14}$ together with the nitrogen atom to which they are attached represent a pyrrolidine ring, a morpholine ring or a piperidine ring), a halogenated $C_{1-4}$ alkoxy group, a halogenated $C_{1-4}$ alkyl group, benzyloxy (optionally substituted by a $C_{1-4}$ alkyl group, a $C_{1-4}$ alkoxy Group or halo), hydroxy, a $C_{1-4}$ hydroxyalkyl group, a ($C_{2-6}$ alkoxycarbonyl)vinyl group; a group of formula —$S(O(_nR_7$ (in which $R_7$ represents a $C_{1-4}$ alkyl Group and n is 0, 1 or 2), a $C_{2-4}$ carbamoylalkyl Group, a $C_{2-6}$ alkoxycarbonyl $C_{1-2}$ alkyl group, a carbamoyl Group of formula —$CONR_{11}R_{12}$ (in which $R_{11}$ and $R_{12}$ are independently hydrogen or a $C_{1-6}$ alkyl group) or $R_1$ and $R_2$ together with the phenyl ring to which they are attached represent a naphthyl group;

$R_4$ and $R_5$ independently represent hydrogen, a $C_{1-4}$ alkyl group, phenyl (optionally substituted by a $C_{1-4}$ alkyl group, halo or a $C_{1-4}$ alkoxy group) or $R_4$ and $R_5$ together with the carbon atom to which they are attached represent a $C_{3-6}$ cycloalkyl group;

$R_6$ represents hydrogen, a $C_{1-4}$ alkyl group or an ω-hydroxy $C_{1-4}$ alkyl group;

A represents a $C_{2-9}$ alkylene group, which may be straight or branched;

$R_8$ represents hydrogen, a $C_{1-6}$ alkyl group, halo, a $C_{1-4}$ alkoxy group, a $C_{1-4}$ hydroxyalkyl group, phenyl (optionally substituted by a $C_{1-4}$ alkyl group, halo or a $C_{1-4}$ alkoxy group) or benzyl (optionally substituted by a $C_{1-4}$ alkyl group, halo or a $C_{1-4}$ alkoxy group);

$R_9$ and $R_{10}$ independently represent hydrogen, a $C_{1-6}$ alkyl group, halo, a $C_{1-4}$ alkoxy group, phenyl (optionally substituted by a $C_{1-4}$ alkyl group, halo or a $C_{1-4}$ alkoxy group), a $C_{1-4}$ hydroxyalkyl group, a $C_{2-6}$ alkoxycarbonyl group, nitro, an amino group of formula $NR_{30}R_{31}$ (in which $R_{30}$ and $R_{31}$ independently represent hydrogen or a $C_{1-4}$ alkyl group), a $C_{1-6}$ alkanoyloxy $C_{1-4}$ alkyl group, or an aminomethyl group; with the provisos that when A represents $(CH_2)_2$ and $R_2$, $R_3$, $R_4$, $R_5$, $R_6$, $R_8$, $R_9$ and $R_{10}$ represent hydrogen then $R_1$ does not represent hydrogen or 4-chloro and that when A represents $(CH_2)_5$ and $R_1$, $R_2$, $R_3$, $R_4$, $R_5$, $R_6$, $R_9$ and $R_{10}$ represent hydrogen then $R_8$ does not represent methyl.

It will be understood that a group containing a chain of 3 or more carbon atoms may be straight or branched, for example propyl includes n-propyl and isopropyl and butyl includes n-butyl, sec-butyl, isobutyl and tert-butyl.

In a preferred group of compounds of formula I, $R_1$, $R_2$ and $R_3$ independently represent hydrogen, halo (for example bromo, chloro or fluoro), a $C_{1-4}$ alkyl group (for example methyl, ethyl, propyl or butyl), a $C_{1-4}$ alkoxy group (for example methoxy, ethoxy, propoxy or butoxy), phenoxy, phenyl, a $C_{2-6}$ alkoxycarbonyl group (for example methoxycarbonyl, ethoxycarbonyl, propoxycarbonyl, butoxycarbonyl or pentoxycarbonyl), an amino group of formula —$NR_{13}R_{14}$ in which $R_{13}$ and $R_{14}$ are independently hydrogen or a $C_{1-2}$ alkyl group (for example amino, methylamino, dimethylamino, ethylamino or diethylamino), a polyhalo $C_{1-2}$ alkoxy group (for example trifluoromethoxy or pentafluoroethoxy), a polyhalo $C_{1-2}$ alkyl group (for example trifluoromethyl or pentafluoroethyl), benzyloxy, hydroxy, a ($C_{2-6}$ alkoxycarbonyl) vinyl group; a $C_{2-6}$ alkoxycarbonyl $C_{1-2}$ alkyl group, or $R_1$ and $R_2$ together with the phenyl ring to which they are attached represent a naphthyl group;

$R_4$ and $R_5$ independently represent hydrogen, a $C_{1-4}$ alkyl group (for example methyl, ethyl, propyl or butyl), phenyl, or $R_4$ and $R_5$ together with the carbon atom to which they are attached represent a $C_{3-6}$ cycloalkyl group (for example cyclopropyl, cyclobutyl, cyclopentyl or cyclohexyl);

$R_6$ represents hydrogen or a $C_{1-4}$ alkyl group (for example methyl, ethyl, propyl or butyl);

A represents a $C_{2-7}$ alkylene group which may be straight or branched, (for example ethylene, trimethylene, tetramethylene, 1,1-dimethylethylene, 2,2-dimethylethylene or heptamethylene);

$R_8$ represents hydrogen, a $C_{1-4}$ alkyl group (for example methyl, ethyl, propyl or butyl), phenyl (optionally substituted by a $C_{1-4}$ alkyl group, halo or a $C_{1-4}$ alkoxy group) or benzyl (optionally substituted by a $C_{1-4}$ alkyl group, halo or a $C_{1-4}$ alkoxy group);

$R_9$ and $R_{10}$ independently represent hydrogen, a $C_{1-4}$ alkyl group (for example methyl, ethyl, propyl or butyl), halo (for example bromo, chloro or fluoro), a $C_{1-4}$ hydroxyalkyl group (for example hydroxymethyl, 2-hydroxyethyl or 3-hydroxypropyl), a $C_{2-6}$ alkoxycarbonyl group (for example methoxycarbonyl, ethoxycarbonyl, propoxycarbonyl or butoxycarbonyl), nitro or a $C_{1-6}$ alkanoyloxy $C_{1-2}$ alkyl group (for example formyloxyethyl, acetoxymethyl, propanoyloxymethyl, or butanoyloxymethyl).

One group of more preferred compounds of formula I is represented by formula II

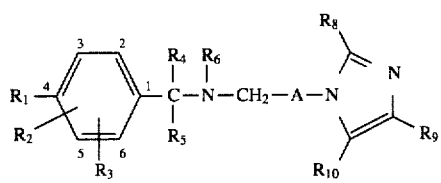

II and pharmaceutically acceptable salts in which $R_1$ represents halo, a $C_{1-4}$ alkyl group, a $C_{2-4}$ alkoxy group, phenoxy, phenyl, a $C_{2-4}$ alkoxycarbonyl group, a perhalo $C_{1-2}$ alkoxy group, a perhalo $C_{1-2}$ alkyl group, benzyloxy, an amino group of formula $NR_{13}R_{14}$ (in which $R_{13}$ and $R_{14}$ independently represent hydrogen or a $C_{1-4}$ alkyl group), a ($C_{2-4}$ alkoxycarbonyl)vinyl group, a $C_{2-6}$ alkoxycarbonyl $C_{1-2}$ alkyl group, or $R_1$ and $R_2$ together with the phenyl ring to which they are attached represent a naphthyl group;

$R_2$ and $R_3$ independently represent hydrogen, halo, a $C_{1-4}$ alkyl group, a $C_{1-4}$ alkoxy group, a perhalo $C_{1-2}$ alkyl group, or hydroxy;

$R_4$ and $R_5$ independently represent hydrogen, a $C_{1-4}$ alkyl group, phenyl or $R_4$ and $R_5$ together with the carbon atom to which they are attached represent a $C_{3-6}$ cycloalkyl group;

$R_6$ represents hydrogen or a $C_{1-3}$ alkyl group;

A represents ethylene, trimethylene, tetramethylene, 1,1-dimethylethylene or heptamethylene;

$R_8$ represents hydrogen, a $C_{1-4}$ alkyl group, phenyl or benzyl;

$R_9$ and $R_{10}$ independently represent hydrogen, a $C_{1-4}$ alkyl group, halo, a $C_{1-4}$ hydroxyalkyl group, a $C_{2-6}$ alkoxycarbonyl group, nitro, or a $C_{1-6}$ alkanoyloxy $C_{1-2}$ alkyl group.

In a preferred group of compound of formula II, $R_1$ represents bromo, chloro, methyl, ethyl, t-butyl, butoxy, phenoxy, phenyl, methoxycarbonyl, ethoxycarbonyl, propoxycarbonyl, dimethylamino, trifluoromethoxy, trifluoromethyl, benzyloxy, 2-ethoxycarbonylvinyl or $R_1$ and $R_2$ together with the phenyl ring to which they are attached represent a naphthyl group. More preferably $R_1$ represents bromo, chloro, t-butyl, butoxy, phenoxy, phenyl, methoxycarbonyl, propoxycarbonyl, trifluoromethoxy, trifluoromethyl, benzyloxy, 2-ethoxycarbonylvinyl or $R_1$ and $R_2$ together with the phenyl ring to which they are attached represent a naphthyl group. Most preferably $R_1$ represents bromo or chloro.

In a preferred group of compounds of formula II, $R_2$ represents hydrogen, 3-chloro, 2-chloro, 3-fluor, 2-methyl, 3-methyl, 2-methoxy, 2-ethoxy, 2-hydroxy or 3-trifluoromethyl and $R_3$ represents hydrogen 2-chloro or 3-chloro. More preferably $R_2$ represents hydrogen, 3-chloro, 2-chloro, 3-fluoro, 2-methyl, 3-methyl, 2-ethoxy, 2-hydroxy or 3-trifluoromethyl and $R_3$ represents hydrogen. Most preferably $R_2$ represents hydrogen or 2-chloro and $R_3$ represents hydrogen.

In a preferred group of compounds of formula II, $R_4$ and $R_5$ independently represent hydrogen, methyl, ethyl or $R_4$ and $R_5$ together with the carbon atom to which they are attached represent a cyclopropyl group. More preferably $R_4$ and $R_5$ both represent hydrogen or methyl. Most preferably $R_4$ and $R_5$ both represent methyl.

In a preferred group of compounds of formula II, $R_6$ represents hydrogen or methyl. More preferably $R_6$ represents hydrogen.

In a preferred group of compounds of formula II, A represents ethylene, trimethylene or tetramethylene. More preferably A represents ethylene or trimethylene.

In a preferred group of compounds of formula II, $R_8$ represents hydrogen, methyl, ethyl, isopropyl, phenyl or benzyl. More preferably $R_8$ represents hydrogen or methyl.

In a preferred group of compounds of formula II, $R_9$ and $R_{10}$ independently represent hydrogen, methyl, chloro, hydroxymethyl, ethoxycarbonyl, nitro or acetoxymethyl.

More preferably $R_9$ and $R_{10}$ independently represent hydrogen, methyl, chloro, acetoxymethyl or ethoxycarbonyl. Most preferably $R_9$ and $R_{10}$ independently represent hydrogen or methyl.

A second group of more preferred compounds of formula I is represented by formula II in which $R_1$, $R_2$ and $R_3$ represent hydrogen, $R_4$ and $R_5$ represent ethyl, $R_6$ represents hydrogen, A represents ethylene, $R_8$ represents hydrogen or $C_{1-4}$ alkyl and $R_9$ and $R_{10}$ independently represent hydrogen, methyl, hydroxymethyl or acetoxymethyl.

A third group of more preferred compounds of formula I is represented by formula II in which $R_1$ represents chloro; $R_2$ represents hydrogen or 3-chloro; $R_3$ represents hydrogen; $R_4$, $R_5$, and $R_6$ each represent hydrogen; A represents ethylene; $R_8$ represents hydrogen or methyl and $R_9$ and $R_{10}$ independently represent hydrogen or methyl.

Specific compounds of formula I are:

N-[1-(4-Chlorophenyl)ethyl]-3-(imidazol-1-yl)propylamine;

N-[1-(2,4-Dichlorophenyl)ethyl]-3-(imidazol-1-yl)propylamine;

N-[1-(3,4-Dichlorophenyl)ethyl]-3-(imidazol-1-yl)propylamine;

N-[1-(4-Fluorophenyl)ethyl]-3-(imidazol-1-yl)propylamine;

N-[1-(4-Benzyloxyphenyl)ethyl]-3-(imidazol-1-yl)propylamine;

N-[1-(4-Dimethylaminophenyl)ethyl]-3-(imidazol-1-yl)propylamine;

N-[1-(3-Chlorophenyl)ethyl]-3-(imidazol-1-yl)propylamine;

N-[1-(2-Chlorophenyl)ethyl]-3-(imidazol-1-yl)propylamine;

N-[1-(4-Chloro-3-trifluoromethylphenyl)ethyl]-3-(imidazol-1-yl)propylamine;

N-[1-(4-Chloro-3-fluorophenyl)ethyl]-3-(imidazol-1-yl)propylamine;

3-(Imidazol-1-yl)-N-[1-(4-trifluoromethylphenyl)ethyl]propylamine;

N-[1-(4-Chloro-3-methylphenyl)ethyl]-3-(imidazol-1-yl)propylamine;

N-[1-(2,3,4-Trichlorophenyl)ethyl]-3-(imidazol-1-yl)propylamine;

N-[1-(4-Bromophenyl)ethyl]-3-(imidazol-1-yl)propylamine;

N-[1-(2,5-Dichlorophenyl)ethyl]-3-(imidazol-1-yl)propylamine;

3-(Imidazol-1-yl)-N-[1-(4-phenoxyphenyl)ethyl]propylamine;

N-[1-(4-Chloro-2-methoxyphenyl)ethyl]-3-(imidazol-1-yl)propylamine;

N-[1-(4-Chloro-2-ethoxyphenyl)ethyl]-3-(imidazol-1-yl)propylamine;

N-[1-(4-Tert-butylphenyl)ethyl]-3-(imidazol-1-yl)propylamine;

Ethyl 4-{1-[3-(imidazol-1-yl)propylamino]ethyl}benzoate;

N-[1-(4-Ethylphenyl)ethyl]-3-(imidazol-1-yl)propylamine;

N-[1-(4-Butoxyphenyl)ethyl]-3-(imidazol-1-yl)propylamine;

3-(Imidazol-1-yl)-N-[1-(4-trifluoromethoxyphenyl)ethyl]propylamine;

N-[1-(4-Chlorophenyl)ethyl]-3-(4,5-dimethylimidazol-1-yl)propylamine;

N-[1-(4-Chlorophenyl)ethyl]-3-(2-phenylimidazol-1-yl)propylamine;

N-[1-(4-Chlorophenyl)ethyl]-4-(imidazol-1-yl)butylamine;

N-[1-(4-Chlorophenyl)ethyl]-3-(2-methylimidazol-1-yl)propylamine;

N-[α-(4-chlorophenyl)benzyl]-3-(imidazol-1-yl)propylamine;

5-Chloro-2-{1-[3-(imidazol-1-yl)propylamino]ethyl}phenol

N-[1-(4-Chlorophenyl)propyl]-3-(imidazol-1-yl)propylamine;

N-[1-(4-Chlorophenyl)ethyl]-3-(2,4-dimethylimidazol-1-yl)propylamine;

3-(2-Benzyl-4-methylimidazol-1-yl)-N-[1-(4-chlorophenyl)ethyl]propylamine;

3-(2-Benzyl-5-methylimidazol-1-yl)-N-[1-(4-chlorophenyl)ethyl]propylamine;

N-[1-(4-Chlorophenyl)ethyl]-3-(4-methyl-2-phenylimidazol-1-yl)propylamine;

N-[1-(4-Chlorophenyl)ethyl]-3-(5-methyl-2-phenylimidazol-1-yl)propylamine;

N-Benzhydryl-3-(imidazol-1-yl)propylamine;

N-(3,4-Dichlorobenzyl)-3-(imidazol-1-yl)propylamine;

N-(4-Bromobenzyl)-3-(imidazol-1-yl)propylamine;

3-(Imidazol-1-yl)-N-(4-trifluoromethylbenzyl)propylamine;

3-(Imidazol-1-yl)-N-(4-phenoxybenzyl)propylamine;

N-(4-Chloro-2-methylbenzyl)-3-(imidazol-1-yl)propylamine;

N-(2,4-Dichlorobenzyl)-3-(imidazol-1-yl)propylamine;

N-(4-Chlorobenzyl)-3-(2-methylimidazol-1-yl)propylamine;

N-(4-Chlorobenzyl)-3-(4-methylimidazol-1-yl)propylamine;

N-(4-Chlorobenzyl)-3-(5-methylimidazol-1-yl)propylamine;

N-(4-Chlorobenzyl)-3-(4,5-dimethylimidazol-1-yl)propylamine;

N-(4-Chlorobenzyl)-4-(imidazol-1-yl)butylamine;

N-(4-Chlorobenzyl)-3-(5-methyl-2-phenylimidazol-1-yl)propylamine;

N-(4-Chlorobenzyl)-3-(4-methyl-2-phenylimidazol-1-yl)propylamine;

Methyl 4-[3-(2-methylimidazol-1-yl)propylaminomethyl]benzoate;

3-(Imidazol-1-yl)-N-(4-methoxy-2,6-dimethylbenzyl)propylamine;

Ethyl 4-[3-(2-methylimidazol-1-yl)propylaminomethyl]cinnamate;

(−)N-[1-(4-Chlorophenyl)ethyl]-3-(imidazol-1-yl)propylamine;

N-[1-(4-Chlorophenyl)ethyl]-3-(2-ethylimidazol-1-yl)propylamine;

N-[1-(4-Chlorophenyl)ethyl]-3-(4-methylimidazol-1-yl)propylamine;

N-[1-(4-Chlorophenyl)ethyl]-3-(5-methylimidazol-1-yl)propylamine;

N-[1-(4-Chlorophenyl)ethyl]-5-(imidazol-1-yl)pentylamine;

(+) N-[1-(4-Chlorophenyl)ethyl]-3-(imidazol-1-yl)propylamine;

N-[1-(4-Chlorophenyl)ethyl]-3-(imidazol-1-yl)-2,2-dimethylpropylamine;

N-[1-(4-Chlorophenyl)-1-methylethyl]-3-(imidazol-1-yl)propylamine;

N-[1-(4-Chlorophenyl)-1-methylethyl]-3-(2-methylimidazol-1-yl)propylamine;

N-(4-Chlorobenzyl)-3-(imidazol-1-yl)-2,2-dimethylpropylamine;

N-[1-(4-Chlorophenyl)-1-methylethyl]-8-(imidazol-1-yl)octylamine;

N-(4-Chlorobenzyl)-3-(4,5-dichloroimidazol-1-yl)propylamine;

N-[1-(4-Chlorophenyl)ethyl]-3-(2-isopropylimidazol-1-yl)propylamine;

N-[1-(4-Chlorophenyl)ethyl]-3-(2,4,5-trimethylimidazol-1-yl)propylamine;

N-[1-(4-Chlorophenyl)ethyl]-3-(4,5-dichloroimidazol-1-yl)propylamine;

N-[1-(4-Chlorophenyl)-1-methylethyl]-3-(4-methylimidazol-1-yl)propylamine;

N-[1-(4-Chlorophenyl)-1-methylethyl]-3-(5-methylimidazol-1-yl)propylamine;

N-[1-(4-Chlorophenyl)-1-methylethyl]-3-(4,5-dimethylimidazol-1-yl)propylamine;

N-(4-Chlorobenzyl)-3-(2-isopropylimidazol-1-yl)propylamine;

N-(4-Chlorobenzyl)-3-(2-ethylimidazol-1-yl)propylamine;

3-(2-Methylimidazol-1-yl)-N-[1-methyl-1-(p-tolyl)ethyl]propylamine;

N-[1-(4-Chlorophenyl)-1-methylethyl]-3-(4-nitroimidazol-1-yl)propylamine;

3-(Imidazol-1-yl)-N-[1-methyl-1-(p-tolyl)ethyl]propylamine;

1-(4-Chlorophenyl)-1-ethyl-3'-(imidazol-1-yl)dipropylamine;

1-{3-[1-(4-Chlorophenyl)-1-methylethylamino]propyl}imidazol-4-yl-methanol;

N-(1-Ethyl-1-phenylpropyl)-3-(imidazol-1-yl)propylamine;

Ethyl 4-{1-[3-(imidazol-1-yl)propylamino]-1-methylethyl}benzoate;

N-[1-(4-Biphenylyl)-1-methylethyl]-3-(imidazol-1-yl)propylamine;

N-[1-(4-Chlorophenyl)cycloprop-1-yl]-3-(imidazol-1-yl)propylamine;

Ethyl 1-{3-[1-(4-chlorophenyl)-1-methylethylamino]propyl}-4-methylimidazole-5-carboxylate;

N-[1-(2-Naphthyl)-1-methylethyl]-3-(imidazol-1-yl)propylamine;

1-{3-[1-(3,4-Dichlorophenyl)-1-methylethylamino]propyl}imidazol-5-ylmethanol;

1-{3-[1-(4-Chlorophenyl)-1-methylethylamino]propyl}imidazol-5-ylmethanol;

1-{3-[1-(4-Biphenylyl)-1-methylethylamino]propyl}imidazol-4-ylmethanol;

1-[3-(1-Ethyl-1-phenylpropylamino)propyl]imidazol-4ylmethanol;

N-[1-(4-Benzyloxyphenyl)-1-methylethyl]-3-(imidazol-1-yl)propylamine;

N-[1-(4-Chlorophenyl)-1-methylethyl]-4-(imidazol-1-yl)butylamine;

N-[1-(4-Chlorophenyl)ethyl]-3-(imidazol-1-yl)-N-methylpropylamine;

N-[1-(4-Chlorophenyl)propyl]-3-(imidazol-1-yl)-N-methylpropylamine;

N-(4-Chlorobenzyl)-3-(2,4-dimethylimidazol-1-yl)propylamine;

3-(2-Benzyl-4-methylimidazol-1-yl)-N-(4-chlorobenzyl)propylamine;

3-(2-Benzyl-5-methylimidazol-1-yl)-N-(4-chlorobenzyl)propylamine;

N-[1-(4-Chlorophenyl)-1-methylethyl]-5-(imidazol-1-yl)pentylamine;

Propyl 4-[3-(2-methylimidazol-1-yl)propylaminomethyl]benzoate;

N-(4-Chlorobenzyl)-5-(2-methylimidazol-1-yl)pentylamine;

N-[1-(4-Chlorophenyl)-1-methylethyl]-3-(imidazol-1-yl)-N-methylpropylamine;

N-(4-Chlorobenzyl)-N-methyl-3-(2-methylimidazol-1-yl)propylamine;

N-[1-(4-Chlorophenyl)-1-methylethyl]-3-(2-isopropylimidazol-1-yl)propylamine;

Propyl 4-{[1-(3-imidazol-1-yl)propylamino]-1-methylethyl}phenylacetate;

1-{3-[1-(4-Chlorophenyl)-1-methylethylamino]propyl}-5-methylimidazol-4-ylmethyl acetate; and 2-(4-{1-[3-(Imidazol-1-yl)propylamino]-1-methylethyl}phenylethanol or pharmaceutically acceptable salts thereof in the form of individual enantiomers, racemates or other mixtures of enantiomers.

The compounds of formula I may form organic or inorganic salts, for example, the compounds of formula I may form acid addition salts with inorganic or organic acids, e.g. hydrochloric acid, hydrobromic acid, fumaric acid, tartaric acid, citric acid, sulphuric acid, hydriodic acid, phosphoric acid, maleic acid, acetic acid, succinic acid, benzoic acid, pamoic acid, palmitic acid, dodecanoic acid and acidic amino acids such as glutamic acid. Some compounds of formula I may form base addition salts, for example, with alkali metals for example sodium hydroxide, or with aminoacids for example, lysine or arginine. It will be appreciated that such salts, provided they are pharmaceutically acceptable may be used in therapy in place of the corresponding compounds of formula I. Such salts are prepared by reacting the compound of formula I with a suitable acid or base in a conventional manner. Such salts may also exist in form of solvates (for example, hydrates).

It will be appreciated by those skilled in the art that certain compounds of formula I contain one or more chiral centres. Thus, compounds of formula I in which $R_4$ and $R_5$ are not identical contain a chiral centre. Certain of the substituents $R_1$, $R_2$, $R_3$, $R_4$, $R_5$, $R_6$, $R_8$, $R_9$ and $R_{10}$ may also contain at least one chiral centre, for example when $R_1$, $R_2$, $R_3$, $R_4$, $R_5$, $R_6$, $R_8$, $R_9$ or $R_{10}$ is sec-butyl.

When a compound of formula I contains a single chiral centre it may exist in two enantiomeric forms. The present invention includes individual enantiomers and mixtures of those enantiomers. The enantiomers may be obtained by methods known to those skilled in the art. Such methods typically include resolution via formation of diastereoisomeric salts or complexes which may be separated, for example, by crystallisation; resolution via formation of diastereoisomeric derivatives or complexes which may be separated, for example, by crystallisation, gas-liquid or liquid chromatography; selective reaction of one enantiomer by reaction with an enantiomer-specific reagent, for example, enzymatic esterification, oxidation or reduction, followed by separation of the modified and unmodified enantiomers; or gas-liquid or liquid chromatography in a chiral environment, for example on a chiral support such as silica with a bound chiral ligand or in the presence of a chiral solvent. It will be appreciated that where the desired enantiomer is converted into another chemical entity by one of the separation processes described above, a further step will subsequently be required to liberate the desired enantiomeric form. Alternatively, specific enantiomers may be synthesised by asymmetric synthesis using optically active reagents, substrates, catalysts or solvents, or by converting one enantiomer into the other by asymmetric transformation.

When a compound of formula I contains more than one chiral centre it may exist in diastereoisomeric forms. The diastereoisomeric pairs may be separated by methods known to those skilled in the art, for example, chromatography or crystallisation and the individual enantiomers within each pair may be separated as described above. The present invention includes each diastereoisomer of compounds of formula I or II and mixtures thereof.

Certain compounds of formula I may exist in more than one crystal form and the present invention includes each crystal form and mixtures thereof. Certain compounds of formula I may also exist in the form of solyates, for example hydrates, and the present invention includes each solvate and mixtures thereof.

The present invention also provides pharmaceutical compositions comprising a therapeutically effective amount of a compound of formula I together with a pharmaceutically acceptable diluent or carrier. Such pharmaceutical formulations may be used in the treatment of inflammatory and/or allergic diseases.

As used hereinafter, the term "active compound" denotes a 1-(arylalkylaminoalkyl)imidazole derivative of formula I. In therapeutic use the active compound may be administered orally, rectally, parenterally, topically, ocularly, aurally, nasally, intravaginally or to the buccal cavity, to give a local and/or a systemic effect. The active compounds may be administered in a prophylactic manner. Thus the therapeutic compositions of the present invention may take the form of any of the known pharmaceutical compositions for such methods of administration. The compositions may be formulated in a manner known to those skilled in the art so as to give a controlled release, for example rapid release or sustained release, of the compounds of the present invention. Pharmaceutically acceptable carriers suitable for use in such compositions are well known in the art of pharmacy. The compositions of the invention suitably contain 0.1–90% by weight of active compound. The compositions of the invention are generally prepared in unit dosage form.

Compositions for oral administration are the preferred compositions of the invention and these are the known pharmaceutical forms for such administration, for example tablets, capsules, granules, syrups and aqueous or oily suspensions. The excipients used in the preparation of these compositions are the excipients known in the pharmacists' art.

Tablets may be prepared from a mixture of the active compound with fillers, for example, lactose or calcium phosphate, disintegrating agents, for example maize starch, lubricating agents, for example magnesium stearate, binders for example microcrystalline cellulose or polyvinyl pyrrolidone and other optional ingredients known in the art to permit tableting the mixture by known methods. The tablets may, if desired, be coated using known methods and excipients which may include enteric coating using for example hydroxypropylmethylcellulose phthalate.

The tablets may be formulated in a manner known to those skilled in the art so as to give a sustained release of the compounds of the present invention. Such tablets may if desired be provided with enteric coatings by known methods, for example by the use of cellulose acetate phthalate.

Similarly capsules, for example hard or soft gelatin capsules containing the active compound with or without added excipients, may be prepared by known methods and, if desired, provided with enteric coatings in a known manner. The contents of the capsule may be formulated using known methods to give sustained release of the active compound. Enteric coated compositions of the invention may be advantageous, depending on the nature of the active compound. The tablets and capsules may conveniently each contain 1–1000 mg (for example 10 mg, 50 mg, 100 mg, 200 mg, 400 mg or 800 mg) of the active compound. Other compositions for oral administration include, for example, aqueous suspensions containing the compound of formula I in an aqueous medium in the presence of a non-toxic suspending agent such as sodium carboxymethylcellulose, and oily suspensions containing a compound of the present invention in a suitable vegetable oil, for example sunflower oil.

The active compound may be formulated into granules with or without additional excipients. The granules may be ingested directly by the patient or they may be added to a suitable liquid carrier (for example water) before ingestion. The granules may contain disintegrants (for example a pharmaceutically acceptable effervescent couple formed from an acid and a carbonate or bicarbonate salt) to facilitate dispersion in the liquid medium.

Compositions of the invention suitable for rectal administration are the known pharmaceutical forms for such adminstration, for example suppositories with hard fat, semi-synthetic glycerides or polyethylene glycol bases.

Compositions of the invention suitable for parenteral administration are the known pharmaceutical forms for such administration, for example sterile suspensions in aqueous and oily media or sterile solutions in a suitable solvent.

Compositions for topical administration may comprise a matrix in which the active compound is dispersed so that it is held in contact with the skin in order to administer the compound of formula I transdermally. Alternatively the active compound may be dispersed in a cream, gel or ointment base or applied in the form of a spray.

Compositions of the invention suitable for inhalation via the mouth and/or the nose are the known pharmaceutical forms for such administration, for example aerosols, nebulised solutions or powders. Metered dose systems, known to those skilled in the art, may be used.

Compositions suitable for application to the buccal cavity include slow dissolving tablets, troches, chewing gum, gels, pastes, powders, mouthwashes or rinses.

The compounds of the present invention may also be administered by continuous infusion either from an external source, for example by intravenous infusion or from a source of the compound placed within the body. Internal sources include implanted reservoirs containing the compound to be infused which is continuously released for example by osmosis and implants which may be a) liquid such as an oily solution or suspension of the compound to be infused for example in the form of a very sparingly water-soluble derivative such as a dodecanoate salt or b) solid in the form of an implanted support for example a synthetic resin or waxy material for the compound to be infused. The support may be a single body containing all the compound or a series of several bodies each containing part of the compound to be delivered.

In some formulations it may be beneficial to use the compounds of the present invention in the form of particles of very small size, for example as obtained by fluid energy milling.

In the compositions of the present invention the active compound may, if desired, be associated with other compatible pharmacologically active ingredients, for example;

a) an analgesic (e.g. in treatment of rheumatoid arthritis),
b) a β2 agonist (e.g. in treatment of asthma) and c) a non-sedating antihistamine (e.g. in treatment of other allergic conditions).

The pharmaceutical compositions containing a therapeutically effective amount of a compound of formula I may be used to treat inflammatory and/or allergic conditions in human beings. In such treatment the amount of the compound of formula I administered per day is in the range 0.1 to 3000 mg. Specific compounds which may be incorporated into the compositions of this invention are the novel compounds disclosed above.

The therapeutic activity of compounds of formula I has been demonstrated by means of tests on standard laboratory animals. Such tests include, for example, the oral administration of the compounds to rats in which an inflammatory condition is induced. Thus, compounds of formula I are useful for the treatment of inflammatory conditions in mammals. Whilst the precise amount of active compound administered will depend on a number of factors, for example the age of the patient, the severity of the condition and the past medical history and always lies within the sound discretion of the administering physician, a suitable dose for enteral administration to mammals, including humans, is generally within the range 0.01–80 mg/kg/day, more usually 0.2–40 mg/kg/day given in single or divided doses. For parenteral administration, a suitable dose is generally within the range 0.01–80 mg/kg/day, more usually 0.2–40 mg/kg/day given in single or divided doses or by continuous infusion. Oral administration is preferred.

Compounds of formula I and pharmaceutically acceptable salts thereof are indicated for use in the treatment of inflammatory and/or allergic conditions for example musculoskeletal disorders for example: rheumatoid arthritis, osteoarthritis, systemic lupus erythematosus, muscle trauma, gout, ankylosing spondylitis, tendonitis and bursiris; respiratory disorders for example: asthma and rhinitis; gastrointestinal disorders for example: gastritis, Crohn's disease, ulcerative coliris and other inflammatory diseases of the bowel; diseases of the oral cavity for example: periodontitis and gingivitis; cutaneous disorders for example: psoriasis, urticaria, allergic skin diseases, burns, ocular inflammation and iritis. Compounds of formula I and salts thereof may also be useful as analgesics and/or anti-pyretic agents.

Accordingly, in another aspect, the present invention also includes a method of treating inflammatory and/or allergic conditions comprising the administration of a therapeutically effective amount of a compound of formula I.

While the precise mechanism of action of the compounds of formula I is unknown at present, it is believed that the pharmacological effects arise from the ability of these compounds to inhibit the release of arachidonic acid from phospholipids. Consequently, in a preferred aspect, the present invention provides a method of treating inflammatory and/or allergic conditions comprising the administration of a therapeutically effective amount of an arachidonic acid release inhibitor of formula 1.

In yet another aspect, the present invention provides the use of a compound of formula I in the manufacture of a medicament for use in the treatment of an inflammatory and/or allergic condition.

Processes for the preparation of compounds of formula I will now be described. These processes form a further aspect of the present invention.

Compounds of formula I in which $R_5$ and $R_6$ represent hydrogen may be prepared by reducing an imine of formula III

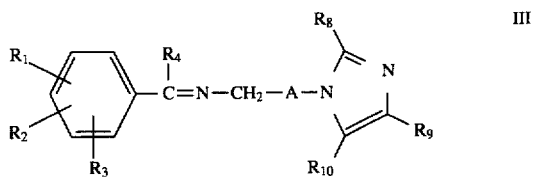

in which $R_1$, $R_2$, $R_3$, $R_4$, $R_8$, $R_9$, $R_{10}$ and A are as previously defined, for example using sodium borohydride, in the presence of an inert organic liquid, preferably a solvent for the compound of formula III, e.g. an alcohol, at a temperature in the range 0°–150° C., at atmospheric pressure.

Compounds of formula III may be prepared by condensing a compound of formula IV

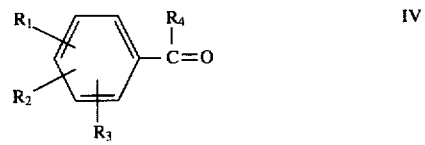

with a compound of formula V

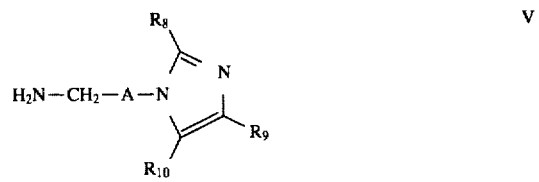

by heating the two compounds at a temperature in the range 0°–200° C. preferably in the range 15°–150° C. optionally in the presence of an inert organic liquid which is preferably a solvent for the reactants.

Compounds of formula I may be prepared in a two-stage, one-pot process by reacting a compound of formula IV with a compound of formula V by heating at a temperature in the range 0°–200° C. and then reducing the intermediate obtained directly for example using sodium borohydride in the presence of an inert organic liquid which is preferably a solvent for the reactants, for example an alcohol, at a temperature in the range 0°–150° C., at atmospheric pressure.

Compounds of formula I may also be prepared in a one stage process by reacting a compound of formula IV with a compound of formula V in the presence of a reducing agent for example sodium cyanoborohydride, in the presence of an inert organic liquid, preferably a solvent for the reactants, e.g. an alcohol, at a temperature in the range 0°–150° C., at atmospheric pressure.

Compounds of formula I in which $R_6$ represents hydrogen may be prepared by reducing an imine of formula VI

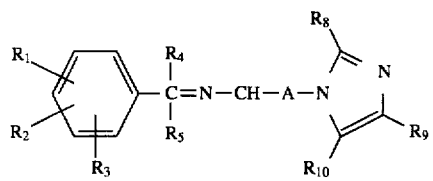

by reaction with a reducing agent, for example sodium borohydride, in the presence of an inert organic liquid which is preferably a solvent for the compounds of formula VI at a temperature in the range 0°–200° C., at atmospheric pressure.

Compounds of formula VI may be prepared by condensing a compound of formula VII

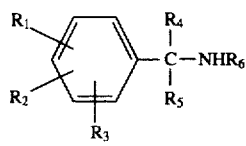

in which $R_6$ represents hydrogen with a compound of formula VIII

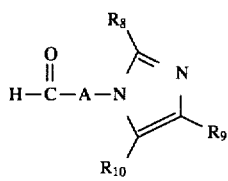

for example by heating the two compounds at a temperature in the range of 0°–200° C. preferably in the range 15°–150° C. optionally in the presence of an inert organic liquid which is preferably a solvent for the reactants e.g. an alcohol, at atmospheric pressure.

Compounds of formula I may be prepared in a two-stage, one-pot process by reacting a compound of formula VII, in which $R_6$ represents hydrogen, with a compound of formula VIII, for example by heating the two compounds at a temperature in the range of 0°–200° C., preferably in the range 15°–150° C., optionally in the presence of an inert organic liquid which is preferably a solvent for the reactants e.g. an alcohol, and then reducing the intermediate obtained directly by reaction with a reducing agent, for example sodium borohydride, in the presence of an inert organic liquid which is preferably a solvent for the reactants, for example an alcohol, at a temperature in the range 0°–150° C., at atmospheric pressure.

Compounds of formula I may be prepared in a one stage process by reacting a compound of formula VII, in which $R_6$ represents hydrogen, with a compound of formula VIII in the presence of a reducing agent, for example sodium cyanoborohydride, in the presence of an inert organic liquid which is preferably a solvent for the reactants, for example an alcohol, at a temperature in the range 0°–150° C., at atmospheric pressure.

Compounds of formula I may be prepared by reacting a compound of formula IX

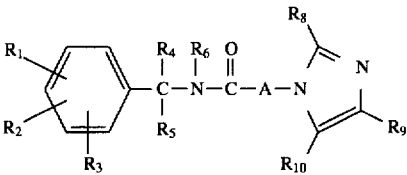

with a reducing agent for example borane or lithium aluminium hydride, optionally in the presence of an inert organic liquid which is preferably a solvent for the compound of formula IX, for example an ether, at a temperature in the range 0°–200° C., preferably 15°–150° C., at atmospheric pressure.

Compounds of formula I, in which $R_4$ and $R_5$ represent hydrogen, may be prepared by reacting a compound of formula X

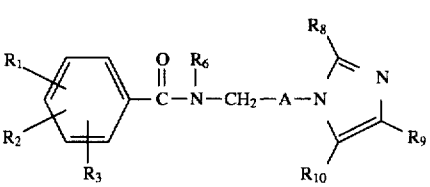

with a reducing agent, for example borane or lithium aluminium hydride, optionally in the presence of an inert organic liquid which is preferably a solvent for the compound of formula X, for example an ether, at a temperature in the range 0°–200° C., preferably 15°–150° C. at atmospheric pressure.

Compounds of formula I may be prepared by reacting a compound of formula XI

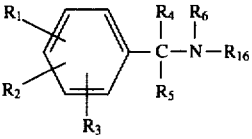

in which $R_{16}$ represents hydrogen with a compound of formula XII

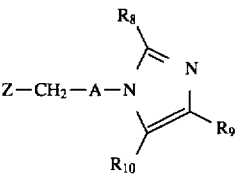

in which Z represents a leaving group for example chloro or bromo, optionally in the presence of a base, e.g. triethylamine, in the presence of an inert organic liquid which is preferably a solvent for the reactants, at a temperature in the range 0°–200° C.

Compounds of formula I in which $R_6$ represents hydrogen may be prepared by reacting a compound of formula XI in which $R_{16}$ represents a hydrolysable acyl group (for example formyl or acetyl) with a compound of formula XII, optionally in the presence of a strong base e.g. sodium hydride, followed by hydrolysis.

Compounds of formula I in which $R_6$ represents hydrogen may be prepared by deprotecting compounds of formula XIII

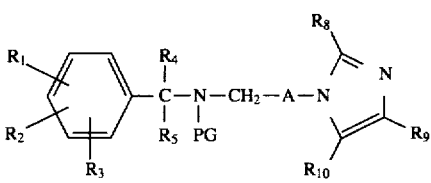
XIII wherein PG represents an amine protecting group. Examples of suitable protecting groups for amines and methods for their addition and removal may be found in the textbook "Protective groups in Organic Synthesis" by T. W. Greene, John Wiley and Sons, 1981, e.g. formyl or acetyl.

Compounds of formula I in which $R_5$ does not represent hydrogen may be prepared by reacting compounds of formula III with compounds of formula $R_5MgX$ or $R_5Li$ in which $R_5$ represents a $C_{1-4}$ alkyl group or a phenyl group (optionally substituted by a $C_{1-4}$ alkyl group, halo or a $C_{1-4}$ alkoxy group) and X represents halo.

Compounds of formula I in which $R_6$ is a $C_{1-4}$ alkyl group may be prepared by alkylation of a corresponding compound of formula I in which $R_6$ is hydrogen, for example using reductive alkylation for example using an aldehyde or a ketone in the presence of a reducing agent for example sodium borohydride.

Compounds of formula I in which $R_6$ represents hydrogen may be prepared by reacting a compound of formula XXIX

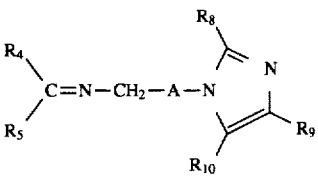
XXIX with a compound of formula XXX

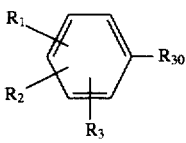
XXX in which $R_{30}$ represents lithium, or a magnesium halide group of formula MgX, in the presence of an organic liquid, which is preferably a solvent for the reactants for example an ether, at a temperature in the range −50° C. to 150° C.

Compounds of formula I may be prepared by reacting a compound of formula XXXI

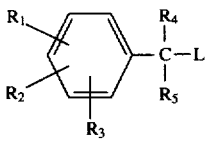
XXXI in which L represents a leaving group for example halo with a compound of formula V, for example by heating, in the presence of an organic liquid which is preferably a solvent for the reactants, at a temperature in the range 0°–150° C. Optionally the compound of formula V may be modified, prior to reaction with XXXI, to promote monoalkylation, for example by protection and then deprotection after the reaction, by methods known to those skilled in the art.

Compounds of formula I in which $R_1$, $R_2$, $R_3$, $R_6$, $R_8$, $R_9$ or $R_{10}$ represents a hydroxyalkyl group may be prepared by reducing a compound of formula I in which $R_1$, $R_2$, $R_3$, $R_6$, $R_8$, $R_9$ or $R_{10}$, respectively, represents an alkoxycarbonyl group or an alkoxycarbonylalkyl group by methods known to those skilled in the art, for example using borane.

Compounds of formula IV are commercially available or may be prepared by methods known to those skilled in the art, for example, those described in Comprehensive Organic Chemistry, Vol. 1, (Edited by J. F. Stoddart) Published by Pergammon Press, 1979.

Compounds of formula V may be prepared by hydrolysis of a compound of formula XIV,

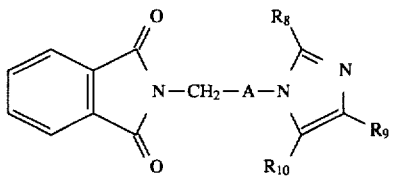
XIV for example in the presence of aqueous hydrochloric acid, or by reacting a compound of formula XIV with hydrazine.

Compounds of formula VII are commercially available or may be prepared by methods known to those skilled in the art, for example, those described in Comprehensive Organic Chemistry, Vol.2, (Edited by I. O. Sutherland) Published by Pergammon Press, 1979. Preferably compounds of formula VII, in which $R_6$ represents hydrogen, may be prepared by rearranging an amide of formula XXV

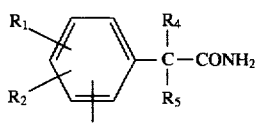
XXV for example by Hofmann rearrangement.

Alternatively compounds of formula VII, in which $R_6$ represents hydrogen, may be prepared by reacting compounds of formula XXVI

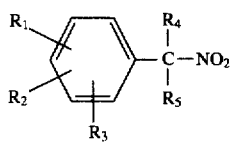
XXVI with a reducing agent, for example hydrogen in the presence of a catalyst or iron in the presence of an acid.

Compounds of formula VIII in which A represents —(CH$_2$)$_2$— may be prepared by reacting acrolein with a compound of formula YH in which Y represents a group of formula XXVII

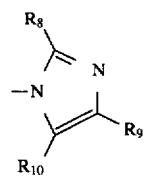
XXVII optionally in the presence of a catalyst, e.g. acetic acid.

Compounds of formula IX may be prepared by reacting a compound of formula XV

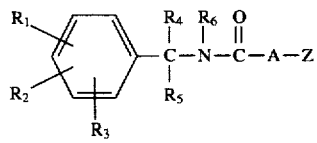
XV in which Z represents a leaving group, for example, halo, preferably bromo or chloro, with a compound of formula YH or $M^+Y^-$ wherein $M^+$ represents an alkali metal cation and $Y^-$ represents an anion derived from a compound of formula YH wherein Y represents a group of formula XXVII as previously defined, for example by heating.

Compounds of formula IX in which A represents —(CH$_2$)$_2$— may be prepared by the reaction of a compound of formula XVI

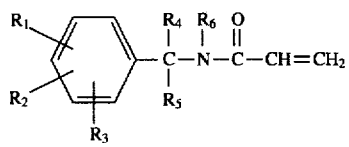

with a compound of formula YH in which Y represents a group of formula XXVII as defined previously in the presence of a catalyst (e.g. N-benzyltrimethylammonium hydroxide) and optionally in the presence of an organic liquid which is preferably a solvent for the starting materials for example pyridine or 1,4-dioxane, at a temperature in the range 50°–200° C., preferably 80°–150° C.

Compounds of formula IX may be prepared by reacting a compound of formula XVII

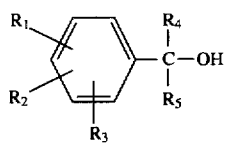

with a compound of formula NC—A—Y, in which Y represents a group of formula XXVII, for example in the presence of a strong acid, e.g. sulphuric acid. Compounds of formula NC—A—Y may be prepared by methods known to those skilled in the art.

Compounds of formula IX may be prepared by reacting a compound of formula VII with a compound of formula X.CO.A.Y, in which X represents a leaving group for example chloro and Y represents a group of formula XXVII, optionally in the presence of a base, for example triethylamine. Compounds of formula X.CO.A.Y may be prepared by methods known to those skilled in the art.

Compounds of formula X may be prepared by reacting compounds of formula XVIII

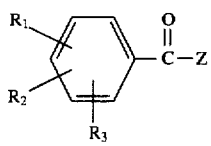

wherein Z is a leaving group, for example halo, preferably chloro, with a compound of formula R$_6$—NH—CH$_2$—A—Y which may be prepared from compounds of formula V by methods known to those skilled in the art.

Compounds of formula XI and XII may be prepared by methods known to those skilled in the art.

Compounds of formula XIII may be prepared by reacting a compound of formula XIX

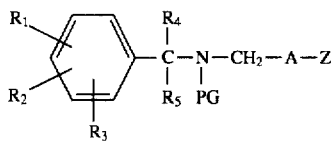

in which Z represents a leaving group (for example halo) with a compound of formula YH or of formula M$^+$Y$^-$ as defined previously, for example by heating.

Compounds of formula XIII may be prepared by reacting a compound of formula XX

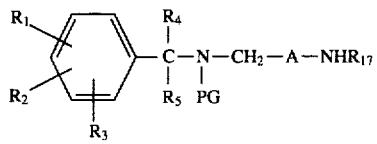

in which R$_{17}$ represents hydrogen or formyl with an imidazole-forming synthon, for example as described in Advances in Heterocyclic Chemistry, Vol.12, 103 (1970) published by Academic Press.

Compounds of formula XIII, in which either R$_4$ or R$_5$ represent a group other than hydrogen, may be prepared by reacting a compound of formula XIII in which PG represents an activating protecting group (for example a hindered acyl group or a formamidine) and R$_4$ or R$_5$ represents hydrogen, respectively, with a reagent of formula R$_4$—Z, or R$_5$—Z respectively, in which Z represents a leaving group (for example halo), in the presence of a base, for example n-butyllithium or sodium hydride.

Compounds of formula XIII, in which both R$_4$ and R$_5$ represent a group other than hydrogen and are different, may be prepared by sequential reaction of a compound of formula XIII, in which PG represents an activating protecting group (for example a hindered acyl group or a formamidine) and both R$_4$ and R$_5$ represent hydrogen, with a reagent of formula R$_4$—Z and then with a reagent of formula R$_5$—Z or vice-versa, in the presence of a base, for example n-butyllithium.

Compounds of formula XIII, in which R$_4$ and R$_5$ are identical and do not represent hydrogen, may be prepared by reacting a compound of formula XIII in which PG represents an activating protecting group (for example a hindered acyl group or a formamidine) and R$_4$ and R$_5$ both represent hydrogen, with a compound of formula R$_4$—Z in the presence of a base, for example of n-butyllithium or sodium hydride. Preferably at least two moles of R$_4$—Z and of the base are used.

Compounds of formula XIII may be prepared by reacting a compound of formula XXIII

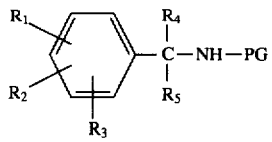

with a compound of formula X—CH$_2$—A—Y in which X represents a leaving group for example halo, and Y represents a group of formula XXVII. Compounds of formula XIII may be prepared by reacting a compound of formula XXIII with a compound of formula X—CO—A—Y followed by reduction. Compounds of formula X—CH$_2$—A—Y and X—CO—A—Y may be prepared by methods known to those skilled in the art.

Compounds of formula XIV may be prepared by reacting a compound of formula XXI

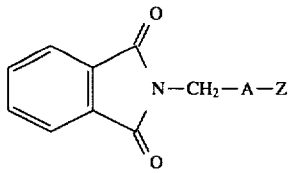

in which Z is a leaving group for example halo, preferably chloro or bromo with a compound of formula YH or of formula M⁺Y⁻.

Compounds of formula XV may be prepared by reacting a compound of formula VII with an acyl halide of formula X.CO.A.Z in which Z is a leaving group for example halo, preferably chloro, and X represents a leaving group, for example halo, in the presence of a base, for example triethylamine.

Compounds of formula XVI may be prepared by reacting a compound of formula VII with a compound of formula XXII

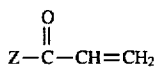

XXII wherein Z is a leaving group for example halo, preferably chloro.

Compounds of formula XIX may be prepared by reacting a compound of formula XXIII with a compound of formula X—CH₂—A—Z in which X represents a leaving group and Z represents a leaving group with the proviso that X is more labile than Z. Compounds of formula X—CH₂—A—Z may be prepared by methods known to those skilled in the art.

Compounds of formula XIX may be prepared by reacting a compound of formula XXIII with a compound of formula X—CO—A—Z followed by reduction. Compounds of formula X—CO—A—Z in which X and Z represent leaving groups for example halo may be prepared by methods known to those skilled in the art.

Compounds of formula XX in which $R_{17}$ represents formyl may be prepared from compounds of formula XX in which $R_{17}$ represents hydrogen by methods known to those skilled in the art.

Compounds of formula XX in which $R_{17}$ represents hydrogen may be prepared by hydrolysis of compounds of formula XXIV

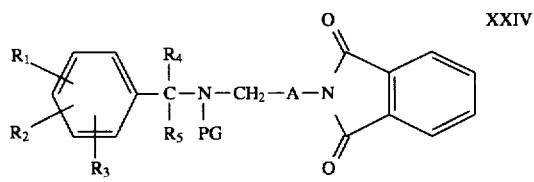

XXIV by methods known to those skilled in the art.

Compounds of formula XXIII may be prepared from compounds of formula VII in which $R_6$ represents hydrogen by methods known to those skilled in the art.

Compounds of formula XXIV may be prepared from a compound of formula XXIII by alkylation methods known to those skilled in the art.

Compounds of formula XXV may be prepared by hydrolysing compounds of formula XXVIII

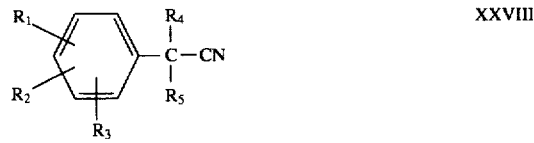

XXVIII for example using a) an acid, or b) a base optionally in the presence of an oxidising agent e.g. hydrogen peroxide.

Compounds of formula XXVI, in which either $R_4$ or $R_5$ represents a group other than hydrogen, may be prepared by reacting a compound of formula XXVI, in which $R_4$ or $R_5$ represents hydrogen, respectively, with a reagent of formula $R_4$—Z, or $R_5$—Z respectively, in which Z represents a leaving group (for example halo), in the presence of a base, for example n-butyllithium or sodium hydride.

Compounds of formula XXVI, in which both $R_4$ and $R_5$ represent a group other than hydrogen and are different, may be prepared by sequential reaction of a compound of formula XXVI, in which both $R_4$ and $R_5$ represent hydrogen, with a reagent of formula $R_4$—Z and then with a reagent of formula $R_5$—Z or vice-versa, in the presence of a base, for example n-butyllithium or sodium hydride.

Compounds of formula XXVI in which $R_4$ and $R_5$ are identical and do not represent hydrogen may be prepared by reacting a compound of formula XXVI in which $R_4$ and $R_5$ both represent hydrogen, with a compound of formula $R_4$—Z in the presence of a base, for example of n-butyllithium or sodium hydride. Preferably at least two moles of $R_4$—Z and of the base are used.

Compounds of formula YH in which Y represents a group of formula XXVII are commercially available or may be prepared by methods known to those skilled in the art.

Compounds of formula XXVIII, in which either $R_4$ or $R_5$ represents a group other than hydrogen, may be prepared by reacting a compound of formula XXVIII, in which $R_4$ or $R_5$ represents hydrogen, respectively, with a reagent of formula $R_4$—Z, or $R_5$—Z respectively, in which Z represents a leaving group (for example halo), in the presence of a base, for example n-butyllithium or sodium hydride.

Compounds of formula XXVIII, in which both $R_4$ and $R_5$ represent a group other than hydrogen, may be prepared by sequential reaction of a compound of formula XXVIII, in which both $R_4$ and $R_5$ represent hydrogen, with a reagent of formula $R_4$—Z and then with a reagent of formula $R_5$—Z or vice-versa, in the presence of a base, for example n-butyllithiumor sodium hydride.

Compounds of formula XXVIII in which $R_4$ and $R_5$ are identical and do not represent hydrogen may be prepared by reacting a compound of formula XXVIII in which $R_4$ and $R_5$ both represent hydrogen, with a compound of formula $R_4$—Z in the presence of a base, for example of n-butyllithium or sodium hydride. Preferably at least two moles of $R_4$—Z and of the base are used.

Compounds of formula XXIX may be prepared by reacting a compound of formula V with a compound of formula XXXII

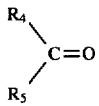

XXXII by methods known to those skilled in the art, for example by heating optionally in the presence of an organic liquid which is preferably a solvent for the reactants at a temperature in the range 0°–150° C., preferably in the presence of a means for removing water, for example a dehydrating agent or a liquid which forms an azeotrope with water.

Compounds of formulae XV, XVII, XVIII, XXI, XXII and XXXI may be prepared by methods known to those skilled in the art.

Certain compounds of formulae IV, V, VI, VII, and VIII are known but it will be apparent to those skilled in the art that the novel compounds may be prepared in a similar manner to the preparation of known compounds of said formulae.

Certain of the intermediate compounds of formulae III, IV, V, VI, VII, VIII, IX, X, XI, XII and XIII are believed to be novel compounds. All novel compounds herein are claimed as a further aspect of the invention.

The compounds of formula I are antiinflammatory agents and may show therapeutic activity at a dose of 200 mg/kg or lower in standard laboratory animals. The therapeutic activity of compounds of formula I has been demonstrated by one or both of the following tests A and B.

Test A was carried out in the following way:
Inhibition of Arachidonic Acid Release from Zymosan Stimulated Macrophaqes Female MF1 mice (weighing 20 to 25 g) were killed using a rising concentration of $CO_2$. The mice were laid on their backs and the abdomens wiped with 70% alcohol. The skin was pulled back, exposing the peritoneal wall. Medium A (5 ml) (see below) was injected into the peritoneal cavity of each mouse followed by approximately 1 ml of air using a 20 ml syringe and a 21 G×40 mm needle in order to form a suspension of macrophage cells. The medium and cells were then removed using a 19 G×40 mm needle. The resulting suspension was returned to a sterile beaker kept on ice. The extracts from all the mice were pooled and this pooled cell suspension was counted using a Coulter counter and adjusted to a final cell count of $1-1.3 \times 10^6$ cells/ml prior to labelling with [$^3$H]-arachidonic acid. Typically five mice provided sufficient cells for each multiwell plate.

Sufficient [$^3$H]-arachidonic acid in ethanol to give a final concentration of 1.6 μCi/ml (equivalent to 40 μCi/plate) was blown to dryness under nitrogen. The arachidonic acid was then resuspended in 1 or 2 ml of the cell suspension which was then mixed with the remainder of the cell suspension in a centrifuge bottle. The labelled cell suspension was then plated out into sterile plastic 96 flat-bottomed well plates (250 μl per well) and incubated overnight at 37° C. in a moist atmosphere of 5% $CO_2$, 95% air.

The following day, non-adherent cells were removed by washing 3 times with sterile phosphate buffered saline (PBS). The adherent peritoneal macrophages were then cultured for a further 24 hours in the presence or absence of drugs, in medium B (see below) at 37° in a 5% $CO_2$ atmosphere in order to measure the effects of drugs on the spontaneous release of arachidonic acid in the absence of stimulus. After this incubation, supernatants were removed to give media 1 and stored in sealed multi-well plates at 4° C. prior to scintillation counting. Drugs which potentiated spontaneous release of arachidonic acid (125% of controls) were deemed to be toxic at the concentration at which this phenomenon occurred. The supernatants were replaced by fresh medium C containing fresh drug and a stimulus. Three drugs were tested at six concentrations (100, 50, 20, 10, 5 and 1 μM) in replicates of four on each plate. The other wells contained controls consisting of a positive control (e.g. dexamethasone), medium (B) only and medium C only.

Incubation was then continued for a further 5 hours, whereupon the supernatants were collected to give media 2 and the adherent cells washed with PBS. The cells were then lysed with 100 μl of 0.1% TRITON® X100 in a 0.1% solution of bovine serum albumin in 0.9% saline and mechanically disrupted to give cell lysates. These supernatants (media 2) and cell lysates (Cells) were also stored in sealed multi-well plates at 4° C. prior to scintillation counting. 200 μl aliquots of media, or 100 μl aliquots of cells were counted using 2 ml of OPTIPHASE "HIGH SAFE" (Trademark of LKB) as scintillant.
Calculation of results The percentage of arachidonic acid released was calculated using the mean values for each group of 4 wells in the following equation.

$$\% \text{ Release} = \frac{\text{cpm in media 2}}{\text{cpm in media 2} + \text{cpm in cell lysate}} \times 100$$

cpm=counts per minute

The value for the arachidonic acid release in the absence of stimulus (spontaneous, cpm of media 2) from cells which had been exposed to neither stimulus nor drug was subtracted from all equivalent values (cpm media 2, stimulated with or without drug) to give the net stimulated release. The percentage inhibition of arachidonic acid release caused by a drug may then be calculated using the following equation.

$$\% \text{ Inhibition} = 100 - \frac{\text{net stimulated release in presence of drug} \times 100}{\text{net stimulated release in absence of drug}}$$

Compounds of formula I were tested at six concentrations (100, 50, 20, 10, 5 and 1 μM) and $IC_{50}$ values calculated. Compounds with $IC_{50}$ values <100 μM are considered to be active. Advantageous compounds have an $IC_{50}$ value <50 μM.

Medium A (for peritoneal lavage)

To a sterile 100 ml measuring cylinder was added: 40 ml $TC_{199}$ with Earle's salts (tenfold concentrate) (ICN); 4 ml heat inactivated swine serum (ICN); 10 ml sodium bicarbonate (7.5% in sterile water); 0.4 ml antibiotics solution (60 mg/ml benzylpenicillin+100 mg/ml streptomycin) and 0.72 ml heparin (5000 U/ml). This mixture was transferred to sterile flask and made up to 400 ml with sterile water.
Medium B (for cell culture)

To a sterile 250 ml measuring cylinder was added: 65 ml TC 199 (tenfold concentrate) with Earle's salts (ICN); 6.5 ml heat inactivated swine serum; 16.25 ml sodium bicarbonate (7.5% in sterile water); 0.65 ml antibiotics solution as above and 65 mg glutamine. This mixture was transferred to a sterile beaker and made up to 650 ml with sterile water.
Medium C=medium B+stimulant (zymosan)

The zymosan stimulant was prepared as follows: zymosan (200 mg) (supplied by Sigma) was added to PBS (20 ml). The mixture was boiled for 30 minutes and the volume restored to 20 ml with water. The zymosan was harvested by centrifugation at 500 Xg for 5 minutes, washed twice by resuspension in PBS (10 ml) and centrifugation. After the final separation, the zymosan was resuspended in 20 ml PBS and stored as 1ml aliquots at −20° C.

650 ml medium B containing 15 ml zymosan=12.5 particles per cell was made up and then stored in 3 ml aliquots in freezer.

Test B was carried out in the following way:
Carrageenan-induced rat paw oedema test Female rats, weight range 125–150 g were fasted overnight. One of the hind legs of each animal was marked with a line at the connection between the cuboid/navicular and calcaneus/talus bones. Groups of six rats were orally dosed at 10 ml/kg, in random order, with a given dose of the test compound given as a solution or suspension in 10% (w/v) aqueous acacia solution.

One hour after dosing, 0.1 ml of 1% (w/v) sterile carrageenan λ in normal saline was injected deeply into the plantar surface of the marked hind foot of each rat. The volume of the foot (up to the marked line) was measured immediately after injection using duplicate water displacement readings. Three hours after injection the foot volume was measured again and the percentage increase in foot volume relative to the initial reading was calculated.

The increase in foot volume (i.e. the degree of oedema) in drug treated animals when compared with that in the drug untreated control gave the degree of inhibition of paw oedema by the drug.

Compounds were considered to be active in this test if they produced a 20% or greater inhibition of paw oedema in at least two out of three tests after oral dosing at 100 mg/kg. Statistical significance was assessed using the Student't test for single dose studies and Dunnett's test for multiple dose studies. More advantageous compounds were active in both Tests A and B,

TABLE 1

| Final product of Example | Test A IC$_{50}$ μM | Test B % inhibition at 100 mg/kg |
|---|---|---|
| 1 | 55 | 59 |
| 2 | 39 | 37 |
| 3 | 60 | — |
| 4 | 95 | — |
| 5 | 12 | 5 |
| 6 | 92 | — |
| 7 | 94 | 48 |
| 8 | 92 | 55 |
| 9 | 22 | 78 |
| 10 | 40 | 49 |
| 11 | 45 | 34 |
| 12 | 36 | — |
| 13 | 13 | 70 |
| 14 | 60 | 60 |
| 15 | 72 | — |
| 16 | 8 | 9 |
| 17 | 90 | — |
| 18 | 50 | — |
| 19 | 12 | 27 |
| 20 | 70 | — |
| 21 | 65 | — |
| 22 | 21 | 17 |
| 23 | 22 | — |
| 24 | 11 | 34 |
| 25 | 19 | 34 |
| 26 | 56 | 40 |
| 27 & 52 | 8 | 27 |
| 28 | 11 | 48 |
| 29 | 34 | 36 |
| 30 | 24 | 39 |
| 31 | 10 | 25 |
| 32 | 6 | 35 |
| 33 | 10 | 2 |
| 34 | 32 | 47 |
| 35 | 21 | 47 |
| 36 | 90 | — |
| 37 | 75 | — |
| 38 | 80 | — |
| 39 | 10 | 35 |
| 40 | 50 | 31 |
| 41 | 58 | 29 |
| 42 | 8 | — |
| 43 | 49 | 33 |
| 44 | 30 | 8 |
| 45 | 8 | 6 |
| 46 | 86 | — |
| 47 | 7 | 35 |
| 48 | 15 | — |
| 49 | 45 | 0 |
| 50 | 31 | 0 |
| 51 | 20 | 1 |
| 53 | 31 | 27 |
| 54 | 12 | 63 |
| 55 | 32 | 45 |
| 56 & 93 | 16 | 57 |
| 57 & 92 | 20 | 48 |
| 58 | 55 | 79 |
| 59 & 68 (1) | 35 | 65 |
| 60 | 9 | 59 |
| 61 | 70 | — |
| 62 | 21 | 42 |
| 63 | 7 | — |
| 64 | 18 | 30 |
| 65 | 18 | 27 |

TABLE 1-continued

| Final product of Example | Test A IC$_{50}$ μM | Test B % inhibition at 100 mg/kg |
|---|---|---|
| 66 | 13 | 13 |
| 67 | 18 | 42 |
| 68 (2) | 43 | 70 |
| 69 | 11 | — |
| 70 | 11 | 21 |
| 71 | 25 | 10 |
| 72 | 26 | 18 |
| 73 | 49 | 8 |
| 74 | 70 | — |
| 75 | 47 | 42 |
| 76 | 15 | 31 |
| 77 | 82 | 23 |
| 78 | 20 | 7 |
| 79 | 85 | — |
| 80 | 54 | 52 |
| 81 | 14 | — |
| 82 | 16 | 38 |
| 83 | 28 | — |
| 84 | 24 | 19 |
| 85 | 45 | 0 |
| 86 | 78 | — |
| 87 | 12 | — |
| 88 | 60 | 6 |
| 89 | 40 | 51 |
| 90 | 62 | — |
| 91 | 62 | 58 |
| 94 | 20 | — |
| 95 | 4 | — |
| 96 | 75 | — |
| 97 | 60 | — |
| 98 | 45 | 4 |
| 99 | 14 | — |
| 100 | 20 | — |
| 103 | 51 | — |

The most advantageous compounds of formula I were active in Tests A and B and also in the following test. Carrageenan-induced pleurisy in rats was carried out as described by Ackerman et al. J. Pharmacol. Exp. Therap. 1980, 215, 588–595. Migrating leukocytes were harvested by lavage of the thoracic cavity 72h after injection of 0.3 ml 1% λcarrageenan in sterile isotonic saline. Test compounds were administered p.o. at the time of challenge and 24h and 48h thereafter.

Especially advantageous compounds of formula 1 were active in the three tests above and also in the late phase of the following test. Early and late phase bronchoconstriction in guinea-pigs following antigen challenge was determined by a variation of the method described by Hutson et al. Am. Rev. Respir. Dis. 1988, 137, 548–557. Guinea-pigs were sensitised by a single i.p. injection of 10 μg ovalbumin and challenged 15 to 17 days later by exposure to aerosolized antigen (4%) for five minutes, following pretreatment with mepyramine to prevent anaphylaxis. Changes in lung function were determined by whole body plethysmography at various times after challenge. Test compounds were administered p.o. 24h and 2h prior to challenge.

The invention is illustrated by the following non-limitative Examples in which compositions of mixed solvents are given by volume. Novel compounds were characterised by one or more of the following: elemental analysis, nuclear magnetic resonance, infra-red and mass spectroscopy. Temperatures are given in degrees Celsius. The abbreviations HPLC (high performance liquid chromatography), THF (tetrahydrofuran), DMF (dimethylformamide), Amt (Amount), Vol (Volume), Temp (Temperature), Ex (Example), IMS (industrial methylated spirit), c (concentration in grams of sample per 100 ml of solution), s (singlet), d (doublet), t (triplet), br (broad) and m (multipier) have been used in the Examples.

EXAMPLE 1 a) A mixture of 4-chloroacetophenone (15.5 g) and 1-(3-aminopropyl)imidazole (12.5 g) was heated at 110° C. for 16 hours under nitrogen, then cooled to ambient temperature.

b) The reaction mixture was dissolved in absolute ethanol (250 ml), sodium borohydride (7.6 g) was added and the mixture heated under reflux for 7 hours.

c) The solvent was evaporated off and the residue was dissolved in water (220 ml). The aqueous mixture was extracted with ether and the combined extracts were extracted with 5M hydrochloric acid. The combined hydrochloric acid extracts were basified with aqueous sodium hydroxide and then extracted with ether. The combined ether extracts were washed with water, dried and filtered and the filtrate evaporated to give an oil. The oil was dissolved in ether and treated with ethereal hydrogen chloride. A hygroscopic solid was collected by filtration. This solid was suspended in ether and left to stand until the solvent had evaporated. The resulting solid was dried under vacuum at 40° C. to give N-[1-(4-chlorophenyl)ethyl]-3-(imidazol-1-yl)propylamine dihydrochloride, m.p. 182°–183° C.

EXAMPLES 2 to 23

In a similar manner to that described in Example 1, a compound of formula I was prepared by (a) reacting an acetophenone of formula IV in which $R_4$=$CH_3$, with 1-(3-aminopropyl)imidazole (Amine in Table A) and (b) heating the product in ethanol under reflux with sodium borohydride as summarised in Table A below (Example 1 included for comparison). The substituents on the compound of formula IV, $R_1R_2R_3$, are hydrogen unless otherwise stated.

The compounds of formula I prepared in Examples 2 to 6 were as follows:

Ex 2 N-[1-(2,4-Dichlorophenyl)ethyl]-3-(imidazol-1-yl) propylamine, b.p. 155°–165° C. (0.01 mmHg).

Ex 3 N-[1-(3,4-Dichlorophenyl)ethyl]-3-(imidazol-1-yl) propylamine, b.p. 180° C. (0.05 mmHg).

Ex 4 N-[1-(4-Fluorophenyl)ethyl]-3-(imidazol-1-yl)propylamine, b.p. 160° C. (0.05 mmHg).

Ex 5 N-[1-(4-Benzyloxyphenyl)ethyl]-3-(imidazol-1-yl) propylamine, b.p. 200° C. (0.04 mmHg). The oil was triturated with ether to give a solid m.p. 45°–51° C.

Ex 6 N-[1-(4-Dimethylaminophenyl)ethyl]-3-(imidazol-1-yl)-propylamine, b.p. 155°–160° C. (0.05 mmHg).

TABLE A

| | Reaction (a) | | | | | Reaction (b) | | | |
|---|---|---|---|---|---|---|---|---|---|
| | Acetophenone | | Amine | Reaction conditions | | Ethanol | NaBH$_4$ | Reflux | |
| Ex. | $R_1R_2R_3$ | Amt/g | Amt/g | Temp/°C. | Time/h | Vol/ml | Amt/g | Time/h | Notes |
| 1 | 4-Cl | 15.5 | 12.5 | 110 | 16 | 250 | 7.6 | 7 | |
| 2 | 2,4-Cl$_2$ | 8.5 | 5.6 | 140 | 7 | 50 | 3.4 | 18 | (1) |
| 3 | 3,4-Cl$_2$ | 9.5 | 6.3 | 125–30 | 6 | 100 | 3.8 | 16 | (2) |
| 4 | 4-F | 6.9 | 6.3 | 125–30 | 6 | 100 | 3.8 | 16 | (2) |
| 5 | 4-OCH$_2$Ph | 11.3 | 6.3 | 120–5 | 6.5 | 120 | 3.8 | 16 | (2) |
| 6 | 4-N(CH$_3$)$_2$ | 8.2 | 6.3 | 135–40 | 6 | 120 | 3.8 | 16 | (2) |
| 7 | 3-Cl | 7.7 | 6.3 | 105–10 | 6 | 120 | 3.8 | 16 | (2) |
| 8 | 2-Cl | 7.7 | 6.3 | 105–10 | 6 | 120 | 3.8 | 16 | (2) |
| 9 | 3-CF$_3$,4-Cl | 6.7 | 3.8 | 120–25 | 6 | 70 | 2.3 | 16 | (2) |
| 10 | 3-F,4-Cl | 5.0 | 3.6 | 120–25 | 6 | 70 | 2.2 | 16 | |
| 11 | 4-CF$_3$ | 4.7 | 3.1 | 105–110 | 6 | 60 | 1.9 | 16 | (1) |
| 12 | 3-CH$_3$,4-Cl | 8.4 | 6.3 | 105–110 | 6 | 120 | 3.8 | 16 | (1) |
| 13 | 2,3,4-Cl$_3$ | 11.8 | 6.3 | 110 | 4 | 120 | 3.8 | 16 | |
| 14 | 4-Br | 10.0 | 6.3 | 110–20 | 4.5 | 120 | 3.8 | 16 | (2) |
| 15 | 2,5-Cl$_2$ | 10.3 | 6.8 | 105–110 | 5 | 130* | 2.3 | + | (2) |
| 16 | 4-OPh | 7.0 | 4.1 | 120 | 18 | 100 | 2.5 | 6 | (3) |
| 17 | 2-OCH$_3$, 4-Cl | 3.9 | 2.6 | 120 | 6 | 50 | 1.6 | 16 | (3) |
| 18 | 2-OC$_2$H$_5$,4-Cl | 5.0 | 3.2 | 120 | 6 | 70 | 1.9 | 16 | (3) |
| 19 | 4-C(CH$_3$)$_3$ | 2.9 | 2.1 | 120 | 6 | 50 | 1.3 | 16 | (3) |
| 20 | 4-CO$_2$C$_2$H$_5$ | 3.0 | 2.0 | 120 | 6 | 40 | 1.2 | 16 | (3) (4) |
| 21 | 4-C$_2$H$_5$ | 5.9 | 5.0 | 120 | 10 | 100 | 3.0 | 16 | (5) |
| 22 | 4-OC$_4$H$_9$-n | 4.8 | 3.2 | 120 | 12 | 100 | 1.9 | 16 | (5) |
| 23 | 4-OCF$_3$ | 4.0 | 2.5 | 140 | 16 | 50 | 0.8 | 6 | (7) |

*Methanol used.
+ Stirred at 20° C. for 4 hours

Notes (Table A)

(1) The reaction mixture was extracted with dichloromethane. The residue obtained by extraction was dissolved in ether, treated with charcoal, filtered and the filtrate evaporated to give an oil.

(2) As described in Example 1 but the hydrochloride was hygroscopic and was converted back to the free base using sodium hydroxide. The oil obtained was further purified by distillation.

(3) Dichloromethane was used as the extracting solvent. The residue obtained after removal of the dichloromethane was distilled under vacuum.

(4) Reaction (b) was carried out at ambient temperature with stirring and the mixture left standing at this temperature for 64 hours.

(5) The residue obtained, after evaporation of the extracting solvent (ethyl acetate), was dissolved in diethyl ether and treated with an ethereal oxalic acid solution until the mixture was just acidic. The precipitated solid was collected by filtration and dried.

(7) After removal of the ethanol, water (75 ml) and concentrated sodium hydroxide solution (10 ml, 20M) were added. The product was extracted into ethyl acetate. Evaporation of the combined extracts gave an oil (3.9 g) which was dissolved in ether (20 ml) and citric acid (1.9 g) in absolute ethanol (50 ml) was added. The mixture was heated at 95° C. for 5 minutes, then cooled and scratched. The supernatant liquid was decanted from the semi-solid. The semi-solid was triturated with ether and filtered. The residue was immediately placed in a vacuum oven at 60° C. for 24 hours and then dried at 80° C. for 12 hours to give a solid hygroscopic product.

The compounds of formula I prepared in Examples 7 to 23 were as follows:

Ex 7 N-[1-(3-Chlorophenyl)ethyl]-3-(imidazol-1-yl)propylamine, b.p. 180°–185° C. (0.45 mmHg).

Ex 8 N-[1-(2-Chlorophenyl)ethyl]-3-(imidazol-1-yl)propylamine, b.p. 130°–140° C. (0.02 mmHg).

Ex 9 N-[1-(4-Chloro-3-trifluoromethylphenyl)ethyl]-3-(imidazol-1-yl)propylamine, b.p. 142°–6° C. (0.02 mmHg).

Ex 10 N-[1-(4-Chloro-3-fluorophenyl)ethyl]-3-(imidazol-1-yl)propylamine dihydrochloride, m.p. 199°–201° C., after recrystallisation from ethanol.

Ex 11 3-(Imidazol-1-yl)-N-[1-(4-trifluoromethylphenyl)thyl]propylamine, oil not distilled.

Ex 12 N-[1-(4-Chloro-3-methylphenyl)ethyl]-3-(imidazol-1-yl)propylamine, oil not distilled.

Ex 13 N-[1-(2,3,4-Trichlorophenyl)ethyl]-3-(imidazol-1-yl)propylamine dihydrochloride, m.p. 211°–214° C., after trituration with hot propan-2-ol.

Ex 14 N-[1-(4-Bromophenyl)ethyl]-3-(imidazol-1-yl)propylamine, b.p. 153°–158° C. (0.01 mmHg).

Ex 15 N-[1-(2,5-Dichlorophenyl)ethyl]-3-(imidazol-1-yl) propylamine, b.p. 170°–175° C. (0.5 mmHg).

Ex 16 3-(Imidazol-1-yl)-N-[1-(4-phenoxyphenyl)ethyl]propylamine, b.p. 220° C. (0.5 mmHg).

Ex 17 N-[1-(4-Chloro-2-methoxyphenyl)ethyl]-3-(imidazol-1-yl)propylamine, b.p. 180° C. (0.4 mmHg).

Ex 18 N-[1-(4-Chloro-2-ethoxyphenyl)ethyl]-3-(imidazol-1-yl)propylamine, b.p. 185° C. (0.5 mmHg).

Ex 19 N-[1-(4-Tert-butylphenyl)ethyl]-3-(imidazol-1-yl) propylamine, b.p. 130°–140° C. (0.01 mmHg).

Ex 20 Ethyl 4-{1-[3-(imidazol-1-yl)propylamino] ethyl}benzoate, b.p. 180° C. (0.1 mm).

Ex 21 N-[1-(4-Ethylphenyl)ethyl]-3-(imidazol-1-yl)propylamine hemioxalate, m.p. 201°–202° C.

Ex 22 N-[1-(4-Butoxyphenyl)ethyl]-3-(imidazol-1-yl)propylamine dioxalate m.p. 114°–116° C.

Ex 23 3-(Imidazol-1-yl)-N-[1-(4-trifluoromethoxyphenyl) ethyl]propylamine sesquicitrate, m.p. 143°–149° C.

In a similar manner to that described in Example 1, an amine of formula V in which A represents a group of formula $(CH_2)_n$ was reacted with 4'-chloroacetophenone (Ketone) as summarised in Table B. The substituents on the compound of formula V, $R_8R_9R_{10}$, are hydrogen unless otherwise stated in Table B. The value of n is indicated in Table B.

TABLE B

| | | Reaction (a) | | | | | Reaction (b) | | | |
|---|---|---|---|---|---|---|---|---|---|---|
| | Amine | | Ketone | | | | Ethanol | NaBH$_4$ | Reflux | |
| Ex. | R$_8$R$_9$R$_{10}$ | n | Amt/g | Amt/g | Temp/°C. | Time/h | Vol/ml | Amt/g | Time/h | Notes |
| 24 | 4,5-(CH$_3$)$_2$ | 2 | 2.1 | 2.1 | 110–15 | 5 | 50 | 1.0 | 16 | |
| 25 | 2-C$_6$H$_5$ | 2 | 4.0 | 3.1 | 130–5 | 5 | 50 | 1.5 | 16 | (1) |
| 26 | — | 3 | 3.7 | 4.1 | 120–5 | 6 | 65 | 2.1 | 16 | (2) |
| 27 | 2-CH$_3$ | 2 | 10.0 | 11.1 | 105–10 | 5.5 | 170 | 5.5 | 16 | |

Notes
(1) Ethyl acetate was used as the extracting solvent. The residue obtained after evaporation of this solvent was distilled, b.p. 185–190° C. (0.06 mmHg). This oil was treated as in Example 1 to give the dihydrochloride.
(2) The oil obtained after extraction was distilled under vacuum.

The compounds of formula I prepared in Examples 24 to 27 were as follows

Ex 24 N-[1-(4-Chlorophenyl)ethyl]-3-(4,5-dimethylimidazol-1-yl)propylamine dihydrochloride, m.p. 205°–207° C., after trituration with propan-2-ol and ether.

Ex 25 N-[1-(4-Chlorophenyl)ethyl]-3-(2-phenylimidazol-1-yl)propylamine dihydrochloride hydrate, m.p. <100° C. (hygroscopic).

Ex 26 N-[1-(4-Chlorophenyl)ethyl]-4-(imidazol-1-yl)butylamine, b.p. 180°–185° C. (0.4 mmHg).

Ex 27 N-[1-(4-Chlorophenyl)ethyl]-3-(2-methylimidazol-1-yl)propylamine dihydrochloride, m.p. 239°–241° C.

EXAMPLE 28

In a similar manner to Example 1, a mixture of 4-chlorobenzophenone (8.0 g) and 1-(3-aminopropyl)imidazole (4.6 g) was heated at 130° C. for 12 hours. The mixture was cooled, dissolved in absolute ethanol (100 ml), treated with sodium borohydride (2.8 g) and the mixture boiled under reflux for 8 hours. The oil obtained after work-up, using dichloromethane as the extracting solvent, was distilled to give N-[α-(4-chlorophenyl)benzyl]-3-(imidazol-1-yl)propylamine, b.p. 240° C. (0.3 mmHg).

EXAMPLE 29 a) Concentrated sulphuric acid (5 drops) was added cautiously to a stirred mixture of 3-chlorophenol (74 g) and acetic anhydride (64.6 g) at ambient temperature. The mixture was left to stand for 18 hours and then added to water (300 ml). The mixture was extracted with dichloromethane and the combined extracts washed with sodium bicarbonate solution, dried and evaporated under reduced pressure. The oil obtained was distilled under vacuum to give 3-chlorophenyl acetate b.p. 116°–118° C. (2 mmHg).

b) The acetate from (a) (74 g) was mixed with anhydrous aluminium chloride (85 g) and heated to 150° C. for 2 hours. The mixture was cooled, quenched with a mixture of ice and 5M hydrochloric acid and steam distilled. The distillate was extracted with diethyl ether to give 4'-chloro-2'-hydroxyacetophenone as an oil which was used directly in part (c) below.

c) The acetophenone (3.3 g) from (b) and 1-(3-aminopropyl)imidazole (7.1 g) were dissolved in methanol (30 ml). Saturated methanolic hydrogen chloride (3 ml) was added to this solution, followed by sodium cyanoborohydride (0.84 g). The resulting mixture was stirred at ambient temperature for 48 hours and then left standing for 64 hours. Concentrated hydrochloric acid (6 ml) and water (30 ml) were added and the mixture stirred for 10 minutes. The mixture was diluted with water, washed with dichloromethane, basified with 5M sodium hydroxide solution and then extracted with dichloromethane. The combined extracts were dried and evaporated to give an oil which was dissolved in diethyl ether and acidified with ethereal hydrogen chloride. The solid obtained was collected by filtration and dried under vacuum to give 5-chloro-2-{1-[3-(imidazol-1-yl)propylamino]ethyl}phenol dihydrochloride, m.p. >300° C.

EXAMPLE 30

In a similar manner to Example 1, a mixture of 4'-chloropropiophenone (8.4 g) and 1-(3-aminopropyl)imidazole (6.3 g) was heated at 120° C. for 9 hours. The cooled mixture was dissolved in absolute ethanol (100 ml), treated with sodium borohydride (3.9 g) and boiled under reflux for 16 hours. The oil obtained after work-up was dissolved in ether and treated with ethereal oxalic acid until the mixture was just acidic. The solid was filtered off and recrystallised from ethanol to give N-[1-(4-chlorophenyl)propyl]-3-(imidazol-1-yl)propylamine oxalate, m.p. 189°–190° C.

EXAMPLE 31

In a similar manner to Example 1, a mixture of 4'-chloroacetophenone (4.0 g) and 1-(3-aminopropyl)-2,4-dimethylimidazole (4.0 g) was heated at 115°–120° C. for 7 hours then reduced with sodium borohydride (2.0 g) in ethanol (70 ml) over 18 hours. The solid obtained was triturated with propan-2-ol and filtered to give N-[1-(4-chlorophenyl) ethyl]- 3-(2,4-dimethylimidazol-1-yl)propylamine dihydrochloride, m.p. 218°–220° C.

EXAMPLE 32

In a similar manner to Example 3, a mixture of 4'-chloroacetophenone (7.9 g) and 3-(2-benzyl-4-methyl-imidazol-1-yl)propylamine (11.7 g) was heated at 120°–130° C. for 6 hours and then reduced with sodium borohydride (2.0 g) in IMS (200 ml) over 16 hours. The product obtained was 3-[2-benzyl-4-methylimidazol-1-yl]-N-[1-(4-chlorophenyl) ethyl]propylamine, b.p. 185°–195° C. (0.04 mmHg). The product contained 12.7% of 3-(2benzyl-5-methylimidazo-1-yl)-N-[1-(4-chlorophenyl)ethyl]propylamine by glc.

EXAMPLE 33

A mixture of 3-(4-methyl-2-phenylimidazol-1-yl)propylamine (5.3 g) and 4'-chloroacetophenone (3.8 g) was heated at 120°–125° C. for 7 hours. On cooling, the oil was dissolved in absolute alcohol (70 ml) and, after the addition of sodium borohydride (7.0 g), the mixture was boiled under reflux for 16 hours. Work-up as described in Example 3 gave an oil which was distilled at 185°–205° C. (0.06 mmHg). The main fraction was redistilled to give N-[1-(4-chlorophenyl)ethyl]-3-(4-methyl-2-phenyl-imidazol-1-yl)propylamine, b.p. 205° C. (0.04 mmHg). Glc indicated the presence of 14% of N-[1-(4-chlorophenyl)-ethyl]-3(5-methyl-2-phenylimidazol-1-yl)propylamine.

EXAMPLE 34

In a similar manner to Example 1, benzophenone (10.0 g) and 1-(3-aminopropyl)imidazole (6.9 g) gave N-benzhydryl- 3-(imidazol-1-yl)propylamine dihydrochloride, m.p. 243°–244° C.

EXAMPLE 35 a) 1-(3-Aminopropyl)imidazole (6.3 g) was added to a stirred solution of 3,4-dichlorobenzaldehyde (8.75 g) in absolute ethanol (100 ml) at ambient temperature under nitrogen and the mixture stirred for a further 6 hours.

b) Sodium borohydride (1.9 g) was added and the mixture boiled under reflux for 16 hours. The mixture was evaporated to dryness under reduced pressure and the residue dissolved in water (approx. 100 ml). The solution was extracted with ethyl acetate (3×100 ml) and the combined extracts washed with 5M hydrochloric acid (2×100 ml). The combined acid washes were basified with 10M sodium hydroxide, with cooling in ice, and the product was back extracted into ethyl acetate (3×100 ml). The combined extracts were washed with water (100 ml), dried over magnesium sulphate and evaporated to give N-(3,4-dichlorobenzyl)-3-(imidazol-1-yl)propylamine as an oil, not distilled.

EXAMPLE 36–41

Examples 36–41 were prepared in a similar manner to that described in Example 35 by reacting compounds of formula IV in which $R_4$ represents hydrogen with 3-(imidazol-1-yl)propylamine (Amine) as summarised in Table C. $R_1R_2R_3$ represent hydrogen, unless otherwise stated, in Table C.

Ex 36 N-(4-Bromobenzyl)-3-(imidazol-1-yl)propylamine, b.p. 185°–200° C. (0.075 mmHg).

Ex 37 3-(Imidazol-1-yl)-N-(4-trifluoromethylbenzyl)propylamine dihydrochloride, m.p. 185°–186° C.

Ex 38 3-(Imidazol-1-yl)-N-(4-trifluoromethoxybenzyl)propylamine dihydrochloride, m.p. 160°–163° C.

Ex 39 3-(Imidazol-1-yl)-N-(4-phenoxybenzyl)propylamine, b.p. 190° C. (0.02 mmHg).

Ex 40 N-(4-Chloro-2-methylbenzyl)-3-(imidazol-1-yl)propylamine dihydrochloride, m.p. 212°–214° C.

Ex 41 N-(2,4-Dichlorobenzyl)-3-(imidazol-1-yl)propylamine, b.p. 140°–150° C. (0.02 mmHg).

TABLE C

| | | Reaction (a) | | | | Reaction (b) | | |
|---|---|---|---|---|---|---|---|---|
| | | Aldehyde | Amine | Ethanol | | NaBH$_4$ | Reflux | |
| Ex. | R$_1$R$_2$R$_3$ | Amt/g | Amt/g | Vol/ml | Time/h | Amt/g | Time/h | Notes |
| 36 | 4-Br | 9.3 | 6.3 | 150 | 18 | 5.0 | 7 | |
| 37 | 4-CF$_3$ | 10.4 | 7.6 | 120 | 6 | 2.3 | 16 | (1) |
| 38 | 4-OCF$_3$ | 2.1 | 1.3 | 35 | 6 | 0.8 | 16 | (1) |

TABLE C-continued

| | Reaction (a) | | | | Reaction (b) | | |
|---|---|---|---|---|---|---|---|
| | Aldehyde | Amine | Ethanol | | NaBH$_4$ | Reflux | |
| Ex. | R$_1$R$_2$R$_3$ Amt/g | Amt/g | Vol/ml | Time/h | Amt/g | Time/h | Notes |
| 39 | 4-OC$_6$H$_5$  2.5 | 1.6 | 35 | 16 | 1.0 | 16 | (2) |
| 40 | 2-CH$_3$,4-Cl  2.1 | 1.7 | 30 | 24 | 1.0 | 6 | (3) |
| 41 | 2,4-Cl$_2$  8.8 | 6.3 | 125 | 16 | 1.9 | 16 | |

Notes on Table C
1. The oil obtained after extraction was dissolved in ether and treated with ethereal hydrogen chloride to give a salt which was collected by filtration.
2. Dichloromethane was used as the extracting solvent.
3. The reaction mixture was extracted with dichloromethane. The dihydrochloride was recrystallised from propan-2-ol.

EXAMPLE 42

In a similar manner to Example 35, a mixture of 4-chlorobenzaldehyde (3.8 g) and 1-(3-aminopropyl)-2,4-dimethylimidazole (4.1 g) in ethanol (70 ml) was stirred and then reduced with sodium borohydride (2.0 g). The hydrochloride salt was triturated with propan-2-ol, filtered and the residue washed with ether, then dried under vacuum at 45° C., to give N-(4-chlorobenzyl)-3-(2,4-dimethylimidazol-1-yl)propylamine dihydrochloride, m.p. 208°–210° C.

EXAMPLE 43–46

In a similar manner to that described in Example 35, amines of formula V in which A represents (CH$_2$)$_n$ were reacted with 4-chlorobenzaldehyde (Aldehyde) to give compounds of formula I as summarised in Table D below. R$_8$R$_9$R$_{10}$ represent hydrogen unless otherwise stated in Table D.

TABLE D

| | Reaction (a) | | | | | Reaction (b) | | |
|---|---|---|---|---|---|---|---|---|
| | Amine | | | Aldehyde | Ethanol | | NaBH4 | Reflux | |
| Ex. | R$_8$R$_9$R$_{10}$ | n | Amt/g | Amt/g | Vol/ml | Time/h | Amt/g | Time/h | Notes |
| 43 | 2-CH$_3$ | 2 | 2.8 | 2.8 | 30 | 6 | 1.5 | 16 | |
| 44 | 4-CH$_3$ | 2 | 13.6 | 13.7 | 150 | 6 | 7.4 | 16 | (1) |
| 44 | 4,5-(CH$_3$)$_2$ | 2 | 1.9 | 1.9 | 19 | 16 | 0.6 | 6 | |
| 45 | H | 3 | 3.7 | 3.7 | 70 | 6 | 2.0 | 16 | |

Notes
1) The starting amine was a mixture of the 4-methyl and 5-methyl isomers (See Preparation of Starting Materials). The product was crystallised three times from ethanol and the structure assigned by $^1$H and $^{13}$C nmr spectroscopy after comparison with reference compounds [see Arch. Pharm. 308 795 (1975)].

The compounds of formula I prepared in Examples 43–46 were as follows;
Ex 43 N-(4-Chlorobenzyl)-3-(2-methylimidazol-1-yl)propylamine, b.p. 150°–155° C. (0.02 mmHg).
Ex 44 N-(4-Chlorobenzyl)-3-(4-methylimidazol-1-yl)propylamine dihydrochloride, m.p. 186°–188° C. (from ethanol).
Ex 45 N-(4-Chlorobenzyl)-3-(4,5-dimethylimidazol-1-yl)propylamine dihydrochloride, m.p. 212°–214° C.
Ex 46 N-(4-Chlorobenzyl)-4-(imidazol-1-yl)butylamine dihydrochloride, m.p. 162°–165° C. (from propan-2-ol).

EXAMPLE 47

In a similar manner to Example 35, a mixture of 4-chlorobenzaldehyde (5.6 g) and 1-(3-aminopropyl)-2-benzyl-4-methylimidazole (9.2 g) in ethanol (100 ml) was stirred and then reduced with sodium borohydride (1.6 g) to give 3-(2-benzyl-4-methylimidazol-1-yl)-[-(4-chlorobenzyl)propylamine, b.p. 190°–200° C. (0.04 mmHg). Glc and $^1$H nmr indicated that the product contained 21% of 3-(2-benzyl-5-methylimidazol-1-yl)-N-(4-chlorobenzyl)propylamine.

EXAMPLE 48

3-(4-Methyl-2-phenylimidazol-1-yl)propylamine (5.5 g) and 4-chlorobenzaldehyde (3.6 g) were stirred in absolute ethanol (70 ml) for 16 hours. Sodium borohydride (2.0 g) was added and the mixture heated under reflux for 7 hours. Work-up as described in Example 42 gave N-(4-chlorobenzyl)-3-(4-methyl-2-phenylimidazol-1-yl)propylamine. Glc indicated that the product contained 13% (approx) of N-(4-chlorobenzyl)-3(5-methl-2-phenylimidazol-1-yl)propylamine.

EXAMPLE 49

In a similar manner to Example 35, methyl 4-formylbenzoate (8.2 g) and 1-(3-aminopropyl)-2-methylimidazole (5.9 g) gave methyl 4-[3-(2-methylimidazol-1-yl)propylaminomethyl]benzoate, as an oil not distilled.

EXAMPLE 50

In a similar manner to Example 37, molar equivalents of 4-methoxy-2,6-dimethylbenzaldehyde and 1-(3-aminopropyl)imidazole gave 3-(imidazol-1-yl)-N-(4-methoxy-2,6-dimethylbenzyl)propylamine dihydrochloride, m.p. 212°–213° C. (from aqueous propan-2-ol).

EXAMPLE 51

4-Formylcinnamic acid (1.76 g) and 1-(3-aminopropyl)-2-methylimidazole (2.78 g) were stirred in methanol (100 ml) for 5 hours at ambient temperature. Sodium borohydride (1.14 g) was added and the mixture stirred for 2 days at ambient temperature. The reaction mixture was evaporated to dryness. The residue was dissolved in water (60 ml) and washed with dichloromethane. The aqueous solution was neutralised with 5M hydrochloric acid and then washed with dichloromethane. The aqueous layer was evaporated to dryness to give crude 4-[3-(2-methylimidazol-1-yl)propylaminomethyl]cinnamic acid which was boiled under reflux in absolute ethanol (50 ml) and concentrated sulphuric acid (1.5 ml) with stirring for 20 hours. The mixture was hot filtered and the residue dissolved in water, basified with 2M sodium hydroxide and extracted into ethyl acetate to yield an oil which was dissolved in ether and treated with ethereal hydrogen chloride. The solid was collected by filtration and recrystallised from propan-2-ol to give ethyl 4-[3-(2-methylimidazol-1-yl)propylaminomethyl]cinnamate dihydrochloride, m.p. 109°–110.5° C.

EXAMPLE 52 a) A mixture of 4'-chloroacetophenone (103.3 g), formamide (98%; 123 g) and formic acid (97%; 8.3 ml) was stirred and heated at 180° C. The water produced in the reaction was removed by distillation together with some of the starting acetophenone which was separated and returned to the reaction vessel. Formic acid (70 ml total) was added in small aliquots over 8 hours. The reaction mixture was cooled and exhaustively extracted with toluene. The combined toluene extracts were washed with water, dried, filtered and the filtrate evaporated. Concentrated hydrochloric acid (70 ml) was added to the residue and the mixture boiled under reflux for 1 hour. The mixture was cooled, extracted with toluene and the aqueous layer basified with aqueous sodium hydroxide (5M). The solution was steam distilled until 1.4 l of distillate had been collected and the distillate was extracted with ethyl acetate. The combined ethyl acetate extracts were dried, filtered and the filtrate evaporated to give an oil which was distilled to give (±)-1-(4-chlorophenyl)ethylamine, b.p. 120°–122° C. (19 mmHg). A small portion of the distillate was dissolved in dry ether and an equal volume of saturated ethereal hydrogen chloride was added. The solid formed was collected by filtration and dried to give (±)-1-(4-chlorophenyl)ethylamine hydrochloride, m.p. 186°–189° C.

b) A solution of 3-chloropropionyl chloride (32.7 g) in methylene chloride (40 ml) was added dropwise to stirred solution of (±) 1-(4-chlorophenyl)ethylamine (40 g) in dichloromethane (260 ml) with triethylamine (28.4 g) over 45 minutes at 0°–5° C. The temperature was allowed to rise to 25° C. and the mixture stirred for a further 2 hours. The cooled reaction mixture was washed with saturated aqueous sodium bicarbonate (260 ml). The organic layer was separated, dried and filtered and the filtrate evaporated. The residue was triturated with petrol, collected by filtration and recrystallised from ethyl acetate to give 3-chloro-N-[1-(4-chlorophenyl)ethyl]propionamide, m.p. 86°–91° C. This product was obtained as a mixture with N-[1-(4-chlorophenyl)ethyl]acrylamide but was sufficiently pure for synthetic purposes. The acrylamide does not react and was removed on work-up in the next stage.

c) A solution of 2-methylimidazole (2.64 g) in dry tetrahydrofuran (THF) (40 ml ) was added over 1 minute to a stirred suspension of sodium hydride (1.54 g; 60% dispersion in oil) in THF (65 ml) under dry nitrogen. The mixture was stirred at ambient temperature for 1 hour, then heated to boiling under reflux and allowed to cool. A solution of 3-chloro-N-[1-(4-chlorophenyl)ethyl]-propionamide (5.7 g) in THF (25 ml) was added and the mixture stirred under reflux for 16 hours. The mixture was cooled and water (100 ml) was added portion-wise with stirring followed by ethyl acetate (200 ml). The acidic layer was separated and extracted with ethyl acetate and the combined ethyl acetate extracts extracted with hydrochloric acid (5M). The combined acidic extracts were basified with concentrated sodium hydroxide solution and extracted with ethyl acetate to give an oil. The oil was triturated with ether and filtered to give N-[1-(4-chlorophenyl)ethyl]-3-(2-methylimidazol-1-yl)propionamide, m.p. 135°–137° C.

d) Borane/THF (1M; 55 ml) was added over 5 minutes to a stirred suspension of the amide prepared in (c) (3.21 g) in dry THF (80 ml) under nitrogen. The mixture was stirred for 5 hours and allowed to stand for 18 hours at ambient temperature. The solvent was removed by evaporation and the residue heated under nitrogen at 100° C. for 1 hour. Hydrochloric acid (1M; 40 ml) was added and the mixture heated for a further 1.5 hours. The reaction mixture was basified with aqueous sodium hydroxide (5M) and extracted with ethyl acetate to give N-[1-(4-chlorophenyl)ethyl]-3-(2-methylimidazol-1-yl)propylamine as an oil.

EXAMPLE 53–57 a) In a similar manner to that described in Example 52b, the intermediate amides of formula XV in which $R_1$=4-chloro; $R_2$, $R_3$, $R_5$ and $R_6$=H; $R_4$=$CH_3$; A=$(CH_2)_n$ and Z=chloro, used in Examples 55–57 were prepared by reacting a compound of formula VII in which $R_1$=4-chloro; $R_2$, $R_3$, $R_5$ and $R_6$=H and $R_4$=$CH_3$, with the appropriate acyl chloride as summarised in Table E below (Example 52b included for comparison).

b) In a similar manner to that described in Example 52c, compounds of formula IX in which $R_1$=4-chloro; $R_2$, $R_3$, $R_5$ and $R_6$=H; $R_4$=$CH_3$; A =$(CH_2)_n$ and n are as given in Table F, were prepared by reacting the appropriate chloroamide of formula XV in which Z=chloro and $R_1$, $R_2$, $R_3$, $R_4$, $R_5$, $R_6$ and A as defined immediately above with a sodium salt of formula $Na^+Y^-$, formed by reaction of YH, in which Y represents a group of formula XXVII, with sodium hydride, as summarised in Table F below (Example 52c included for comparison).

c) In a similar manner to that described in Example 52d, compounds of formula I were prepared by reducing the amides of formula IX prepared in (b) in which A=$(CH_2)_n$ and the other substituents are as defined in (b) above with borane as summarised in Table G below (Example 52d included for comparison).

TABLE E

| Ex | Compound of formula VII Enantiomer | amt/g | Acyl Chloride ClCO(CH₂)ₙCl n | amt/g | NEt₃ amt/g | CH₂Cl₂ Total Vol/ml | Notes | Melting Point/ °C. |
|---|---|---|---|---|---|---|---|---|
| 52b | (±) | 40 | 2 | 32.7 | 28.4 | 300 | | |
| 55a | (±) | 9.9 | 4 | 9.9 | 7.0 | 75 | (1) | 70–71. |
| 56a | (+) | 18.1 | 2 | 14.8 | 12.9 | 140 | (2) | |
| 57a | (−) | 19.7 | 2 | 16.1 | 14.0 | 150 | (2) | |

Notes
(1) The product was boiled in petrol. The decanted petrol was cooled, scratched and the solid was collected by filtration.
(2) The product was triturated with petrol (40–60° C.) to give a mixture of the desired chloropropanamide and the acrylamide which was used without further purification.

TABLE F

| Ex | Compound of formula YH YH | Amt/g | NaH Amt/g | Vol THF/ ml | Compound of formula XV n | Enan | Amt/g | THF/ ml | mp °C. | Notes |
|---|---|---|---|---|---|---|---|---|---|---|
| 52c | 2-methylimidazole | 2.64 | 1.54 | 105 | 2 | (±) | 5.7 | 25 | 135–137 | (1) |
| 53b | 2-ethylimidazole | 2.62 | 1.2 | 70 | 2 | (±) | 7.38 | 30 | | (1) |
| 54b | 4(5)-methylimidazole | 2.64 | 1.54 | 105 | 2 | (±) | 5.7 | 25 | Pale yellow oil | (2) |
| 55b | imidazole | 3.97 | 2.74 | 160 | 4 | (±) | 10.7 | 60 | Oil | (3) |
| 56b | imidazole | 8.3 | 5.73 | 335 | 2 | (+) | 20 | 65 | Solid | (4) |
| 57b | imidazole | 6.2 | 4.3 | 250 | 2 | (−) | 15 | 100 | 126–128 | (5) |

NaH = 60% dispersion of sodium hydride in mineral oil.
Enan = enantiomer;
(±) = racemic compound
Ex = Example Notes (for Table F)
(1) Solid collected after ethyl acetate filtrate was evaporated was used without further purification.
(2) Ether washings after trituration were evaporated to give a pale yellow oil which was used without further purification.
(3) After boiling under reflux the reaction mixture was hot filtered through a silicon dioxide filter agent. The residue was washed with hot tetrahydrofuran and then ether. The combined filtrates were washed with water and the water re-extracted with ether to give an oily residue. The oily residue was eluted through a silica column using methanol:dichloromethane (1:9) as the mobile phase. The silica was washed through with methanol to give an oil which was used without further purification.
(4) After boiling under reflux the reaction mixture was filtered and the collected solid was washed with hot tetrahydrofuran. The combined filtrate and washings were evaporated to give an oily residue. The residue was eluted through a silica column using methanol:dichloromethane (1:9) as the mobile phase. The resulting solid was used without further purification.
(5) As for (4) above but the silica column fraction with $R_f$ 0.30 was evaporated to give a solid, m.p. 126°–128° C.

TABLE G

| Example | Amide from step (b) Amount/g | THF Volume/ml | BH3/THF(1M) Volume/ml | HCl (1M) Volume/ml | Notes |
|---|---|---|---|---|---|
| 52d | 3.21 | 80 | 55 | 40 | |
| 53c | 7.4 | 125 | 104 | 75 | (1) |
| 54c | 5.2 | 100 | 71 | 65 | (2) |
| 55c | 3.77 | 75 | 61.4 | 40 | (3) |
| 56c | 12 | 220 | 175 | 68 | (4) |
| 57c | 5.7 | 130 | 105 | 68 | (5) |

Notes (Table G)
(1) The residue was distilled at 160° C. (0.1 mmHg), dissolved in ether and treated with ethereal hydrogen chloride. The resulting solid was triturated with ether and dissolved in the minimal amount of hot ethanol. The solution was cooled, precipitated with ether and further cooled to 0° C. to give an oily gum. This was dried and triturated several times with ether to give a solid.
(2) Yellow oily product was distilled at 190° C. (0.1 mmHg) to give a colourless oil.

(3) Clear oily product was dissolved in ether and acidified with ethereal hydrogen chloride. The ether was decanted off and the gummy solid redissolved in ether. The ether was allowed to evaporate to give an oil from which the free base was liberated by treatment with 5M sodium hydroxide and extraction with ether to give an oil. The oil was dissolved in ether and acidified with ethereal oxalic acid. The solid formed was collected by filtration and recrystallised from IMS to give the solid salt.

(4) Oily product was distilled at 135° C. (0.1 mmHg), dissolved in ether and acidified with ethereal hydrogen chloride. The solid formed was collected by filtration and suspended in ether. The ether was allowed to evaporate to give a solid which was recrystallised from propan-2-ol.

(5) Oily product was dissolved in ether and acidified with ethereal hydrogen chloride. The solid formed was collected by filtration and suspended in ether. The ether was allowed to evaporate to give a solid which was recrystallised from propan-2-ol.

The compounds of formula I prepared in Examples 53 to 57 were as follows:

Ex 53 N-[1-(4-Chlorophenyl)ethyl]-3-(2-ethylimidazol-1-yl)propylamine dihydrochloride, m.p. 112°–113° C.

Ex 54 N-[1-(4-Chlorophenyl)ethyl]-3-(4/5-methylimidazol-1-yl)propylamine, b.p. 190° C. (0.1 mmHg).

Ex 55 N-[1-(4-Chlorophenyl)ethyl]-5-(imidazol-1-yl)pentylamine dioxalate, m.p. 93°–94° C.

Ex 56 (+) N-[1-(4-Chlorophenyl)ethyl]-3-(imidazol-1-yl)propylamine dihydrochloride, m.p. 122°–123° C. Chiral HPLC indicated enantiomeric purity of 98.2%. $[\alpha]_D^{22}=+21.9°$ (c=0.9 EtOH)

Ex 57 (−)N-[1-(4-Chlorophenyl)ethyl]-3-(imidazol-1-yl)propylamine dihydrochloride, m.p. 180° C. (indistinct with effervescence at 124°–127° C.). Chiral HPLC indicated enantiomeric purity of 86.8%. $[\alpha]_D^{22}=-21.5°$ (c=0.9 EtOH).

EXAMPLE 58 a) A solution of 3-chloro-2,2-dimethylpropionyl chloride (7.0 g) in dichloromethane (50 ml) was added dropwise to a stirred solution of 1-(4-chlorophenyl)ethylamine (7.0 g) and triethylamine (6.3 ml) in dichloromethane (100 ml) at 0°–5° C. under nitrogen. After the addition, the mixture was stirred at 0° C. for 0.5 hours and then stirred at ambient temperature for 2 hours. The mixture was washed with 5M hydrochloric acid and then with water. The mixture was dried and evaporated. The residue was recrystallised from petroleum ether (b.p. 60°–80° C.) to give 3-chloro-N-[1-(4-chlorophenyl)ethyl]-2,2-dimethylpropionamide, m.p. 95°–96° C.

b) A mixture of 3-chloro-N-[1-(4-chlorophenyl)ethyl]-2,2-dimethylpropionamide (5.0 g) and imidazole (6.2 g) was heated at 125° C. with stirring for 6 hours. Excess imidazole was removed by azeotropic distillation with toluene under reduced pressure. The residue was dissolved in 5M hydrochloric acid and washed with dichloromethane. The acid layer was basified with 5M sodium hydroxide solution and extracted with dichloromethane. The combined extracts were washed with water, dried and evaporated to give N-[1-(4-chlorophenyl)ethyl]-3-(imidazol-1-yl)-2,2-dimethylpropionamide which was used directly in (c) below.

c) In a similar manner to Example 52d, N-[1-(4-chlorophenyl)ethyl]-3-(imidazol-1-yl)-2,2-dimethylpropionamide (4.0 g) in THF (100 ml) was treated with BH$_3$/THF (52.1 ml, 1M) to give an oil which was distilled at 165° C. (0.05 mmHg) and the lower boiling fraction redistilled to give N-[1-(4-chlorophenyl)ethyl]-3-(imidazol-1-yl)-2,2-dimethylpropylamine, b.p. 160° C. (0.03 mmHg).

EXAMPLE 59 a) In a similar manner to Example 52b, 1-(4--chlorophenyl)-1-methylethylamine hydrochloride (20.0 g) was reacted with 3-chloropropionyl chloride (12.3 g) in dichloromethane (250 ml) containing triethylamine (27.0 ml). After basification with saturated sodium bicarbonate solution the product was extracted into dichloromethane to give a mixture of 3-chloro-N-[1-(4-chlorophenyl)-1-methylethyl]propionamide (26%) and N-[1-(4-chlorophenyl)-1-methylethyl]acrylamide (74%) which was used in part (b) below.

b) In a similar manner to Example 52c a mixture of imidazole (1.05 g) and sodium hydride (0.63 g, 60% dispersion) in THF (35 ml) was treated with 3-chloro-N-[1-(4-chlorophenyl)-1-methylethyl]propionamide (4.0 g) in THF (15 ml) to give N-[1-(4-chlorophenyl)-1-methylethyl]-3-(imidazol-1-yl)propionamide which was used directly in part (c).

c) The propionamide from (b) above (3.2 g) in THF (100 ml) was treated with BH$_3$/THF (43.8 ml, 1M) in a similar manner to Example 52d to give N-[1-(4-chlorophenyl)-1-methyl ethyl]-3-(imidazol-1-yl)propylamine, b.p. 180° C. (0.05 mmHg).

EXAMPLE 60 a) In a similar manner to Example 52c, a mixture of 2-methylimidazole (1.3 g) and sodium hydride (0.63 g, 60% dispersion) in THF (35 ml) was treated with a mixture of 3-chloro-N-[1-(4-chlorophenyl)-1-methylethyl]propionamide (4.0 g) in THF (15 ml) to give N-[1-(4-chlorophenyl)-1-methylethyl]-3-(2-methylimidazol-1-yl)propionamide as an oil which was used directly in part (b) below.

b) The propionamide, from part (a) above, (1.9 g) in THF (10 ml) was added dropwise with stirring to a suspension of aluminium hydride (8.27 mmol) in THF (18 ml) at 0°–5° C. under nitrogen. The mixture was stirred at 0° C. for 1 hour and then at ambient temperature for 2 hours. The mixture was carefully quenched with THF/H$_2$O, 1:1 (25 ml) with cooling. After basification with 5M sodium hydroxide and extraction into dichloromethane, the product obtained still contained some starting material. The mixture was dissolved in THF (5 ml) and added to a suspension of lithium aluminium hydride (0.25 g) in THF (5 ml) with stirring (under nitrogen). The mixture was boiled under reflux for 4 hours, then cooled and quenched with ethyl acetate, followed by water. The mixture was filtered and the filtrate extracted with ethyl acetate. The combined extracts were dried and evaporated. The residue was distilled to give N-[1-(4-chlorophenyl)-1-methylethyl]-3-(2-methylimidazol-1-yl)propylamine, b.p. 160° C. (0.05 mmHg).

EXAMPLE 61 a) In a similar manner to Example 52b, 3-chloro-2,2-dimethylpropionyl chloride (27.4 g) in dichloromethane (100 ml) was added to 4-chlorobenzylamine (25.0 g) and triethylamine (24.6 ml) in dichloromethane (400 ml) to give 3-chloro-N-(4-chlorobenzyl)-2,2-dimethylpropionamide, m.p. 97°–98° C.

b) The 3-chloropropionamide (8.0 g) from (a) above was reacted with imidazole (10.5 g) in a similar manner to Example 52c to give N-(4-chlorobenzyl)-3-(imidazol-1-yl)-

2,2-dimethylpropionamide which was used directly in part (c) below.

c) The propionamide (2.0g) from part (b) above was treated with BH$_3$/THF solution (27.4 ml, 1M) in a similar manner to Example 52d to give N-(4-chlorobenzyl)-3-(imidazol-1-yl)-2,2-dimethylpropylamine, b.p. 180° C. (0.4 mmHg).

EXAMPLE 62 a) 1-(4-Chlorophenyl)-1-methylethylamine hydrochloride (4.0 g) was reacted with 5-chloropentanoyl chloride (3.0 g) in dichloromethane (15 ml) containing triethylamine (8.1 ml) in a similar manner to Example 52b, to give 5-chloro-N-[1-(4-chlorophenyl)-1-methylethyl]pentanamide.

b) The chloroamide from a) (6.0 g) and imidazole (7.1 g) were heated at 125° C. with stirring for 6 hours. The mixture was diluted with dichloromethane and extracted with 5M hydrochloric acid. The acid extracts were combined, basified with 5M sodium hydroxide solution and the product extracted into dichloromethane. The combined organic extracts were washed with water, dried and evaporated to give N-[1-(4-chlorophenyl)-1-methylethyl]-5-(imidazol-1-yl)pentanamide which was used directly in part c).

c) In a similar manner to Example 52d, a solution of N-[1-(4-chlorophenyl)-1-methylethyl]-5-(imidazol-1-yl) pentanamide (5.1 g) in THF (125 ml) was reduced with BH$_3$/THF (63.7 ml of a 1M solution) to give N-[1-(4-chlorophenyl)-1-methylethyl]-5-(imidazol-1-yl)pentylamine as an oil, b.p. 195° C. (0.05 mmHg).

EXAMPLE 63 a) A mixture of 8-bromooctanoic acid (26.4 g), thionyl chloride (40 ml) and acetonitrile (40 ml) was heated at 95° C. for 3 hours. The solvent was removed by distillation under vacuum and the residue purified by azeotropic distillation, using acetonitrile, to give 8-bromooctanoyl chloride.

b) 1-(4-Chlorophenyl)-1-methylethylamine hydrochloride (4.0 g) was reacted with 8-bromooctanoyl chloride (4.7 g) in dichloromethane (50 ml) containing triethylamine (8.1 ml), in a similar manner to Example 52b, to give 8-bromo-N-[1-(4-chlorophenyl)-1-methylethyl]octanamide which was used directly in part c).

c) In a similar manner to Example 62b, a mixture of the bromoamide from b) (8.1 g) and imidazole (7.9 g) was reacted to give N-[1-(4-chlorophenyl)-1-methylethyl]-8(imidazol-1-yl)octanamide which was used directly in part d).

d) In a similar manner to Example 52d, a solution of N-[1-(4-chlorophenyl)-1-methylethyl]-8-(imidazol-1-yl)octanamide (5.9 g) in THF (130 ml) was reduced with BH$_3$/THF (64.5 ml of a 1M solution) to give N-[1-(4-chlorophenyl)-1-methylethyl]-8-(imidazol-1-yl)octylamine, b.p. 210° C. (0.05 mmHg).

EXAMPLE 64 a) A mixture of N-[-(4-chlorobenzyl)acrylamide (Example V) (3.9 g), 4,5-dichloroimidazole (2.7 g), benzyltrimethylammonium hydroxide (Triton B) (0.20 ml of 40% solution in methanol) and pyridine (13 ml) was boiled under reflux for 8 hours. The mixture was evaporated down under reduced pressure and the residue dissolved in dichloromethane (100 ml). This solution was washed with water (3×100 ml) and then extracted with 5M hydrochloric acid (3×50 ml). The combined acid extracts were basified with 5M sodium hydroxide and the product extracted into dichloromethane to give a yellow oil which was triturated with hot petroleum ether (b.p. 60°–80° C.) to give solid N-(4-chlorobenzyl)-3-(4,5-dichloroimidazol-1-yl)propionamide which was sufficiently pure by 1H nmr spectroscopy for use in part (b) below.

b) The material from part (a) above (4.2 g) was dissolved in dry THF (70 ml) under nitrogen and borane/THF complex (51 ml, 1M solution) was added in one portion at ambient temperature. The mixture was boiled under reflux for 2.5 hours and then evaporated to dryness under reduced pressure. The residue was heated at 95° C. under nitrogen for 45 mins. cooled and then 1M hydrochloric acid (60 ml) added. The mixture was heated at 95° C. for 1.5 hours. On cooling the mixture was basified with concentrated sodium hydroxide solution (12M) and extracted with ethyl acetate. The combined organic extracts were extracted with 5M hydrochloric acid and the combined acid extracts basified with 5M sodium hydroxide and the product extracted into ethyl acetate to give an oil which contained a little solid material. The oil was dissolved in ether and filtered to remove this solid. The filtrate was evaporated to give an oil which was treated with ethereal hydrogen chloride to give N-(4-chlorobenzyl)-3-(4,5-dichloroimidazol-1-yl)propylamine dihydrochloride, m.p. 185°–187° C.

EXAMPLE 68a (Alternative procedure)

A mixture of N-[1-(4-chlorophenyl)-1-methylethyl]acrylamide (200 g), imidazole (60.9 g), Triton B (20 ml) and 1,4-dioxane (1600 ml) was stirred and boiled under reflux for 20 hours. The solvent was removed under reduced pressure and the residue dissolved in dichloromethane (2000 ml). The mixture was extracted with 2M hydrochloric acid. The combined aqueous extracts were basified with 2M sodium hydroxide solution and extracted with dichloromethane to give N-[1-(4-chlorophenyl)-1-methylethyl]-3-(imidazol-1-yl)propionamide, m.p. 154°–155° C.

EXAMPLE 65–88

Compounds of formula XVI in which $R_1$, $R_2$, $R_3$, $R_4$, and $R_5$ are as defined in Tables H1 and H2 and $R_6$ represents hydrogen were reacted with compounds of formula YH in which Y represents an imidazole group of formula XXVII in which $R_8$, $R_9$ and $R_{10}$ are defined in Tables H1 and H2, in a similar manner to Examples 64a and 68a (alternative procedure), as summarised in Tables H1 and H2 respectively, to give compounds of formula IX in which A represents $(CH_2)_2$ and $R_1$–$R_6$ are as defined above. In cases where a mixture of two regioisomers was formed, the components of the mixture were separated and their structures assigned from their $^1$H nmr and/or $^{13}$C nmr spectra by comparing chemical shifts and coupling constants with those of known substituted imidazoles. The products were reduced in a similar manner to Example 64b as summarised in Table I to give compounds of formula I. In Examples 79, 84, 85, 86 and 88 reduction of other functional groups also occurred.

TABLE H1

| Ex | Acrylamide XVI $R_1R_2R_3$ | $R_4$ | $R_5$ | Wt/g | Imidazole $R_8$ | $R_9$ | $R_{10}$ | Wt/g | Pyridine Vol/ml | Triton B* Vol/ml | NB |
|---|---|---|---|---|---|---|---|---|---|---|---|
| 65a | 4-Cl | CH$_3$ | H | 8.4 | i-C$_3$H$_7$ | H | H | 4.4 | 26 | 0.4 | |
| 66a | 4-Cl | CH$_3$ | H | 3.7 | CH$_3$ | CH$_3$ | CH$_3$ | 2.0 | 12 | 0.2 | (1) |
| 67a | 4-Cl | CH$_3$ | H | 8.4 | H | Cl | Cl | 5.5 | 26 | 0.5 | |
| 68a | 4-Cl | CH$_3$ | CH$_3$ | 0.15 | H | H | H | 0.045 | 1.5 | 0.005 | (2) |
| 69a | 4-Cl | CH$_3$ | CH$_3$ | 4.0 | H | H/CH$_3$ | CH$_3$/H | 1.5 | 10 | 0.14 | |
| 70a | 4-Cl | CH$_3$ | CH$_3$ | 2.8 | H | CH$_3$ | CH$_3$ | 1.7 | 10 | 0.10 | |
| 71a | 4-Cl | H | H | 7.8 | i-C$_3$H$_7$ | H | H | 4.4 | 25 | 0.44 | |
| 72a | 4-Cl | H | H | 7.8 | C$_2$H$_5$ | H | H | 3.8 | 25 | 0.44 | |
| 73a | 4-CH$_3$ | CH$_3$ | CH$_3$ | 4.8 | CH$_3$ | H | H | 1.9 | 15 | 0.26 | |
| 74a | 4-Cl | CH$_3$ | CH$_3$ | 4.0 | H | NO$_2$ | H | 2.0 | 12 | 0.16 | |
| 75a | 4-CH$_3$ | CH$_3$ | CH$_3$ | 4.8 | H | H | H | 1.6 | 15 | 0.26 | |
| 76a | 4-Cl | C$_2$H$_5$ | C$_2$H$_5$ | 11.6 | H | H | H | 3.14 | 40 | 0.51 | |
| 77a | 4-CO$_2$Et | CH$_3$ | CH$_3$ | 0.37 | H | H | H | 0.96 | 4 | 0.33 | |
| 78a | 4-Cl | CH$_3$ | CH$_3$ | 4.0 | H | CH$_3$ | CO$_2$Et | 2.76 | 12 | 0.16 | (3) |

*Volume of 40% solution in methanol.
Et = C$_2$H$_5$

TABLE H2

| Ex | Acrylamide XVI $R_1R_2R_3$ | $R_4$ | $R_5$ | Wt/g | Imidazole $R_8$ | $R_9$ | $R_{10}$ | Wt/g | 1,4-dioxane Vol/ml | Triton B* Vol/ml | NB |
|---|---|---|---|---|---|---|---|---|---|---|---|
| 79a | 4-Cl | CH$_3$ | CH$_3$ | 22.3 | H | CHO/H | H/CHO | 9.6 | 112 | 2.24 | (4) |
| 80a | H | C$_2$H$_5$ | C$_2$H$_5$ | 8.7 | H | H | H | 2.7 | 50 | 0.9 | |
| 81a | 4-Ph | CH$_3$ | CH$_3$ | 5.0 | H | H | H | 1.3 | 23 | 0.45 | |
| 82a | 4-Cl | —CH$_2$CH$_2$— | | 6.6 | H | H | H | 2.2 | 75 | 0.5 | |
| 83a | 3,4-NAP | CH$_3$ | CH$_3$ | 5.0 | H | H | H | 1.4 | 26 | 0.5 | |
| 84a | 3,4-Cl$_2$ | CH$_3$ | CH$_3$ | 16.0 | H | CHO/H | H/CHO | 9.2 | 250 | 2.8 | (5) |
| 85a | 4-Ph | CH$_3$ | CH$_3$ | 4.8 | H | CHO | H | 2.6 | 40 | 0.8 | |
| 86a | H | C$_2$H$_5$ | C$_2$H$_5$ | 8.0 | H | CHO/H | H/CHO | 6.0 | 120 | 2.6 | |
| 87a | 4-OCH$_2$Ph | CH$_3$ | CH$_3$ | 26.2 | H | H | H | 6.6 | 250 | 2.0 | |

NAP = —CH=CH—CH=CH—

Notes to Tables H1 and H2

(1) 2,4,5-Trimethylimidazole was prepared as described in Chem. Ber. 86, 96 (1953).

(2) The residue was recrystallised from ethyl acetate.

(3) Xylene (20 ml) was added to the reactants and the mixture boiled under reflux for 7 hours. After work-up as described in Example 62a, the mixture was separated by flash column chromatography on silica using ethyl acetate/triethylamine (9:1) as the mobile phase. The first product fraction gave ethyl 1-{N-[1-(4-chlorophenyl)-1-methylethyl]-2-carbamoylethyl}-4-methylimidazole-5-carboxylate, as an oil not distilled (Example 78a). The column was flushed with methanol to give ethyl 1-{N-[1-(4-chlorophenyl)-1-methylethyl]-2-carbamoylethyl}-5-methylimidazole-4-carboxylate, as an oil not distilled, which was used as the starting material in Example 98.

(4) The reaction mixture was left to stand at ambient temperature for 18 hours then a solid was collected by filtration and recrystallised twice from ethyl acetate to give N-[1-(4-chlorophenyl)-1-methylethyl]-3-(4-formylimidazol-1-yl)propionamide, m.p. 151°–153° C. (79a) which was used in Example 79b.

The mother liquors from the recrystallisations were combined and evaporated to dryness. Water was added to the residue and this mixture was extracted with dichloromethane. The dichloromethane extracts were extracted with 5M hydrochloric acid. The acidic extracts were combined, basified and extracted with dichloromethane to yield a residue which was triturated with ethyl acetate and filtered to remove the isomer above. The filtrate was evaporated and the residue purified by column chromatography over silica using ethyl acetate/triethylamine (9:1) as the mobile phase to give N-[1-(4-chlorophenyl)-1-methylethyl]-3-(5-formylimidazol-1-yl)propionamide, m.p. 127°–129° C. (Example 88a) which was used in Example 88b.

(5) The mixture was cooled in ice, allowed to warm to ambient temperature and the solid filtered off and recrystallised from ethyl acetate to give N-[1(3,4-dichlorophenyl)-1-methylethyl]-3-(4-formylimidazol-1-yl)propionamide, m.p. 161°–163° C. The dioxane filtrate was evaporated to dryness and the residue partitioned between water and dichloromethane. The combined dichloromethane extracts were extracted with 5M hydrochloric acid. Combined acidic extracts were basified with concentrated sodium hydroxide solution and extracted with dichloromethane to yield a residue which was triturated with ethyl acetate and filtered. The solid obtained was dissolved in ethyl acetate and passed through a silica column using ethyl acetate as the mobile phase. This produced N-[1-(3,4-dichlorophenyl)-1-methylethyl]-3-(5-formylimidazol-1-yl)propionamide, m.p. 180°–181.5° C. which was used to prepare Example 84b.

TABLE I

| Ex | R$_1$R$_2$R$_3$ | R$_4$ | R$_5$ | R$_8$ | R$_9$ | R$_{10}$ | wt/g | BH3/THF | THF Vol/ml | Notes |
|---|---|---|---|---|---|---|---|---|---|---|
| 65b | 4-Cl | CH$_3$ | H | i-C$_3$H$_7$ | H | H | 6.4 | 80 | 100 | (1) |
| 66b | 4-Cl | CH$_3$ | H | CH$_3$ | CH$_3$ | CH$_3$ | 2.3 | 29 | 50 | |
| 67b | 4-Cl | CH$_3$ | H | H | Cl | Cl | 5.7 | 65 | 80 | |
| 68b | 4-Cl | CH$_3$ | CH$_3$ | H | H | H | 3.2 | 43.8 | 100 | (2) |
| 69b | 4-Cl | CH$_3$ | CH$_3$ | H | H/CH$_3$ | CH$_3$/H | 3.5 | 45.5 | 90 | (2) |
| 70b | 4-Cl | CH$_3$ | CH$_3$ | H | CH$_3$ | CH$_3$ | 2.0 | 24.9 | 50 | (2) |
| 71b | 4-Cl | H | H | i-C$_3$H$_7$ | H | H | 10.7 | 145 | 250 | |
| 72b | 4-Cl | H | H | C$_2$H$_5$ | H | H | 11.0 | 157 | 270 | |
| 73b | 4-CH$_3$ | CH$_3$ | CH$_3$ | CH$_3$ | H | H | 2.0 | 50 | 50 | |
| 74b | 4-Cl | CH$_3$ | CH$_3$ | H | NO$_2$ | H | 1.7 | 20.5 | 40 | |
| 75b | 4-CH$_3$ | CH$_3$ | CH$_3$ | H | H | H | 2.7 | 44.1 | 70 | |
| 76b | 4-Cl | C$_2$H$_5$ | C$_2$H$_5$ | H | H | H | 5.0 | 65 | 110 | |
| 77b | 4-CO$_2$C$_2$H$_5$ | CH$_3$ | CH$_3$ | H | H | H | 10.5 | 126 | 250 | (3) |
| 78b | 4-Cl | CH$_3$ | CH$_3$ | H | CH$_3$ | CO$_2$C$_2$H$_5$ | 0.37 | 3.9 | 6.0 | |
| 79b | 4-Cl | CH$_3$ | CH$_3$ | H | CHO | H | 3.2 | 62 | 70 | |
| 80b | H | C$_2$H$_5$ | C$_2$H$_5$ | H | H | H | 4.2 | 58.4 | 100 | |
| 81b | 4-Ph | CH$_3$ | CH$_3$ | H | H | H | 4.7 | 56 | 97 | |
| 82b | 4-Cl | —CH$_2$—CH$_2$— | | H | H | H | 5.0 | 83 | 150 | |
| 83b | 3,4-NAP | CH$_3$ | CH$_3$ | H | H | H | 2.26 | 29.5 | 51 | |
| 84b | 3,4-Cl$_2$ | CH$_3$ | CH$_3$ | H | H | CHO | 1.9 | 33.3 | 38 | |
| 85b | 4-Ph | CH$_3$ | CH$_3$ | H | CHO | H | 1.6 | 28.0 | 30 | |
| 86b | H | C$_2$H$_5$ | C$_2$H$_5$ | H | CHO | H | 5.7 | 117 | 130 | |
| 87b | 4-OCH$_2$Ph | CH$_3$ | CH$_3$ | H | H | H | 3.0 | 32.9 | 70 | |
| 88b | 4-Cl | CH$_3$ | CH$_3$ | H | H | CHO | 1.5 | 29 | 33 | |

NAP = —CH=CH—CH=CH—

Notes to Table I (1) The product (free base) was extracted into dichloromethane. The hydrochloride salt obtained was very hygroscopic and so was converted back to the free base by treatment with 12M sodium hydroxide. The liberated base was extracted into dichloromethane and the extracts combined, dried and evaporated to give the product.

(2) The product was extracted into dichloromethane after basification and then distilled.

(3) The oil obtained on work-up was purified by flash column chromatography on silica using ethyl acetate/triethylamine (99:1) as the mobile phase.

The compounds prepared in Table H were:

Ex 65a N-[1-(4-Chlorophenyl)ethyl]-3-(2-isopropylimidazol-1-yl)propionamide, as an oil not distilled.

Ex 66a N-[1-(4-Chlorophenyl)ethyl]-3-(2,4,5-trimethylimidazol-1-yl)propionamide, m.p.). 141°–143° C.

Ex 67a N-[1-(4-Chlorophenyl)ethyl]-3-(4,5-dichloroimidazol-1-yl)propionamide as an oil not distilled.

Ex 68a N-[1-(4-Chlorophenyl)-1-methylethyl]-3-(imidazol-1-yl)propionamide, m.p. 154°–155° C. (after recrystallisation from ethyl acetate).

Ex 69a A mixture of N-[1-(4-chlorophenyl)-1-methylethyl]-3-(4-methylimidazol-1-yl)propionamide and N-[1-(4-chlorophenyl)-1-methylethyl]-3-(5-methylimidazol-1-yl)propionamide.

Ex 70a N-[1-(4-Chlorophenyl)-1-methylethyl]-3-(4,5dimethylimidazol-1-yl)propionamide.

Ex 71a N-(4-Chlorobenzyl)-3-(2-isopropylimidazol-1-yl)propionamide (oil).

Ex 72a N-(4-Chlorobenzyl)-3-(2-ethylimidazol-1-yl)propionamide (oil).

Ex 73a 3-(2-Methylimidazol-1-yl)-N-[1-methyl-1-(p-tolyl)ethyl]propionamide, m.p. 133°–135° C.

Ex 74a N-{1-(4-Chlorophenyl)-1-methylethyl]-3-(4-nitroimidazol-1-yl)propionamide, m.p. 165°–166° C.

Ex 75a 3-(Imidazol-1-yl)-N-[1-methyl-1-(p-tolyl)ethyl]propionamide, m.p. 120°–121° C.

Ex 76a N-[1-(4-chlorophenyl)-1-ethylpropyl]-3-(imidazol-1-yl)propionamide as an oil.

Ex 77a Ethyl {1-[3-(imidazol-1-yl)propionamido]-1-methylethyl}benzoate, m.p. 118°–119° C.

Ex 78a Ethyl 1-{N-[-1-(4-chlorophenyl)-1-methylethyl]-2-carbamoylethyl}-4-methylimidazole-5-carboxylate, as an oil not distilled Ex 79a N-[1-(4-Chlorophenyl)-1-methylethyl]-3-(4-formylimidazol-1-yl)propionamide, m.p. 151°–153° C.

Ex 80a N-(1-Ethyl-1-phenylpropyl)-3-(imidazol-1-yl)propionamide, as an oil.

Ex 81a N-[1-(4-Biphenylyl)-1-methylethyl]-3-(imidazol-1-yl)propionamide, as an oil.

Ex 82a N-[1-(4-Chlorophenyl)cycloprop-1-yl]-3-(imidazol-1-yl)propionamide, m.p. 135.5°–136.5° C.

Ex 83a 3-(Imidazol-1-yl)-N-[1-methyl-1-(2-naphthyl)ethyl]propionamide.

Ex 84a N-[1-(3,4-Dichlorophenyl)-1-methylethyl]-3-(5-formylimidazol-1-yl)propionamide, m.p. 180°–181.5° C. (see Table H2 Note 5).

Ex 85a N-{1-(4-Biphenylyl)-1-methylethyl]-3-(4-formylimidazol-1-yl)propionamide, m.p. 171°–172° C.

Ex 86a N-(1-Ethyl-1-phenylpropyl)-3-(4-formylimidazol-1-yl)propionamide, m.p. 142°–143.5° C.

Ex 87a N-[1-(4-Benzyloxyphenyl)-1-methylethyl]-3-(imidazol-1-yl)propionamide, m.p. 187°–189° C.

The compounds prepared in Table I were:

Ex 65b N-[1-(4-Chlorophenyl)ethyl]-3-(2-isopropylimidazol-1-yl)propylamine, as an oil not distilled.

Ex 66b N-[1-(4-Chlorophenyl)ethyl]-3-(2,4,5-trimethylimidazol-1-yl)propylamine, as an oil not distilled.

Ex 67b N-[1-(4-Chlorophenyl)ethyl]-3-(4,5-dichloroimidazol-1-yl)propylamine sesquihydrochloride, m.p. 248°–250° C. (with decomposition).

Ex 68b N-[1-(4-Chlorophenyl)-1-methylethyl]-3-(imidazol-1-yl)propylamine as an oil, b.p. 180° C. (0.05 mmHg) [Example 68(1)]. A sample of this oil was dissolved in ether and ethereal hydrogen chloride added. The solid obtained was collected by filtration, dried and recrystallised from propan-2-ol to give N-[1-(4-chlorophenyl)-1-methylethyl]-3-(imidazol-1-yl)propylamine dihydrochloride, m.p. 216°–218° C. [Example 68(2)].

Ex 69b A mixture of N-[1-(4-chlorophenyl)-1-methylethyl]-3-(4-methylimidazol-1-yl)propylamine and N-[1-(4-chlorophenyl)-1-methylethyl]-3-(5-methylimidazol- 1-yl) propylamine as an oil, b.p. 160°–170° C. (0.1 mmHg). $^{13}$C nmr spectroscopy indicates that the ratio of 4-methyl isomer: 5-methyl isomer is 2:1.

Ex 70b N-[1-(4-Chlorophenyl)-1-methylethyl]-3-(4,5-dimethylimidazol-1-yl)propylamine, b.p. 165° C. (0.05 mmHg).

Ex 71b N-(4-Chlorobenzyl)-3-(2-isopropylimidazol-1-yl) propylamine-dihydrochloride, m.p. 189°–192° C.

Ex 72b N-(4-Chlorobenzyl)-3-(2-ethylimidazol-1-yl)propylamine, b.p. 155°–165° C. (0.1mmHg).

Ex 73b 3-(2-Methylimidazol-1-yl)-N-[1-methyl-1-(p-tolyl) ethyl]propylamine dihydrochloride, m.p. 255° C. (with decomposition).

Ex 74b N-[1-(4-Chlorophenyl)-1-methylethyl]-3-(4-nitroimidazol-1-yl)propylamine as an oil not distilled. Material purified by flash chromatography (silica, mobile phase ethyl acetate/methanol).

Ex 75b 3-(Imidazol-1-yl)-N-[1-methyl-1-(p-tolyl)ethyl]propylamine dihydrochloride, m.p. 206° C. (with decomposition).

Ex 76b 1-(4-Chlorophenyl)-1-ethyl-3'-(imidazol-1-yl)dipropylamine dihydrochloride, m.p. 208°–211° C.

Ex 77b Ethyl 4-{1-[3-(imidazol-1-yl)propylamino]-1-methylethyl}benzoate as an oil not distilled.

Ex 78b Ethyl 1-{3-[1-(4-chlorophenyl)-1-methylethylamino]propyl}- 4-methylimidazole-5-carboxylate as an oil not distilled.

Ex 79b 1-{3-[1-(4-Chlorophenyl)-1-methylethylamino] propyl}imidazol-4-yl-methanol, m.p. 103°–104° C.

Ex 80b N-(1-Ethyl-1-phenylpropyl)-3-(imidazol-1-yl)propylamine, b.p. 140°–150° C. (0.02 mmHg).

Ex 81b N-[1-(4-Biphenylyl)-1-methylethyl]-3-(imidazol-1-yl)propylamine dihydrochloride, m.p. 222°–226° C.

Ex 82b N-[1-(4-Chlorophenyl)cycloprop-1-yl]-3-(imidazol-1-yl)propylamine dihydrochloride, m.p. 188°–189° C.

Ex 83b N-[1-(2-Naphthyl)-1-methylethyl]-3-(imidazol-1-yl) propylamine dihydrochloride hemihydrate, m.p. 219°–222° C.

Ex 84b 1-{3-[1-(3,4-Dichlorophenyl)-1-methylethylamino] propyl}imidazol-5-ylmethanol, m.p. 117°–118° C.

Ex 85b The residue obtained on work-up was recrystallised from cyclohexane/ethyl acetate (5:7) to give 1-{3-[1-(4-biphenylyl)-1-methylethylamino]propyl}imidazol-4-yl-methanol, m.p. 128°–129.5° C.

Ex 86b The residue obtained on work up was recrystallised from cyclohexane to give 1-[3-(1-ethyl- 1-phenylpropylamino)propyl]imidazol-4-yl-methanol, m.p. 82°–84 ° C.

Ex 87b N-[1-(4-Benzyloxyphenyl)-1-methylethyl]-3-(imidazol-1-yl)propylamine dihydrochloride, m.p. 186°–187° C.

Ex 88b 1-{3-[1-(4-Chlorophenyl)-1-methylethylamino] propyl}imidazol-5-yl-methanol dihydrochloride, m.p. 165°–169° C.

EXAMPLE 89 a) In a similar manner to Example 52b, 1-(4-chlorophenyl)- 1-methylethylamine hydrochloride (2.5 g) was treated with 4-chlorobutyryl chloride (1.7 g) in dichloromethane (30 ml) containing triethylamine (3.4 ml) to give 4-chloro-N-[1-(4-chlorophenyl)-1-methylethyl]butyramide which was used directly in part (b) below.

b) The chlorobutyramide (3.1 g) from (a) above and imidazole (3.8 g) were heated at 125° C. for 6 hours. The mixture was cooled, dissolved in 5M hydrochloric acid and then washed with dichloromethane. The aqueous phase was basified with 5M sodium hydroxide and then extracted with dichloromethane. The combined extracts were dried and evaporated to give N-[1-(4-chlorophenyl)-1-methylethyl]-4-(imidazol-1-yl)butyramide which was used directly in part (c) below.

c) The butyramide (2.9 g) from (b) above was reduced with borane/THF (37.1 ml, 1M) in a similar manner to Example 52d to give N-[1-(4-chlorophenyl)-1-methylethyl]-4-(imidazol-1-yl)butylamine, b.p. 160° C. (0.01 mmHg).

EXAMPLE 90

N-[1-(4-Chlorophenyl)ethyl]-3-(imidazol-1-yl)propylamine dihydrochloride (1.7 g, prepared in Example 1) was added in portions to formic acid (1.2 g, 97%) at 0° C. Formaldehyde (0.96 g, 37%) was added and the mixture heated to 95° C. for 6 hours. After cooling, concentrated hydrochloric acid (0.6 ml) was added and the solution evaporated to dryness under reduced pressure. The residue was dissolved in water, basified with 5M sodium hydroxide solution and the product extracted into ether. The combined extracts were dried and evaporated. The oil obtained was dissolved in ether and treated with ethereal hydrogen chloride. The hydrochloride salt obtained was hygroscopic and so was basified with 5M sodium hydroxide to give N-[1-(4-chlorophenyl)ethyl]-3-(imidazol-1-yl)-N-methylpropylamine as an oil which was not distilled.

EXAMPLE 91 n-[1-(4-Chlorophenyl)propyl]-3-(imidazol-1-yl)propylamine (13.9 g, free base of Example 30) was added in portions to formic acid (11.75 g, 98–100%) at 0° C. Formaldehyde (9.6 g, 37%) was added and the mixture heated at 95° C. for 6 hours. Work-up as described in Example 90 gave N-[1-(4-chlorophenyl)propyl]-3-(imidazol-1-yl)-N-methylpropylamine as an oil which was not distilled.

EXAMPLE 92 a) A solution of (±)N-[1-(4-chlorophenyl)ethyl]-3-(imidazol-1-yl)propylamine (5.3 g), prepared as in Example 1, in ethanol (10 ml) was mixed with a solution of D(−)tartaric acid (3.0 g) in ethanol (50 ml) and heated at reflux with stirring until a colourless solid precipitated. The mixture was cooled, the solid collected by filtration, washed with IMS and recrystallised three times from IMS to give (−) N-[1-(4-chlorophenyl)ethyl]-3-(imidazol-1-yl)propylamine (−)-ditartrate, m.p. 180°–183° C. (with decomposition). Chiral HPLC indicated enantiomeric purity of 98.1%.

EXAMPLE 93 a) A solution of (±)N-[1-(4-chlorophenyl)ethyl]-3-(imidazol- 1-yl)propylamine (15.8 g), prepared as described in Example 1, in IMS (50 ml) was mixed with a solution of L(+) tartaric acid (9.0 g) in IMS (100 ml). The mixture was made up to 300 ml with IMS and heated to reflux with gentle stirring until a solid precipitated. The mixture was cooled, the solid collected by filtration, washed with IMS and recrystallised twice from IMS to give (+)N-[1-(4-chlorophenyl)ethyl]-3-(imidazol-1-yl)-propylamine (+) ditartrate, m.p. 181°–183° C. (with decomposition). Chiral HPLC indicated enantiomeric purity of 94.1%.

EXAMPLE 94

The product from Example 49 (4.0 g), propan-1-ol (50 ml) and concentrated sulphuric acid (2.0 ml) was boiled under reflux for 22 hours. The solvent was removed under reduced pressure and the residue dissolved in water (50 ml) and basified with 5M sodium hydroxide solution. The product was extracted into ethyl acetate. Distillation gave propyl 4-[3-(2-methylimidazol-1-yl)propylaminomethyl]benzoate, b.p. 185°–195° C. (0.05 mmHg).

EXAMPLE 95

In a similar manner to Example 70, 5-chloro-N-(4-chlorobenzyl)valeramide (10.3 g, prepared from 4-chlorobenzylamine and 5-chlorovaleryl chloride) and 2-methylimidazole (6.5 g) were reacted together to give N-( 4-chlorobenzyl)-5-(2-methylimidazol-1-yl) valeramide, (6.5 g) , m.p. 72°–75° C. which was reduced with borane/THF (86 ml, 1M) to give N-(4-chlorobenzyl)-5-(2-methylimidazol- 1-yl) pentylamine, b.p. 170°–185° C. (0.1 mmHg).

EXAMPLE 96

In a similar manner to Example 90, N-[1-(4-chlorophenyl)- 1-methylethyl]-3-(imidazol-1-yl)propylamine was reacted with formaldehyde and formic acid to give N-[1-(4-chlorophenyl)-1-methylethyl]-3-(imidazol- 1-yl)-N-methylpropylamine, b.p. 170° C. (0.03 mmHg).

EXAMPLE 97

In a similar manner to Example 90, N-(4-chlorobenzyl)-3-(2-methylimidazol-1-yl)propylamine was treated with formaldehyde and formic acid to give N-(4-chlorobenzyl)-N-methyl- 3-(2-methylimidazol-1-yl)propylamine, b.p. 160°–166° C. (0.2 mmHg).

EXAMPLE 98 a) In a similar manner to Example 64b, a mixture of ethyl 1-{N-[1-(4-chlorophenyl)-1-methylethyl]-2carbamoylethyl}- 5-methylimidazole-4-carboxylate (28.8 g, from Example 78) and borane/THF (303.4 ml, 400 ml THF, 1.0M solution) gave 1-{3-[1-(4-chlorophenyl)-1-methylethylamino]propyl}-5-methylimidazol-4-yl-methanol, m.p. 97°–99° C.

b) A solution of acetyl chloride (8.7 g) in dichloromethane (35.5 ml) was added dropwise with stirring to a solution of 1-{3-[1-(4-chlorophenyl)-1-methylethylamino]propyl}-5-methylimidazol-4-yl-methanol (3.55 g) in dichloromethane (88.8 ml) containing triethylamine (11.1 g) at 0° C. The mixture was stirred at 0° C. for 30 minutes and then at ambient temperature for 2 hours. The mixture was diluted with dichloromethane, washed with 5M sodium hydroxide solution, dried and evaporated. The residue obtained was dissolved in ether and acidified with ethereal hydrogen chloride. The solid was collected by filtration and recrystallised from aqueous propan-1-ol to give 1-{3-[1-(4-chlorophenyl)-1-methylethylamino]propyl}-5-methylimidazol-4-ylmethyl acetate dihydrochloride, m.p. 188°–189° C.

EXAMPLE 99

N-[1-(4-Chlorophenyl)-1-methylethyl]-3-(imidazol-1-yl)propylamine (1.25 g) and citric acid (0.95 g) were dissolved in warm IMS (10 ml) and allowed to cool. After standing with occasional scratching a salt crystallised. The salt was collected by filtration, triturated with ethyl acetate/methanol (1:1) filtered and dried to give N-[1-(4-chlorophenyl)-1-methylethyl]-3-(imidazol-1-yl)propylamine citrate, m.p. 143°–145° C.

EXAMPLE 100

N-[1-(4-Chlorophenyl)-1-methylethyl]-3-(imidazol-1-yl) propylamine (2.57 g) and L-(+)-tartaric acid (1.39 g) were dissolved in warm IMS (10 ml) and allowed to cool. On scratching a salt crystallised. The salt was collected by filtration and recrystallised from IMS to give N-[1-(4-chlorophenyl)-1-methylethyl]-3-(imidazol- 1-yl)propylamine (+)tartrate dihydrate, m.p. 76°–78° C.

EXAMPLE 101 a) In a similar manner to Example 68a (alternative procedure), a mixture of N-[1-(4-chlorophenyl)-1methylethyl] acrylamide (6.7 g), 2-isopropylimidazole (3.3 g), 1,4-dioxane (100 ml) and benzyltrimethyl-ammonium hydroxide (Triton B) (5 ml of 40% solution in methanol) gave N-[1-(4-chlorophenyl)-1-methylethyl]-3-(2-isopropylimidazol-1-yl)propionamide as an oil not distilled.

b) In a similar manner to Example 64b, a mixture of the amide from a) above (5.8 g) and borane/THF complex (70 ml, 1M solution) gave N-[1-(4-chlorophenyl)-1-methylethyl]-3-(2-isopropylimidazol-1-yl)propylamine dihydrochloride, m.p. 156° C.

EXAMPLE 102 a) Sodium (26.7 g) was dissolved in methanol (600 ml) and the solution cooled to –45° C. Bromine (65.3 g) was added dropwise with vigorous stirring while keeping the temperature –45° C. Once the colour had discharged, a solution of 2-methyl-2-(p-tolyl)propionamide (69.3 g) in 1,4-dioxane (257 ml) and methanol (350 ml) was added slowly over 20 minutes at –45° C. The mixture was allowed to warm up gradually to 20° C. whereupon an exotherm occurred which raised the temperature to 50° C. The exotherm was controlled by external cooling. The mixture was then boiled under reflux for 4.5 hours and the solvent removed under reduced pressure. The residue was diluted with 5M sodium hydroxide solution and extracted with ether to give methyl N-[1-methyl-1-(p-tolyl)ethyl]carbamate, m.p. 42°–43° C.

b) A mixture of the carbamate from a) (4.0 g), N-bromosuccinimide (3.8 g), carbon tetrachloride (80 ml) and azobisisobutyronitrile (0.12 g) was boiled under reflux for 18 hours. The mixture was cooled, washed with water, dried, filtered and the solvent removed by distillation under reduced pressure to give methyl N-[1-(4-bromomethylphenyl)-1-methylethyl]carbamate, m.p. 74°–76° C.

c) A solution of potassium cyanide (24.4 g) in water (70 ml) was added dropwise over 20 minutes at 50° C. to a mixture of a product from part b) (60.0 g) in acetonitrile (500 ml). The mixture was boiled under reflux for i hour and then the solvent removed under reduced pressure. The residue was diluted with water and extracted with ether to give a residue which was recrystallised from petroleum ether, b.p. 60°–80° C./propan-2-ol to give methyl N-[1-(4-cyanomethylphenyl)- 1-methylethyl]carbamate, m.p. 88°–90° C.

d) Trimethylsilyl iodide (24.0 g) was added over 5 minutes to a solution of the product from part c) (28.0 g) in chloroform (200 ml) with stirring under nitrogen at ambient temperature. The mixture was stirred at 60° C. for 2.5 hours then cooled in ice/water, quenched with saturated methanolic hydrogen chloride (20 ml) and stirred at ambient temperature for a further hour. The solvent was removed under reduced pressure and the residue diluted with ether (250 ml) and stirred at ambient temperature for 64 hours. The mixture was filtered to give 4-(1-amino-1-methylethyl)phenylacetonitrile.

e) The product from part d) (8.0 g) and 6M hydrochloric acid (100 ml) was boiled under reflux for 6 hours. The supernatant liquid was decanted away from some insoluble material and then evaporated under reduced pressure. The residue was stored under vacuum over phosphorus pentoxide for 16 hours. The residue was boiled under reflux in propan-1-ol (300 ml) containing concentrated sulphuric acid (5 ml) at 95° C. for 64 hours. The solvent was removed under reduced pressure and the residue diluted with water and washed with ether. The acidic aqueous layer was basified with 5M sodium hydroxide solution and extracted with ether to give propyl 4-(1-amino-1-methylethyl)phenylacetate as an oil.

f) A solution of acryloyl chloride (1.7 g) in dichloromethane (15 ml) was added dropwise to a mixture of the product from e) (4.32 g), triethylamine (2.6 ml) and dichloromethane (50 ml) with stirring, under nitrogen. The mixture was stirred at 0° C. for 30 minutes and then at ambient temperature for 2.5 hours. The mixture was diluted with dichloromethane, washed with water and the organic layer dried and evaporated to give an oily residue. This oil was purified by flash chromatography on silica using petroleum ether b.p. 60°–80° C./ethyl acetate, 2:1 as the mobile phase to give propyl 4-(1-acrylamido-1-methylethyl)phenylacetate, m.p. 71°–72° C.

g) A mixture of the product from f) (1.7 g), imidazole (0.4 g), benzyltrimethylammonium hydroxide (Triton®B) (4.9 mg of a 40% solution in methanol) and 1,4-dioxane (20 ml) was heated at 95° C. for 18 hours. Work up as described in Example 68a (Alternative Procedure), but using ethyl acetate as the extracting solvent, gave propyl 4-{1-[3-(imidazol-1-yl)propionamido]-1-methylethyl}phenylacetate as an oil. $^1$H nmr confirmed the structure.

h) The product from g) (460 mg), borane/THF (3.9 ml of a 1M solution) and THF (20 ml) were stirred at ambient temperature for 6 hours. The solvent was removed under reduced pressure and propan-1-ol (20 ml) saturated with hydrogen chloride gas was added. This mixture was heated at 95° C. for 1 hour and then the solvent was removed under reduced pressure. The residue was added to water and the solution washed with ethyl acetate. The aqueous acidic layer was separated, then basified with 5M sodium hydroxide solution and the product extracted into ethyl acetate to give an oil. The oil was purified by flash chromatography on silica using methanol/ethyl acetate, 1:1, as the mobile phase, to give propyl 4-{1-[3-(imidazol-1-yl)propylamino]-1-methylethyl}phenyl acetate, as an oil. $^1$H nmr (250 MHz) (CDCl$_3$), 0.91 (3H, t), 1.42 (6H, s), 1.5 (1H, s,br), 1.65 (2H, sextet), 1.83 (2H, pentuplet), 2.32 (2H, t), 3.61 (2H,s), 3.98 (2H, t), 6.83 (1H, s), 7.02 (1H, s) and 7.2–7.45 (5H,m).

EXAMPLE 103

A solution of acetyl chloride (0.24 ml) in dichloromethane (6 ml) was added dropwise to a solution of 1-[3-(1-ethyl-1-phenylpropylamino)propyl]imidazol-4-yl-methanol (10 g, from Example 86b) in dichloromethane (18 ml) containing triethylamine (0.46 ml), with stirring, at 0° C. The mixture was stirred at 0° C. for 30 minutes and then at ambient temperature for 2 hours. Work-up as described in Example 98b, but without treatment with ethereal hydrogen chloride, gave 1-[3-(α,α-diethylbenzylamino)propyl]imidazol-4-yl-methyl acetate as an oil.

EXAMPLE 104

In the preparation of capsules, 10 parts by weight of active compound and 240 parts by weight of lactose are de-aggregated and blended. The mixture is filled into hard gelatin capsules, each capsule containing 10 mg active compound.

EXAMPLE 105

Tablets are prepared from the following ingredients.

|  | Parts by Weight |
| --- | --- |
| Active compound | 10 |
| Lactose | 190 |
| Maize starch | 22 |
| Polyvinylpyrrolidone | 10 |
| Magnesium stearate | 3 |

The active compound, the lactose and some of the starch are de-aggregated, blended and the resulting mixture is granulated with a solution of the polyvinylpyrrolidone in ethanol. The dry granulate is blended with magnesium stearate and the rest of the starch. The mixture is then compressed in a tableting machine to give tablets containing 10 mg of active compound.

EXAMPLE 106

Tablets are prepared by the method of the previous Example. The tablets are enteric coated in a conventional manner using a solution of 20% cellulose acetate phthalate and 3% diethyl phthalate in ethanol:dichloromethane (1:1).

EXAMPLE 107

In the preparation of suppositories, 100 parts by weight of active compound is incorporated in 1300 parts by weight of semi-synthetic glycerides as the suppository base and the mixture formed into suppositories each containing 100 mg of active ingredient.

EXAMPLE 108

In the preparation of capsules, 50 parts by weight of active compound, 300 parts by weight of lactose and 3 parts by weight of magnesium stearate are de-aggregated and blended. The mixture is filled into hard gelatin capsules, each capsule containing 50 mg of active ingredient.

EXAMPLE 109

The active compound is incorporated into the base by thorough homogenization until the drug is evenly distributed. The ointment is packed into 10 g amber jars with screw-capped lined lids.

Active compound 0.1 g
White soft paraffin to 10 g
Preparation of Starting Materials
Unless otherwise stated, the starting materials used in the Examples were commercially available and may be obtained by reference to the Fine Chemicals Directory.
2,4-Dimethylimidazole and 2-benzyl-4 (5)-methylimidazole were obtained from Polyorganix Inc MA.

51

4 (5)-Methyl-2-phenylimidazole was obtained from TCI (Tokyo Kasei Kogyo Co Ltd).

4-Formylimidazole was obtained from the Maybridge Chemical Co Ltd.

The following were prepared according to literature methods: 4,5-dimethylimidazole [Chem Ber 86, 88 (1953)], 2,4,5-trimethylimidazole [Chem Ber 86, 96 (1953))]and 2-benzoylimidazole [Synthesis 1978, 675].

EXAMPLE A a) A solution of imidazole (13.6 g) in dry DMF (50 ml) was added dropwise to a stirred suspension of sodium hydride (8.0 g, 60% dispersion in oil) in dry DMF (250 ml) at ambient temperature under nitrogen for 2.5 hours. A slurry of N-(4-bromobutyl)phthalimide (53.6 g) in dry DMF (80 ml) was added and the mixture heated at 95° C. for 16 hours. The solvent was evaporated off under vacuum and the residue was extracted with hot toluene. The combined toluene extracts were evaporated to dryness and the residue triturated with ether and dried to give N-[4-(imidazol-1-yl)butyl]phthalimide, m.p. 76°–79° C.

b) A mixture of the phthalimide (19.5 g) and hydrochloric acid (6M; 226 ml) was heated under reflux for 8 hours and then allowed to stand at ambient temperature for 18 hours. The mixture was cooled to 0° C. for 2 hours and the solid formed was removed by filtration. The filtrate was evaporated to dryness and the residue was partitioned between ethyl acetate and water. The aqueous layer was basified with concentrated sodium hydroxide solution and extracted with dichloromethane. The combined dichloromethane extracts were dried, filtered and the filtrate evaporated to give 4-(imidazol-1-yl)butylamine as an oil which was distilled at 120° C. (0.45 mmHg).

EXAMPLE B a) A solution of 2-phenylimidazole (14.4 g) in dry DMF (25 ml) was added dropwise to a stirred suspension of sodium hydride (4.0 g, 60% dispersion in oil) in dry DMF (125 ml) at ambient temperature under nitrogen for 2 hours. A slurry of N-(3-bromopropyl)phthalimide (25.5 g) in dry DMF (40 ml) was added and the mixture heated at 100° C. for 16 hours. The solvent was evaporated off and the residue was extracted with hot toluene. The combined toluene extracts were evaporated to dryness and the residue triturated with ether and dried to give N-[3-(2-phenylimidazol-1-yl)propyl]phthalimide, m.p. 109°–110.5° C.

b) A mixture of N-[3-(2-phenylimidazol-1-yl)propyl]phthalimide (17.0 g), sodium hydroxide (1.1 g) and water (5.4 ml) was heated at 95° C. for 48 hours. On cooling, a mixture of concentrated hydrochloric acid (66 ml) and water (13 ml) was added and the mixture boiled under reflux for 6 hours. After standing at ambient temperature for 16 hours, the mixture was filtered and the filtrate evaporated to dryness under reduced pressure. The residue was treated with water (16 ml) then cooled and sodium hydroxide (24 g) added in portions. The solution was extracted with diethyl ether and then with dichloromethane. The combined organic extracts were dried and evaporated to give an oil which was distilled under reduced pressure to give 3-(2-phenylimidazol- 1-yl) propylamine, b.p. 128° C. (0.05 mmHg).

EXAMPLE C

A solution of 4'-chloro-2'-hydroxyacetophenone (1.0 g) in dry DMF (5 ml) was added to a stirred mixture of sodium hydride (0.235 g, 60% dispersion) in dry DMF (5 ml) at 5° C. under nitrogen. After the addition the mixture was stirred at 0° C. for 15 minutes and then at ambient temperature for 1 hour. A solution of iodomethane (0.92 g) in dry DMF (5 ml) was added dropwise to the mixture whilst keeping the temperature below 10° C. The reaction mixture was stirred at ambient temperature for 5 hours and then left to stand for 16 hours. Potassium carbonate solution was added to basify the mixture and the product was extracted into dichloromethane. The combined extracts were dried and evaporated. The residue was dissolved in ether, washed with water, then dried and evaporated to give 4'-chloro-2'-methoxyacetophenone which was sufficiently pure for synthetic use in Example 17.

EXAMPLE D

In a similar manner to Example C, 4'-chloro-2'-hydroxyacetophenone (1.0 g) was treated with sodium hydride (0.235 g, 60% dispersion) and then with iodoethane (1.0 g) in DMF (15 ml, total) to give 4'-chloro- 2'-ethoxyacetophenone, m.p. 92°–93° C. (after recrystallisation from petroleum ether b.p. 60°–80° C.).

EXAMPLE E

A solution of n-butyllithium in hexane (30.4 ml, 2.5M) was added dropwise with stirring under nitrogen to a solution of N,N,N'-trimethylethylenediamine (7.9 g) in dry THF (150 ml) at −15 to −20° C. After the addition the mixture was stirred at −23° C. for 15 minutes and then 4-chlorobenzaldehyde (10.0 g) was added dropwise at −15 to −20° C. After the addition the mixture was stirred at −23° C. for 15 minutes and then more n-butyllithium in hexane (85.4 ml, 2.5M) was added dropwise at −15° C. The mixture was stirred at −23° C. for 3 hours, cooled to −40° C. and iodomethane (60.6 g) added at −40° to −20° C. After the addition, the mixture was stirred at −40° C. for 5 minutes and then allowed to warm up to ambient temperature and then stirred at that temperature for 30 minutes. The mixture was carefully poured into ice cold 10% hydrochloric acid (2 1) and left standing for 64 hours. The mixture was extracted with diethyl ether to give an oil which was distilled twice under vacuum to give 4-chloro-2-methylbenzaldehyde, b.p. 105°–110° (15 mmHg) which was sufficiently pure for synthetic use in Example 40.

EXAMPLE F

1) In a similar manner to Example A, a mixture of 2,4-dimethylimidazole (24.0 g) was added to a suspension of sodium hydride (10.0 g, 60% dispersion) in DMF (300 ml). After stirring for. 1.5 hours, DMF (80 ml) was added followed by a slurry of N-(3-bromopropyl)phthalimide (63.8 g) in DMF (100 ml). The mixture was reacted and worked up as in Example A and the residue triturated with petroleum ether b.p. 60°–80° C. and then with ether. The residue was recrystallised from ethyl acetate to give N-[3-(2,4-dimethylimidazol-1-yl)propyl]phthalimide, m.p. 191°–122° C. $^1$H nmr indicated the presence of approximately 10% of N-[3-(2,5-dimethylimidazol-1-yl)propyl]phthalimide.

2) The phthalimide from part 1) (18.2 g) was dissolved in IMS (600 ml) and treated with hydrazine hydrate (19.3 g) at ambient temperature with stirring. After stirring for 3 days the mixture was filtered and the residue washed with IMS. The combined filtrate and washings were evaporated to dryness. The residue was treated with 10M sodium hydroxide and the mixture extracted with dichloromethane. The combined organic extracts were washed with brine, dried and evaporated to give 3-(2,4-dimethylimidazol-1-yl)propylamine as an oil. $^1$H nmr indicated the presence of 10% of 3-(2,5-dimethylimidazol-1-yl)propylamine.

EXAMPLES G–J

In a similar manner to Example F (1), compounds of formula XXI in which A represents $(CH_2)_2$ and Z represents bromo were reacted with imidazoles of formula. YH, in which Y represents a group of formula XXVII in which $R_8$, $R_9$ and $R_{10}$ are given below, to give compounds of formula XIV as summarised in Table J. Compounds of formula XIV were then treated with hydrazine hydrate in a similar manner to Example F (2) to give compounds of formula V in which A represents —$(CH_2)_2$—, as summarised in Table K.

The compounds prepared in Table J were:

Ex G(1) N-[3-(2-Methylimidazol-1-yl)propyl]phthalimide, m.p. 119°–121° C.

Ex H(1) N-[3-(4,5-Dimethylimidazol-1-yl)propyl]phthalimide, m.p. 119°–121° C. after recrystallisation from ethyl acetate.

Ex I(1) N-[3-(4-methylimidazol-1-yl)propyl]phthalimide, m.p. 82°–90° C.

Ex J(1) N-[3-(2-Benzyl-4-methylimidazol-1-yl)propyl]phthalimide as an oil.

EXAMPLES K a) (±) 1-(4-Chlorophenyl)ethylamine was prepared as described in Example 52a.

The (+)-enantiomer (starting material for Example 56) was prepared in conventional manner as follows. A mixture of (±)1-(4-chlorophenyl)ethylamine (73 g) and D(–) tartaric acid (70 g) in industrial methylated spirits (IMS) (4.2 l) was allowed to stand at ambient temperature for 2 days. The solid formed was collected by filtration, washed with IMS and recrystallised from IMS to give (+)1-(4-chlorophenyl)ethylamine (–) tartrate, m.p. 195°–199° C. The salt was suspended in water and basified with aqueous ammonia (specific gravity 0.88). The mixture was extracted with diethyl ether to give (+)1-(4-chlorophenyl)ethylamine which was distilled at 120°–125° C. (30 mmHg). Chiral HPLC indicated enantiomeric purity of 97.4%.

The (–)-enantiomer (starting material for Example 57) was prepared in conventional manner as follows. A warm solution of (±)1-(4-chlorophenyl)ethylamine (101 g) and L(+)tartaric acid (97.3 g) in IMS (7 l) was allowed to cool slowly and to stand at ambient temperature for 3 days. The solid formed was collected by filtration, washed with IMS and recrystallised twice from IMS to give (–)-1-(4-chlorophenyl)ethylamine (+) tartrate, m.p. 195°–196° C. The salt

TABLE J

| Example | YH $R_8R_9R_{10}$ | Amt/g | NaH Amt/g | XXI Amt/g | Total DMF Vol/ml | Time hours | Notes |
|---|---|---|---|---|---|---|---|
| G(1) | 2-CH$_3$ | 41.0 | 20.0 | 127.3 | 980 | 16 | |
| H(1) | 4,5-(CH$_3$)$_2$ | 7.7 | 4.6 | 14.8 | 115 | 16 | (1) |
| I(1) | 4-CH$_3$ | 24.6 | 12.0 | 76.4 | 480 | 16 | |
| J(1) | 2-CH$_2$C$_6$H$_5$,4-CH$_3$ | 43.0 | 10.0 | 64.5 | 475 | 18 | (1) |

Notes
(1) The oil obtained after evaporation of the toluene was triturated with hot ether (3 × 400 ml). An insoluble oil was discarded. The product was obtained by evaporation of the ether.

TABLE K

| Example | XIV $R_8R_9R_{10}$ | Amt/g | Hydrazine Hydrate Amt/g | Ethanol Vol/ml | Time (Hours) | Notes |
|---|---|---|---|---|---|---|
| G(2) | 2-CH$_3$ | 30.0 | 44.8 | 900 | 24 | |
| H(2) | 4,5-(CH$_3$)$_2$ | 8.8 | 9.3 | 250 | 24 | |
| I(2) | 4-CH$_3$ | 40.0 | 44.8 | 1200 | 24 | |
| J(2) | 2-CH$_2$C$_6$H$_5$,4-CH$_3$ | 70.0 | 48.8 | 1500 | 36 | (1) |

Notes
(1) The oil obtained was distilled.

The compounds prepared in Table K were:

Ex G(2) 3-(2-Methylimidazol-1-yl)propylamine as an oil not distilled.

Ex H(2) 3-(4,5-Dimethylimidazol-1-yl)propylamine as an oil not distilled.

Ex I(2) 3-(4-Methylimidazol-1-yl)propylamine as an oil not distilled. $^1$H nmr indicated the presence of approximately 33% of 3-(5-methylimidazol-1-yl)propylamine.

Ex J(2) 3-(2-Benzyl-4-methylimidazol-1-yl)propylamine, b.p. 160°–165° at 0.35 mmHg. Glc indicated the presence of approximately 20% of 3-(2-benzyl-5-methylimidazol-1-yl)propylamine.

was suspended in water and basified with aqueous ammonia (specific gravity 0.88). The mixture was extracted with diethyl ether to give (–) 1-(4-chlorophenyl)ethylamine (free base) which was distilled at 122°–124° C. (28 mmHg). Chiral HPLC indicated enantiomeric purity of 96.8%.

EXAMPLE L a) A solution of 4-chlorophenylacetonitrile (70 g) in dry THF (50 ml) was added with stirring to a suspension of sodium hydride (39.7 g, 60% dispersion) in boiling THF (100 ml) under reflux, under nitrogen at a rate such that boiling was maintained without heating the flask. After the addition the mixture was boiled under reflux for 2 hours. More THF (100 ml) was added and the mixture cooled to 10° C. A solution of iodomethane (139 g) in THF (50 ml) was added dropwise to the mixture over 2 hours whilst keeping the temperature below 10° C. The mixture was stirred at ambient temperature for 18 hours then kept below 10° C. while methanol (30 ml) was added dropwise, followed by water (150 ml). The mixture was allowed to warm up to ambient temperature and then concentrated under reduced pressure to remove the THF. The residue was diluted with water and extracted with dichloromethane. The combined extracts were dried and evaporated to give an oil which was distilled under vacuum to give 2-(4-chlorophenyl)-2-methylpropionitrile, b.p. 90°–94° C. (0.5 mmHg).

b) A solution of the propionitrile (10 g), from part (a) above, in IMS (30 ml) was treated with a solution of sodium hydroxide (0.67 g) in water (3.3 ml). The mixture was warmed to 50° C. and hydrogen peroxide (14 ml, 60% w/v) was added dropwise with stirring. The mixture was stirred at ambient temperature for 3 hours and then evaporated to dryness under reduced pressure. The residue was partitioned between ethyl acetate and water. The mixture was separated and the aqueous layer extracted with ethyl acetate. The combined organic layers were washed, dried and evaporated to give 2-(4-chlorophenyl)- 2-methylpropionamide, m.p. 125° C.

c) A boiling solution of the amide from (b) (68.3 g) in acetonitrile (500 ml) was added in one portion to a warm (approx. 50° C.) stirred suspension of hydroxy(tosyloxy) iodobenzene (165.3 g) in acetonitrile (800 ml). The resulting exotherm was controlled by external cooling. The mixture was boiled under reflux with vigorous stirring for 1 hour. The solvent was removed under reduced pressure and the residue mixed thoroughly with ethyl acetate (500 ml) and water (500 ml). The solid was collected by filtration through a filter agent (95% silicon dioxide, acid washed, Celite® 521). This residue was added to hot water (150 ml) to form a suspension which was basified with solid sodium hydroxide with external cooling. This mixture was extracted with diethyl ether and the combined extracts dried over magnesium sulphate and filtered. The filtrate was acidified with ethereal hydrogen chloride and the solid formed was collected by filtration and recrystallised from aqueous acetonitrile to give 1-(4-chlorophenyl)-1-methylethylamine hydrochloride, m.p. 246° C.

d) Acryloyl chloride (0.88 g) was added dropwise with stirring to a solution of 1-(4-chlorophenyl)-1-methylethylamine hydrochloride (2.0 g) and triethylamine (2.07 ml) in dichloromethane (10 ml) at −15° to −2.0° C. under nitrogen. After the addition, the mixture was stirred at ambient temperature for 2.5 hours. The mixture was diluted with 5M sodium hydroxide solution and then with water. The dichloromethane layer was separated to give N-[1-(4-chlorophenyl)-1-methylethyl]acrylamide, m.p. 114°–117° C. (m.p. 122°–123° C. after recrystallisation).

The α,α-dialkylsubstituted benzylamines required as starting materials in Table H were prepared in a similar manner to Example L as summarised in Tables L–O which summarise the corresponding stages a, b, c and d of Example L, respectively.

In Table L compounds of formula XXVIII in which $R_4$ and $R_5$ represent hydrogen were alkylated to give compounds of formula XXVIII in which $R_4=R_5$. In Table M compounds of formula XXVIII were converted into compounds of formula XXV.

In Table N compounds of formula XXV were converted into compounds of formula XVII in which $R_6$=hydrogen.

In Table O compounds of formula VII in which $R_6$=hydrogen were converted into compounds of formula XVI in which $R_6$ represents hydrogen.

TABLE L

| Ex | XXVIII $R_1R_2R_3$ | THF Wt/g | NaH Vol/ml | THF Vol/ml | $R_4$ | $R_4$I Wt/g | b.p. of XXX |
|---|---|---|---|---|---|---|---|
| M | 4-CH$_3$ | 100 | 100 | 65.5 | 250 | CH$_3$ | 230 | 102–106 (10 mmHg) |
| O | 4-CO$_2$CH$_3$ | 5 | 20 | 2.4 | 20 | CH$_3$ | 8.4 | 120 (0.8 mmHg) |
| P | 4-Ph | 50 | 175 | 22.4 | 175 | CH$_3$ | 78.3 | m.p. 83–85° C. |
| Q | 4-Cl | 70 | 75 | 40 | 225 | C$_2$H$_5$ | 156 | 88–94 (0.6 mmHg) |
| R | —(CH:CH)$_2$— | 50.3 | 200 | 25.9 | 234 | CH$_3$ | 90.6 | 138–142 (1.2 mmHg)$^+$ |
| S | 3,4-Cl$_2$ | 200 | 120 | 92.4 | 700 | CH$_3$ | 323 | 114–116 (0.4 mmHg) |
| T | 4-OCH$_2$Ph | 74.4 | 200 | 28.6 | 100 | CH$_3$ | 100 | m.p. 51–52° C. |

$^+$Oil washed with petrol before distillation to remove mineral oil which otherwise codistils

TABLE M

| Ex | XXVIII $R_1R_2R_3$ | $R_4$ | Wt of XXVIII (g) | NaOH (g) | H$_2$O (ml) | IMS (ml) | H$_2$O$_2$ (ml) | m.p. of XXV °C. |
|---|---|---|---|---|---|---|---|---|
| M | 4-CH$_3$ | CH$_3$ | 100 | 7.6 | 28 | 350 | 158 | 140–142 |
| P | 4-Ph | CH$_3$ | 45.4 | 2.5 | 12 | 300 | 51.6 | 201–203 |
| R | —(CH:CH)$_2$— | CH$_3$ | 51.2 | 3.2 | 15.5 | 125 | 66 | 144–146 |
| S | 3,4-Cl$_2$ | CH$_3$ | 208.5 | 11.7 | 58 | 650 | 245 | 116–117 |
| T | 4-OCH$_2$Ph | CH$_3$ | 2.0 | 0.095 | 0.47 | 10 | 2.0 | 150–151 |

TABLE N

| Ex | XXV R$_1$R$_2$R$_3$ | R$_4$ | Wt of XXV (g) | CH$_3$CN | PhI(OH) OTos | CH$_3$CN | m.p. of VII HCl °C. |
|---|---|---|---|---|---|---|---|
| M | 4-CH$_3$ | CH$_3$ | 49.8 | 400 | 134 | 650 | 239–241 |
| N | H | C$_2$H$_5$ | 32.9 | 240 | 82.0 | 390 | 265–266 (1) |
| O | 4-CO$_2$C$_2$H$_5$ | CH$_3$ | 0.44 | 10 | 0.74 | 10 | 208–209 |
| P | 4-Ph | CH$_3$ | 5.0 | 60 | 8.3 | 32 | >310 |
| Q | 4-Cl | C$_2$H$_5$ | 20.9 | 130 | 44.3 | 210 | >300 |
| R | —(CH:CH)$_2$— | CH$_3$ | 8.2 | 32 | 4.46 | 50 | 244–248 |
| T | 4-OCH$_2$Ph | CH$_3$ | 5.0 | 70 | 8.9 | 70 | 223–224 |

(1) For preparation of starting material see J. Pharm. Pharmacol. 1957, 9, 20

TABLE O

| Ex | VII R$_1$R$_2$R$_3$ | R$_4$ | Wt of VII HCl (g) | Et$_3$N (ml) | CH$_2$Cl$_2$ (ml) | CH$_2$=CHCOCl Wt (g) | Notes |
|---|---|---|---|---|---|---|---|
| M | 4-CH$_3$ | CH$_3$ | 11.0 | 16.4 | 60 | 5.4 | (1) |
| N | H | C$_2$H$_5$ | 20.0 | 27.8 | 160 | 9.1 | |
| O | 4-CO$_2$C$_2$H$_5$ | CH$_3$ | 7.9 | 5.3 | 80 | 3.5 | |
| P | 4-Ph | CH$_3$ | 16.5 | 13.4 | 170 | 6.0 | |
| Q | 4-Cl | C$_2$H$_5$ | 10.8 | 12.8 | 50 | 4.2 | |
| R | —(CH:CH)$_2$— | CH$_3$ | 26.5 | 33.3 | 170 | 10.8 | |
| S | 3,4-Cl$_2$ | CH$_3$ | 190 | 159 | 1100 | 71.5 | (2) |
| T | 4-OCH$_2$Ph | CH$_3$ | 25.0 | 14.4 | 250 | 9.6 | (3) |
| U | 4-Cl | —CH$_2$CH$_2$— | 20.4 | 32.0 | 200 | 9.1 | * |

*For preparation of starting material, see Chem. Ber. 1979, 112, 3914
Notes
(1) m.p. 131–134° C.
(2) m.p. 138–140° C.
(3) m.p. 116–117° C.

Example S stage c

Bromine (139 g) was added dropwise with stirring to a solution of 3 molar sodium hydroxide (1712 ml) at 0° C. with stirring. When all the bromine had dissolved, 2-(3,4-dichlorophenyl)-2-methylpropionamide (201 g) was added in portions of 0° C. The mixture was stirred at 0° C. for 5 hours and then left to stand at 0° C. for 18 hours. The mixture was heated at 95° C. for 1 hour, then cooled and extracted with ether. The combined ether extracts were washed with 5M hydrochloric acid whereupon a solid precipitated. The solid was collected by filtration to give 2-(3,4-dichlorophenyl)- 2-methylpropylamine hydrochloride, m.p. 238°–239° C.

Example O stage b 2-(4-Chlorophenyl)-2-ethylbutyronitrile (104.9 g) was added to a boiling solution of potassium hydroxide (40.3 g) in pentan-1-ol (450 ml) with stirring. The mixture was boiled under reflux for 24 hours. The mixture was cooled and poured into an equal volume of water. The mixture was washed with ether and then the aqueous layer was extracted with dichloromethane to give an oil which solidified on standing. The solid was triturated with cyclohexane and filtered to give 2-(4-chlorophenyl)-2-ethylbutyramide, m.p. 107°–109° C.

Example O stage b a) A mixture of methyl 4-(1-cyano-1-methylethyl)benzoate (1.0 g), sodium hydroxide (0.4 g), water (2 ml) and IMS (5 ml) was heated to 50° C. with stirring. Hydrogen peroxide (60% w/v, 1.23 ml) was added dropwise and the reaction mixture was stirred at 50° C. for 1 hour. and then at ambient temperature for 3 hours. The reaction mixture was evaporated to dryness under reduced pressure. Water (10 ml) was added to the residue and this mixture was heated at 95° C. for 1 hour. The mixture was cooled, washed with dichloromethane, acidified with 5M hydrochloric acid and filtered to give 4-(1-carbamoyl- 1-methylethyl)benzoic acid, m.p. 218°–219° C.

b) The acid from a) (0.70 g), absolute ethanol (7 ml) and concentrated sulphuric acid (2 drops) were boiled under reflux for 4 hours. The ethanol was removed under reduced pressure and water added to the residue. Extraction with dichloromethane yielded ethyl 4-(1-carbamoyl-1-methylethyl)benzoate, m.p. 104°–109° C. (Glc indicated ~10% of ethyl 4-(1-ethoxycarbonyl-1-methylethyl)benzoate.

Example V a) Acryloyl chloride (86.9 g) was added dropwise with stirring to a solution of 4-chlorobenzylamine (135.8 g) and triethylamine (133.5 ml) in dichloromethane (500 ml) at -15 to -20° C., under nitrogen. After the addition the mixture was stirred at ambient temperature for 2.5 hours. The mixture was washed with dilute aqueous sodium hydroxide solution and then with water. The dichloromethane solution was dried and evaporated under reduced pressure. The solid residue was recrystallised from ethyl acetate to give N-(4-chlorobenzyl)acrylamide, m.p. 103°–104° C.

Example W a) In a similar manner to Example 62a, a mixture of acryloyl chloride (58.2 g) was added to 1-(4-chlorophenyl) ethylamine (100 g) and triethylamine (65.2 g) in dichloromethane (400 ml) to give N-[1-(4-chlorophenyl)ethyl] acrylamide, m.p. 103°–104° C.

Example X a) In a similar manner to Example A, 4(5)-methyl-2-phenylimidazole (25.0 g) was reacted with sodium hydride (6.3 g, 60% dispersion) in DMF and then with N-(3-bromopropyl)phthalimide (40.4 g) to give N-{3-[(4/5)-methyl- 2-phenylimidazol-1-yl]propyl}phthalimide which was used directly in part (b).

b) The phthalimide (50.0 g) from part a) was treated with hydrazine hydrate (43.7 g) in IMS (1400 ml) in a similar manner to Example F to give 3-(4-methyl-2-phenylimidazol- 1-yl)propylamine as an oil, b.p. 156°14 160° C. (0.4 mmHg) which was purified by conversion into the hydrochloride salt using ethereal hydrogen chloride and then conversion back into the free base using 5M sodium hydroxide. Glc indicated that the product contained 12% (approx.) of 3-(5-methyl-2-phenylimidazol-1-yl)propylamine.

We claim:

1. Compounds of formula II

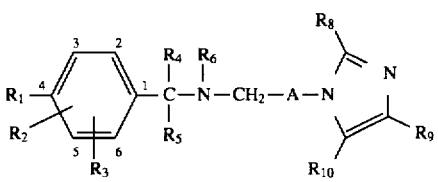

and pharmaceutically acceptable salts thereof in which $R_1$ represents halo, a $C_{1-4}$ alkyl group, a $C_{2-4}$ alkoxy group, phenoxy, phenyl, a $C_{2-4}$ alkoxycarbonyl group, a perhalo $C_{1-2}$ alkoxy group, a perhalo $C_{1-2}$ alkyl group, benzyloxy, an amino group of formula $NR_{13}R_{14}$ (in which $R_{13}$ and $R_{14}$ independently represent hydrogen or a $C_{1-4}$ alkyl group), a ($C_{2-4}$alkoxycarbonyl)vinyl group, a $C_{2-6}$ alkoxycarbonyl $C_{1-2}$ alkyl group or $R_1$ and $R_2$ together with the phenyl ring to which they are attached represent a naphthyl group;

$R_2$ and $R_3$ independently represent hydrogen, halo, a $C_{1-4}$ alkyl group, a $C_{1-4}$ alkoxy group, a perhalo $C_{1-2}$ alkyl group, or hydroxy;

$R_4$ and $R_5$ independently represent hydrogen, a $C_{1-4}$ alkyl group, phenyl or $R_4$ and $R_5$ together with the carbon atom to which they are attached represent a $C_{3-6}$ cycloalkyl group;

$R_6$ represents hydrogen or a $C_{1-3}$ alkyl group;

A represents ethylene [trimethylene, tetramethylene, 1,1-dimethylethylene or heptamethylene];

$R_8$ represents hydrogen, a $C_{1-4}$ alkyl group, phenyl or benzyl; and $R_9$ and $R_{10}$ independently represent hydrogen, a $C_{1-4}$ alkyl group, halo, a $C_{1-4}$ hydroxyalkyl group, a $C_{2-6}$ alkoxycarbonyl group, nitro, or a $C_{1-6}$ alkanoyloxy $C_{1-2}$ alkyl group.

2. Compounds according to claim 1 in which $R_1$ represents bromo, chloro, methyl, ethyl, t-butyl, butoxy, phenoxy, phenyl, methoxycarbonyl, ethoxycarbonyl, propoxycarbonyl, dimethylamino, trifluoromethoxy, trifluoromethyl, benzyloxy, 2-ethoxycarbonylvinyl or $R_1$ and $R_2$ together with the phenyl ring to which they are attached represent a naphthyl group.

3. Compounds according to claim 1 in which $R_2$ represents hydrogen, 3-chloro, 2-chloro, 3-fluoro, 2-methyl, 3-methyl, 2-methoxy, 2-ethoxy, 2-hydroxy or 3-trifluoromethyl and $R_3$ represents hydrogen, 2-chloro or 3-chloro.

4. Compounds according to claim 1 in which $R_6$ represents hydrogen or methyl.

5. Compounds according to claim 1 in which $R_8$ represents hydrogen, methyl, ethyl, isopropyl, phenyl or benzyl.

6. Compounds according to claim 1 in which $R_9$ and $R_{10}$ independently represent hydrogen, methyl, chloro, hydroxymethyl, ethoxycarbonyl, nitro or acetoxymethyl.

7. A compound of formula II as claimed in claim 1 which is N-[1-(4-Chlorophenyl)-1-methylethyl]-3-(imidazol-1-yl)-propylamine and pharmaceutically acceptable salts thereof.

8. A pharmaceutical composition comprising a therapeutically effective amount of a compound of formula II of claim 1 in combination with pharmaceutically acceptable diluent or carrier.

9. A pharmaceutical composition according to claim 8, formulated as a tablet.

10. A pharmaceutical composition according to claim 8 suitable for inhalation via the mouth and/or nose.

11. A pharmaceutical composition according to claim 8 suitable for topical administration.

12. A compound selected from the group consisting of:

N-[1-(2,4-Dichlorophenyl)ethyl]-3-(imidazol-1-yl)-propylamine;

N-[1-(4-Benzyloxyphenyl)ethyl]-3-(imidazol-1-yl)propylamine;

N-[1-(4-Chloro-3-trifluoromethylphenyl)ethyl]-3-(imidazol-1-yl) propylamine;

N-[1-(4-Chloro -3-fluorophenyl)ethyl]-3-(imidazol-1-yl) propylamine;

3-(Imidazol-1-yl)-N-[1-(4-trifluoromethylphenyl)ethyl] propylamine;

N-[1-(4-Chloro -3-methylphenyl)ethyl]-3-(imidazol-1-yl) propylamine;

N-[1-(2,3,4-Trichlorophenyl)ethyl]-3-(imidazol-1-yl)propylamine;

3-(Imidazol-1-yl)-N-[1-(4-phenoxyphenyl)ethyl]propylamine;

N-[1-(4-Tert-butylphenyl)ethyl]-3-(imidazol-1-yl)propylamine;

N-[1-(4-Butoxyphenyl)ethyl]-3-(imidazol-1-yl)propylamine;

3-(Imidazol-1-yl)-N-[1-(4-trifluoromethoxyphenyl)ethyl] propylamine;

N-[1-(4-Chlorophenyl)ethyl]-3-(4,5-dimethylimidazol-1-yl) propylamine;

N-[1-(4-Chlorophenyl)ethyl]-3-(2-phenylimidazol-1-yl) propylamine;

N-[1-(4-Chlorophenyl)ethyl]-3-(2-methylimidazol-1-yl) propylamine;

N-[α-(4-chlorophenyl)benzyl]-3-(imidazol-1-yl)propylamine;

5-Chloro-2-{1-[3-(imidazol-1-yl)propylamino] ethyl}phenol;

N-[1-(4-Chlorophenyl)propyl]-3-(imidazol-1-yl)propylamine;

N-[1-(4-Chlorophenyl)ethyl]-3-(2,4-dimethylimidazol-1-yl)propylamine;

3-(2-Benzyl-4-methylimidazol-1-yl)-N-[1-(4-chlorophenyl)ethyl]propylamine;

3-(2-Benzyl-5-methylimidazol-1-yl)-N-[1-(4-chlorophenyl)ethyl]propylamine;

N-[1-(4-Chlorophenyl)ethyl]-3-(4-methyl-2-phenylimidazol-1-yl)propylamine;

N-[1-(4-Chlorophenyl)ethyl]-3-(5-methyl-2-phenylimidazol-1-yl)propylamine;

N-Benzhydryl -3-(imidazol-1-yl)propylamine;

N-(3,4-Dichlorobenzyl)-3-(imidazol-1-yl)propylamine;

3-(Imidazol-1-yl)-N-(4-phenoxybenzyl)propylamine;

N-(4-Chlorobenzyl)-3-(2-methylimidazol-1-yl)propylamine;

N-(4-Chlorobenzyl)-3-(4-methylimidazol-1-yl)propylamine;

N-(4-Chlorobenzyl)-3-(5-methylimidazol-1-yl)propylamine;

N-(4-Chlorobenzyl)-3-(4,5-dimethylimidazol-1-yl)propylamine;

N-(4-Chlorobenzyl)-3-(5-methyl-2-phenylimidazol-1-yl)propylamine;

N-(4-Chlorobenzyl)-3-(4-methyl-2-phenylimidazol-1-yl)propylamine;

Methyl 4-[3-(2-methylimidazol-1-yl)propylaminomethyl]benzoate;

3-(Imidazol-1-yl)-N-(4-methoxy-2,6-dimethylbenzyl)propylamine;

Ethyl 4-[3-(2-methylimidazol-1-yl)propylaminomethyl]cinnamate;

(−) N-[1-(4-Chlorophenyl)ethyl]-3-(imidazol-1-yl)propylamine;

N-[1-(4-Chlorophenyl)ethyl]-3-(2-ethylimidazol-1-yl)propylamine;

N-[1-(4-Chlorophenyl)ethyl]-3-(4-methylimidazol-1-yl)propylamine;

N-[1-(4-Chlorophenyl)ethyl]-3-(5-methylimidazol-1-yl)propylamine;

(+) N-[1-(4-Chlorophenyl)ethyl]-3-(imidazol-1-yl)propylamine;

N-[1-(4-Chlorophenyl)-1-methylethyl]-3-(imidazol-1-yl)propyiamine;

N-[1-(4-Chlorophenyl)-1-methylethyl]-3-(2-methylimidazol-1-yl)propylamine;

N-(4-Chlorobenzyl)-3-(4,5-dichloroimidazol-1-yl)propylamine;

N-[1-(4-Chlorophenyl)ethyl]-3-(2-isopropylimidazol-1-yl)propylamine;

N-[1-(4-Chlorophenyl)ethyl]-3-(2,4,5-trimethylimidazol-1-yl)propylamine;

N-[1-(4-Chlorophenyl)ethyl]-3-(4,5-dichloroimidazol-1-yl)propylamine;

N-[1-(4-Chlorophenyl)-1-methylethyl]-3-(4-methylimidazol-1-yl)propylamine;

N-[1-(4-Chlorophenyl)-1-methylethyl]-3-(5-methylimidazol-1-yl)propylamine;

N-[1-(4-Chlorophenyl)-1-methylethyl]-3-(4,5-dimethylimidazol-1-yl)propylamine;

N-(4-Chlorobenzyl)-3-(2-isopropylimidazol-1-yl)propylamine;

N-(4-Chlorobenzyl)-3-(2-ethylimidazol-1-yl)propylamine;

3-(2-Methylimidazol-1-yl)-N-[1-methyl-1-(p-tolyl)ethyl]propylamine;

3-(Imidazol-1-yl)-N-[1-methyl-1-(p-tolyl)ethyl]propylamine;

1-(4-Chlorophenyl)-1-ethyl]-3'-(imidazol-1-yl)dipropylamine;

1-{3-[1-(4-Chlorophenyl)-1-methylethylamino]propyl}imidazol-4-yl-methanol;

N-[1-(4-Biphenyiyl)-1-methylethyl]-3-(imidazol-1-yl)propylamine;

N-[1-(4-Chlorophenyl)cycloprop-1-yl]-3-(imidazol-1-yl)propylamine;

N-[1-(2-Naphthyl)-1-methylethyl]-3-(imidazol-1-yl)propylamine;

1-{3-[1-(3,4-Dichlorophenyl)-1-methylethylamino]propyl}imidazol-5-yl-methanol;

1-{3-[1-(4-Biphenylyl)-1-methylethylamino]propyl}imidazol-4-yl-methanol;

N-[1-(4-Benzyloxyphenyl)-1-methylethyl]-3-(imidazol-1-yl)propylamine;

N-(4-Chlorobenzyl)-3-(2,4-dimethylimidazol-1-yl)propylamine;

3-(2-Benzyl-4-methylimidazol-1-yl)-N-(4-chlorobenzyl))propylamine;

Propyl 4-[3-(2-methylimidazol-1-yl)propylaminomethyl]benzoate;

1-{3-[1-(4-Chlorophenyl)-1-methylethylamino]propyl}-5-methylimidazol- 4-ylmethyl acetate;

and pharmaceutically acceptable salts thereof in the form of individual enantiomers, racemates or other mixtures of enantiomers.

13. A method of treating inflammatory and/or allergic diseases in a mammal in need of such treatment comprising administering a therapeutically effective amount of a compound of formula I

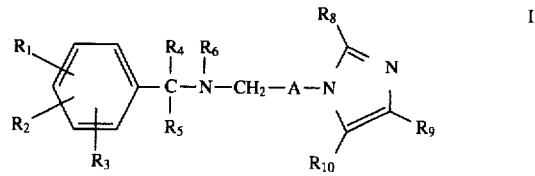

and pharmaceutically acceptable salts thereof in which $R_1$, $R_2$ and $R_3$ independently represent hydrogen, halo, a $C_{1-6}$ alkyl group, a $C_{1-6}$ alkoxy group, phenoxy (optionally substituted by a $C_{1-6}$ alkyl group, a $C_{1-4}$ alkoxy group or halo), phenyl (optionally substituted by a $C_{1-4}$ alkylgroup, a $C_{1-4}$ alkoxy group or halo), a $C_{2-6}$ alkoxycarbonyl group, an amino group of formula —$NR_{13}R_{14}$ (in which $R_{13}$ and $R_{14}$ are indeptendently hydrogen or a $C_{1-4}$ alkyl group or $R_{13}$ and $R_{14}$ together with he nitrogen atom to which they are attached represent a pyrrolidine ring, a morpholine ring or a piperidine ring), a halogenated $C_{1-4}$ alkoxy group, a halogenated $C_{1-4}$ alkyl group, benzyloxy (optionally substituted by a $C_{1-4}$ alkyl group, a $C_{1-4}$ alkoxy group or halo), hydroxy, a $C_{1-4}$ hydroxyalky group, a ($C_{2-6}$ alkoxycarbonyl)vinyl group; a group of formula —$S(O)_nR_7$ (in which $R_7$ represents a $C_{1-4}$ alkyl group and n is 0, 1 or 2), a $C_{2-4}$-carbamoylalkyl group, a $C_{2-6}$ alkoxycarbonyl $C_{1-2}$ alkyl group, a carbamoyl group of formula —$CONR_{11}R_{12}$ (in which $R_{11}$ and $R_{12}$ are independently hydrogen or a $C_{1-6}$ alkyl group) or $R_1$ and $R_2$ together with the phenyl ring to which they are attached represent a naphthyl group;

$R_4$ and $R_5$ independently represent hydrogen, a $C_{1-4}$ alkyl group, phenyl (optionally substituted by a $C_{1-4}$ alkyl group, halo or a $C_{1-4}$ alkoxy group) or $R_4$ and $R_5$ together with the carbon atom to which they are attached represent a $C_{3-6}$ cycloalkyl group;

$R_6$ represents hydrogen, a $C_{1-4}$ alkyl group or an ω-hydroxy $C_{1-4}$ alkyl group;

A represents a $C_{2-9}$ alkylene group, which may be straight or branched;

represents hydrogen, a $C_{1-6}$ alkyl group, halo, a $C_{1-4}$ alkoxy group, a $C_{1-4}$ hydroxyalkyl group, phenyl (optionally substituted by a $C_{1-4}$ alkyl group, halo or a $C_{1-4}$ alkoxy group) or benzyl (optionally substituted by a $C_{1-4}$ alkyl group, halo or a $C_{1-4}$ alkoxy group);

$R_9$ and $R_{10}$ independently represent hydrogen, a $C_{1-6}$ alkyl group, halo, a $C_{1-4}$ alkoxy group, phenyl (optionally substituted by a $C_{1-4}$ alkyl group, halo or a $C_{1-4}$ alkoxy group), a $C_{1-4}$ hydroxyalkyl group, a $C_{2-6}$ alkoxycarbonyl group, nitro, an amino group of formula $NR_{30}R_{31}$ (in which $R_{30}$ and $R_{31}$ independently represent hydrogen or a $C_{1-4}$ alkyl group), a $C_{1-6}$ alkanoyloxy $C_{1-4}$ alkylgroup, or an aminomethyl group;

with the provisos that 1) when A represents $(CH_2)_2$ and $R_2, R_3, R_4, R_5, R_6, R_8, R_9$ and $R_{10}$ represent hydrogen then $R_8$ does not represent hydrogen or 4-chloro, 2) when A represents $(C_2)_5$ and $R_1, R_2, R_3, R_4, R_5, R_6, R_9$ and $R_{10}$ represent hydrogen then $R_8$ does not represent methyl and 3) when $R_1, R_2, R_3, R_6 R_8, R_9$ and $R_{10}$ each represent hydrogen and A represents $(CH_2)_2$ then $R_4$ and $R_5$ are both methyl.

14. A method according to claim 13 wherein the disease is asthma.

* * * * *

UNITED STATES PATENT AND TRADEMARK OFFICE
CERTIFICATE OF CORRECTION

PATENT NO. : 5,547,972
DATED : August 20, 1996
INVENTOR(S) : Clegg et al.

It is certified that error appears in the above-indentified patent and that said Letters Patent is hereby corrected as shown below:

On the title page, item

[75], lines 3-4, delete "all of Nottinghamshire, United Kingdom" insert therefor -- all of Nottingham, United Kingdom --.

Item [30], line 1, delete "9127304" insert therefor -- 9127304.5 --.

Signed and Sealed this

Seventeenth Day of December, 1996

Attest:

BRUCE LEHMAN

Attesting Officer    Commissioner of Patents and Trademarks

UNITED STATES PATENT AND TRADEMARK OFFICE
CERTIFICATE OF CORRECTION

PATENT NO. : 5,547,972
DATED : Aug. 20, 1996
INVENTOR(S) : CLEGG et al

Page 1 of 2

It is certified that error appears in the above-indentified patent and that said Letters Patent is hereby corrected as shown below:

Column [59], line 54 and 55 please delete "ethylene[trimethylene, tetramethylene,1,1-dimethylethylene or heptamethylene];", insert therefor --ethylene;--.

Column [61], line 43 please delete "propyiamine" insert therefor --propylamine--. Line 46 please delete "3-(4,5-dichioroimidazol-" insert therefor -- 3-(4,5-dichloroimidazol--.

Column [63], line 7 please delete "represents hydrogen" insert therefor --$R_8$ represents hydrogen--. Line 8 please delete "$C_1$-hydroxyalkyl group" please insert therefor --$C_{1-4}$ hydroxy alkyl group--.

UNITED STATES PATENT AND TRADEMARK OFFICE
CERTIFICATE OF CORRECTION

PATENT NO. : 5,547,972
DATED : Aug. 20, 1996
INVENTOR(S) : CLEGG et al

It is certified that error appears in the above-indentified patent and that said Letters Patent is hereby corrected as shown below:

Column [64], line 7 please delete "$R_8$ does not represent hydrogen" insert therefor --$R_1$ does not represent hydrogen--. line 8 please delete " $(C_2)_5$" insert therefor --$(CH_2)_5$--. Line 10 please delete "$R_6R_8$" insert therefor --$R_6$, $R_8$ --Line 12 please delete "are both methyl." insert therefor --are not both methyl.--

Signed and Sealed this

Nineteenth Day of August, 1997

Attest:

BRUCE LEHMAN

Attesting Officer

Commissioner of Patents and Trademarks